US009604933B2

(12) United States Patent
Kamal et al.

(10) Patent No.: US 9,604,933 B2
(45) Date of Patent: Mar. 28, 2017

(54) PYRAZOLOCHALCONES AS POTENTIAL ANTICANCER AGENTS

(71) Applicant: COUNCIL OF SCIENTIFIC AND INDUSTRIAL RESEARCH, New Delhi (IN)

(72) Inventors: Ahmed Kamal, Hyderabad (IN); Shaik Anver Basha, Hyderabad (IN); Gajjela Bharath Kumar, Hyderabad (IN); Vangala Santhosh Reddy, Hyderabad (IN); Chityal Ganesh Kumar, Hyderabad (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/915,460

(22) PCT Filed: Dec. 16, 2013

(86) PCT No.: PCT/IN2013/000770
§ 371 (c)(1),
(2) Date: Feb. 29, 2016

(87) PCT Pub. No.: WO2015/029051
PCT Pub. Date: Mar. 5, 2015

(65) Prior Publication Data

US 2016/0207888 A1 Jul. 21, 2016

(30) Foreign Application Priority Data

Aug. 30, 2013 (IN) ........................... 2568/DEL/2013

(51) Int. Cl.
*C07C 231/12* (2006.01)
*C07D 405/14* (2006.01)
*C07D 405/06* (2006.01)
*C07D 231/12* (2006.01)

(52) U.S. Cl.
CPC ......... *C07D 231/12* (2013.01); *C07D 405/06* (2013.01); *C07D 405/14* (2013.01)

(58) Field of Classification Search
None
See application file for complete search history.

(56) References Cited

PUBLICATIONS

Database CAPLUS in STN, Acc. No. 2006:535161, Ashok et al., Heterocyclic Communications (2006), 12(2), pp. 103-106 (abstract).*

* cited by examiner

*Primary Examiner* — Brian J Davis
(74) *Attorney, Agent, or Firm* — Abelman, Frayne & Schwab

(57) ABSTRACT

The present invention relates to a pyrazolochalcone of formula A useful as potential antitumor agent against human cancer cell lines and a process for the preparation thereof. Formula A wherein, R1, R2, R3, R4, R5=H, Cl, F, $CH_3$, $OCH_3$, 3,4($OCH_2O$) X=H, Cl, $CH_3$, $OCH_3$, 3,4($OCH_2O$), $NH_2$, $NO_2$, OH, dotted line indicates optionally cyclic structure.

10 Claims, No Drawings

PYRAZOLOCHALCONES AS POTENTIAL ANTICANCER AGENTS

This application claims priority of International Application PCT/IN/2013/000770 filed on Dec. 16, 2013, and Indian patent application 2568/DEL/2013 filed on Aug. 30, 2013. Both are incorporated by reference in their entirety.

FIELD OF THE INVENTION

The present invention relates to pyrazolochalcones as potential anticancer agents. The present invention also relates to the synthesis and biological evaluation of novel pyrazolochalcones of formula A as potential anticancer agents.

BACKGROUND OF THE INVENTION

Tubulin is an essential eukaryotic protein that plays critical roles in cell division and is an established target of anticancer drug development. Combretastatins ($S_1$), chalcones ($S_2$), podophyllotoxins ($S_3$) and Colchicines ($S_4$) are the notable examples of compounds that inhibit microtubule assembly by binding to tubulin. Many mechanisms of action have been identified, including the inhibition of tubulin assembly, inhibition of angiogenesis, induction of apoptosis, anti-estrogenic activity and reversal of multidrug resistance or a combination of these mechanisms (Ducki, S. The development of chalcones as promising anticancer agents. Invest. New Drugs. 2007, 10, 42-46; Boumendjel, A., Boccard, J., Carrupt, P.-A., Nicolle, E., Blanc, M., Geze, A., Choisnard, L., Wouessidjewe, D., Matera, E.-L. and Dumontet, C. Antimitotic and Antiproliferative activities of chalcones. *J. Med. Chem.* 2008, 51, 2307-2310; Sharma, N., Mohanakrishnan, D., Shard, A., Sharma, A., Saima, Sinha, A. K. and Sahal, D. Stilbene-chalcone hybrids: design, synthesis, and evaluation as a new class of antimalarial scaffolds that trigger cell death through stage specific apoptosis. *J. Med. Chem.* 2012, 55, 297-311). A more recent reevaluation of this type of compounds by NCI against human tumor cell lines reconfirmed that, like colchicine, they are effective inhibitors of tubulin polymerization. Pyrazole (NSC-45410) is a low molecular weight, heterocyclic compound which has been considered for reevaluation in the clinic as a potential cytotoxic agent. (O'Dwyer. P J, King S A, Plowman J, Grieshaber C K, Hoth D F, Leyland-Jones B. Pyrazole: preclinical reassessment. Invest New Drugs; 1988, 6, 305-310; Sidique, S., Ardecky, R., Su, Y., Narisawa, S., Brown, B., Millan, J. L., Sergienko, E. and Cosford, N. D., Design and synthesis of pyrazole as potent and selective inhibitors of tissue-nonspecific alkaline phosphatase (TNAP). Bioorg. Med. Chem. Lett. 2009, 19, 222-225). Biochemical mechanistic studies performed with dihydropyridopyrazole ($S_3$) compounds showed that these molecules inhibit in vitro tubulin polymerization and disrupt the formation of mitotic spindles in dividing cells at low nanomolar concentrations, in a manner similar to podophyllotoxin itself (Magedov, I. V., Frolova, L., Manpadi, M., Bhoga, U. D., Tang, H., Evdokimov, N. M., George, O., Georgiou, K. H., Renner, S., Getlik, M., Kinnibrugh, T. L., Fernandes, M. A., van Slambrouck, S., Steelant, W. F. A., Shuster, C. B., Rogelj, S., van Otterlo, W. A. L. and Kornienko, A. Anticancer properties of an important drug lead podophyllotoxin can be efficiently mimicked by diverse heterocyclic scaffolds accessible via one-step synthesis. *J. Med. Chem.* 2011, 54, 4234-4246). The microtubules possesses three sites for ligand binding—the vinca domain, colchicine domain and taxol domain. However, occurrence of peripheral neuropathy, high systemic toxicity and drug resistance are major limitations in the development of antimicrotubule agents as drugs (F. Pellegrini, D. R. Budman, Tubulin function, action of antitubulin drugs, and new drug development. *Cancer. Invest.* 2005, 23, 264-273). The unique feature of microtubule-binding agents, in contrast to other categories of anticancer drugs, is their incredible structural complexity and diversity, which provides many possibilities for new scaffold design. In recent years, combination chemotherapy with agents possessing different mechanisms of action is one of the methods, that is being adopted to treat cancer. Therefore, hybrid compounds like pyrazolochalcones described in the present invention that contain pyrazole as well as chalcone pharmacophores with different mode of action could be beneficial for the treatment of cancer.

$S_1$

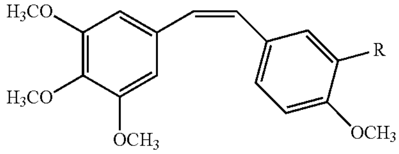

R = OH CA4
R = $OPO_3NA_2$ CA4P
R = NHSer, HCl AVE8062

$S_2$

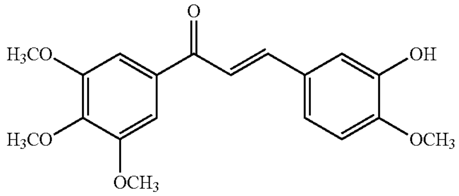

$S_3$

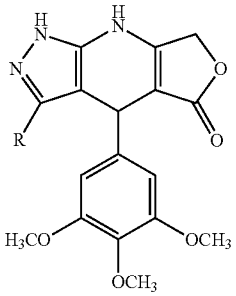

$S_4$

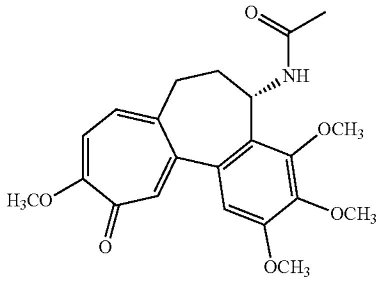

OBJECTIVES OF THE INVENTION

The main objective of the present invention is to provide pyrazolochalcones useful as antitumor agents.

Yet another object of this invention is to provide a process for the preparation of pyrazolochalcones.

Further object of the present invention is to provide novel pyrazolochalcones of formula A1 and A2 as potential anti-cancer agents.

SUMMARY OF THE INVENTION

Accordingly the present invention provides a pyrazolochalcone of formula A,

Formula A

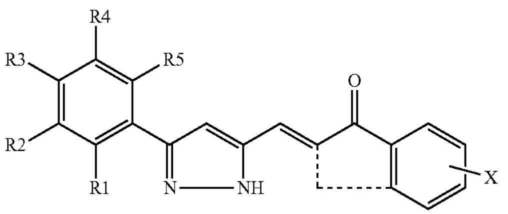

wherein,
R1, R2, R3, R4, R5=H, Cl, F, $CH_3$, $OCH_3$, 3,4($OCH_2O$)
X=H, Cl, F, $CH_3$, $OCH_3$, 3,4($OCH_2O$), $NH_2$, $NO_2$, OH.

In an embodiment of the invention the pyrazolochalcone of formula A is selected from the group consisting of pyrazolochalcone of formula A1 and pyrazolochalcone of formula A2

A1

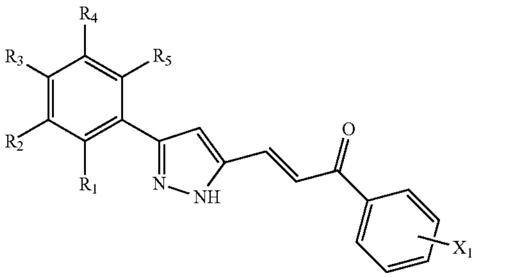

wherein,
R1, R2, R3, R4, R5=H, Cl, F, $CH_3$, $OCH_3$, 3,4($OCH_2O$)
$X_1$=H, Cl, F, $CH_3$, $OCH_3$, 3,4($OCH_2O$), $NH_2$, $NO_2$, OH.

A2

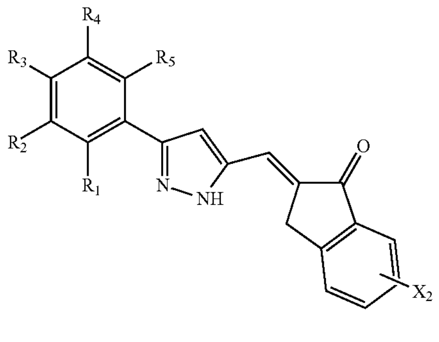

wherein,
R1, R2, R3, R4, R5=H, Cl, F, $CH_3$, $OCH_3$, 3,4($OCH_2O$)
$X_2$=H, $OCH_3$ In another embodiment of the present invention the pyrazolochalcone of formula A1 is selected from the group consisting of compounds of formulae 6a-21a, 6b-21b, 6c-21c, 6d-21d, 6e-21e, 6f-21f, 6g-21g, 6h-21h, 6i-21i, 6j-21j, 6k-21k and 6l-21l and pyrazolochalcone of formula A2 is selected from the group consisting of compounds of formulae 22a-24a, 22b-24b, 22c-24c, 22d-24d, 22e-24e, 22f-24f, 22g-24g, 22h-24h, 22i-24i, 22j-24j, 22k-24k and 22l-24l.

(6a-21a)

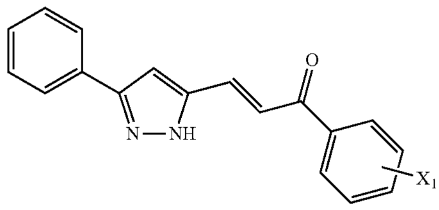

(6b-21b)

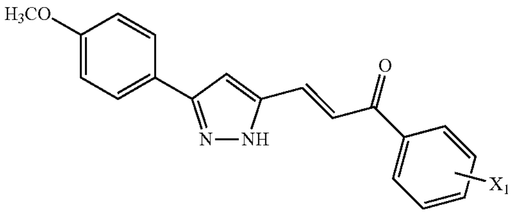

(6c-21c)

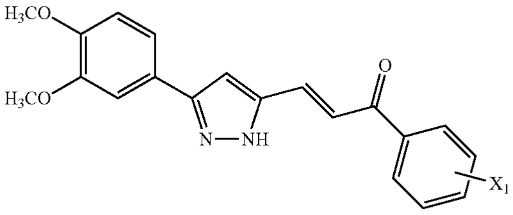

(6d-21d)

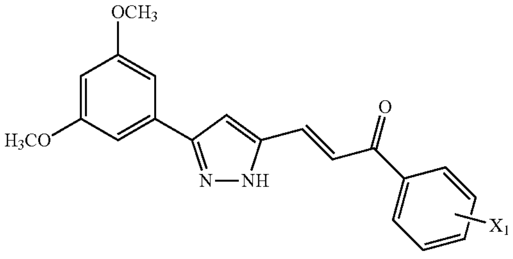

(6e-21e)

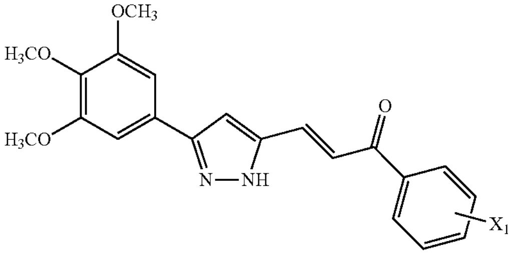

-continued
(6f-21f)
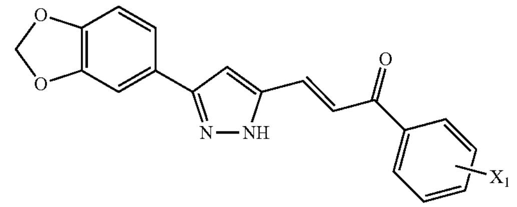
(6g21g)
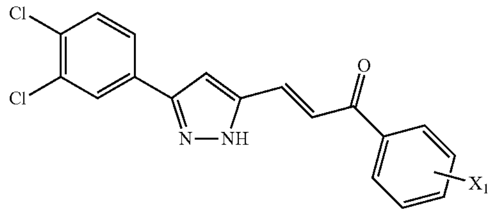
(6h-21h)
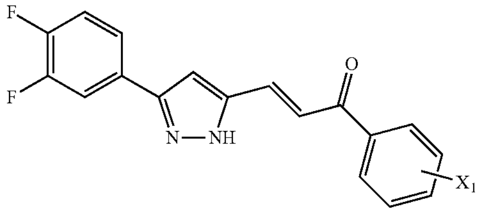
(6i-21i)
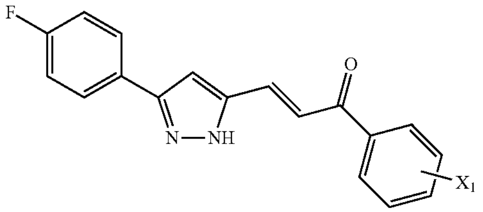
(6j-21j)
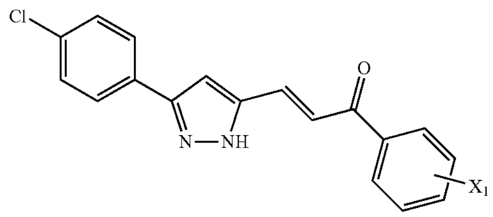
(6k-21k)
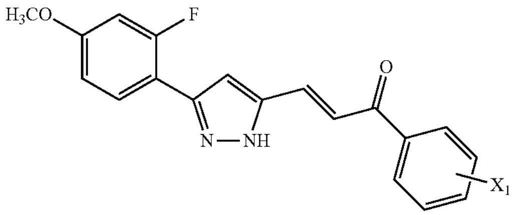
(6l-21l)
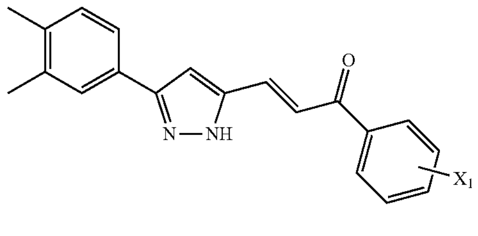
wherein $X_1$=H, Cl, F, $CH_3$, $OCH_3$, 3,4($OCH_2O$), $NH_2$, $NO_2$, OH
(22a-24a)
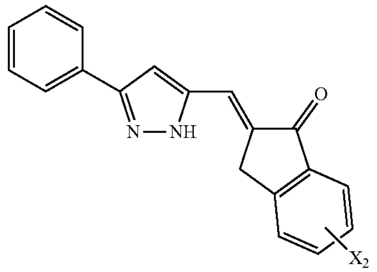
(22b-24b)
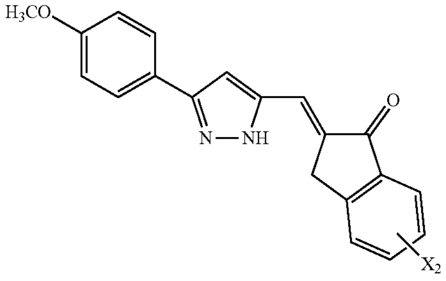
(22c-24c)
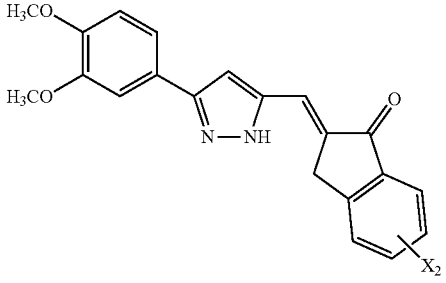
(22d-24d)
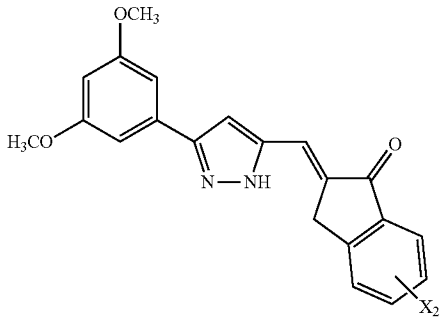
(22e-24e)
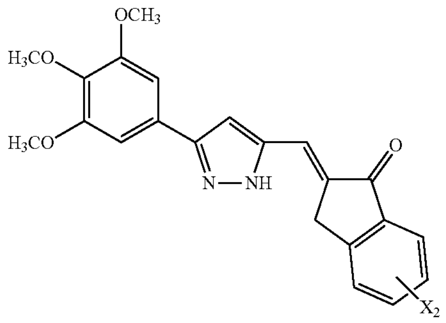

-continued (22f-24f)

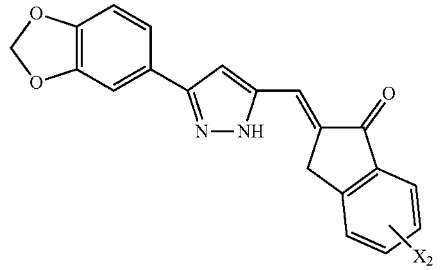

(22g-24g)

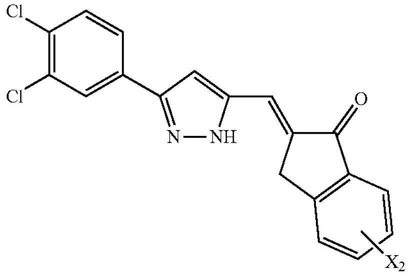

(22h-24h)

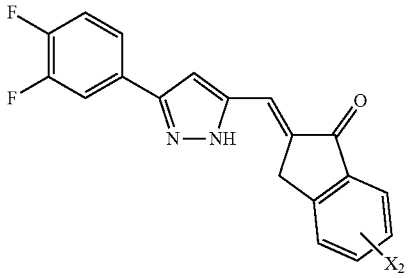

(22i-24i)

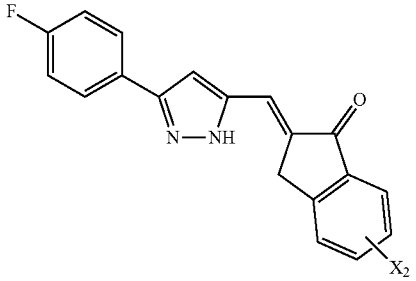

(22j-24j)

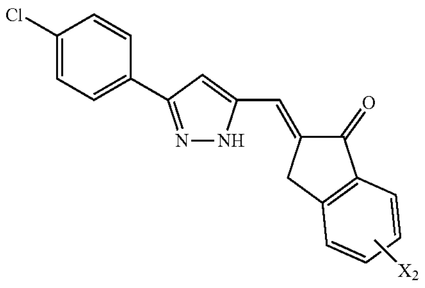

-continued (22k-24k)

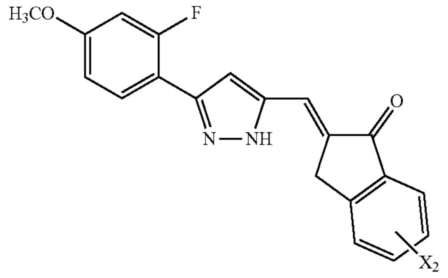

(22l-24l)

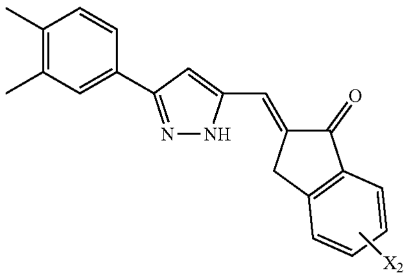

$X_2$ = H, $OCH_3$

In yet another embodiment of the invention the pyrazolochalcone of formula A is selected from the group consisting of:

(E)-1-phenyl-3-(3-phenyl-1H-pyrazol-5-yl) prop-2-en-1-one (6a);

(E)-3-(3-(4-methoxyphenyl)-1H-pyrazol-5-yl)-1-phenylprop-2-en-1-one (6b);

(E)-3-(3-(3,4-dimethoxyphenyl)-1H-pyrazol-5-yl)-1-phenylprop-2-en-1-one (6c);

(E)-3-(3-(3,5-dimethoxyphenyl)-1H-pyrazol-5-yl)-1-phenylprop-2-en-1-one (6d);

(E)-1-phenyl-3-(3-(3,4,5-trimethoxyphenyl)-1H-pyrazol-5-yl)prop-2-en-1-one (6e);

(E)-3-(3-(benzo[d][1,3]dioxol-5-yl)-1H-pyrazol-5-yl)-1-phenylprop-2-en-1-one (6f);

(E)-3-(3-(3,4-dichlorophenyl)-1H-pyrazol-5-yl)-1-phenylprop-2-en-1-one (6g);

(E)-3-(3-(3,4-difluorophenyl)-1H-pyrazol-5-yl)-1-phenylprop-2-en-1-one (6h);

(E)-3-(3-(4-fluorophenyl)-1H-pyrazol-5-yl)-1-phenylprop-2-en-1-one (6i);

(E)-3-(3-(4-chlorophenyl)-1H-pyrazol-5-yl)-1-phenylprop-2-en-1-one (6j);

(E)-3-(3-(2-fluoro-4-methoxyphenyl)-1H-pyrazol-5-yl)-1-phenylprop-2-en-1-one (6k);

(E)-3-(3-(3,4-dimethylphenyl)-1H-pyrazol-5-yl)-1-phenylprop-2-en-1-one (6l);

(E)-1-(4-methoxyphenyl)-3-(3-phenyl-1H-pyrazol-5-yl) prop-2-en-1-one (7a);

(E)-1-(4-methoxyphenyl)-3-(3-(4-methoxyphenyl)-1H-pyrazol-5-yl)prop-2-en-1-one (7b);

(E)-3-(3-(3,4-dimethoxyphenyl)-1H-pyrazol-5-yl)-1-(4-methoxyphenyl)prop-2-en-1-one (7c);

(E)-3-(3-(3,5-dimethoxyphenyl)-1H-pyrazol-5-yl)-1-(4-methoxyphenyl)prop-2-en-1-one (7d);

(E)-1-(4-methoxyphenyl)-3-(3-(3,4,5-trimethoxyphenyl)-1H-pyrazol-5-yl)prop-2-en-1-one (7e);

(E)-3-(3-(benzo[d][1,3]dioxol-5-yl)-1H-pyrazol-5-yl)-1-(4-methoxyphenyl)prop-2-en-1-one (7f);

(E)-3-(3-(3,4-dichlorophenyl)-1H-pyrazol-5-yl)-1-(4-methoxyphenyl)prop-2-en-1-one (7g);
(E)-3-(3-(3,4-difluorophenyl)-1H-pyrazol-5-yl)-1-(4-methoxyphenyl)prop-2-en-1-one (7h);
(E)-3-(3-(4-fluorophenyl)-1H-pyrazol-5-yl)-1-(4-methoxyphenyl)prop-2-en-1-one (7i);
(E)-3-(3-(4-chlorophenyl)-1H-pyrazol-5-yl)-1-(4-methoxyphenyl)prop-2-en-1-one (7i);
(E)-3-(3-(2-fluoro-4-methoxyphenyl)-1H-pyrazol-5-yl)-1-(4-methoxyphenyl)prop-2-en-1-one (7k);
(E)-3-(3-(3,4-dimethylphenyl)-1H-pyrazol-5-yl)-1-(4-methoxyphenyl)prop-2-en-1-one (7l);
(E)-1-(3,4-dimethoxyphenyl)-3-(3-phenyl-1H-pyrazol-5-yl)prop-2-en-1-one (8a);
(E)-1-(3,4-dimethoxyphenyl)-3-(3-(4-methoxyphenyl)-1H-pyrazol-5-yl)prop-2-en-1-one (8b);
(E)-1-(3,4-dimethoxyphenyl)-3-(3-(3,4-dimethoxyphenyl)-1H-pyrazol-5-yl)prop-2-en-1-one (8c);
(E)-1-(3,4-dimethoxyphenyl)-3-(3-(3,5-dimethoxyphenyl)-1H-pyrazol-5-yl)prop-2-en-1-one (8d);
(E)-1-(3,4-dimethoxyphenyl)-3-(3-(3,4,5-trimethoxyphenyl)-1H-pyrazol-5-yl)prop-2-en-1-one (8e);
(E)-3-(3-(benzo[d][1,3]dioxol-5-yl)-1H-pyrazol-5-yl)-1-(3,4-dimethoxyphenyl)prop-2-en-1-one (8f);
(E)-3-(3-(3,4-dichlorophenyl)-1H-pyrazol-5-yl)-1-(3,4-dimethoxyphenyl)prop-2-en-1-one (8g);
(E)-3-(3-(3,4-difluorophenyl)-1H-pyrazol-5-yl)-1-(3,4-dimethoxyphenyl)prop-2-en-1-one (8h);
(E)-1-(3,4-dimethoxyphenyl)-3-(3-(4-fluorophenyl)-1H-pyrazol-5-yl)prop-2-en-1-one (8i);
(E)-3-(3-(4-chlorophenyl)-1H-pyrazol-5-yl)-1-(3,4-dimethoxyphenyl)prop-2-en-1-one (8j);
(E)-1-(3,4-dimethoxyphenyl)-3-(3-(2-fluoro-4-methoxyphenyl)-1H-pyrazol-5-yl)prop-2-en-1-one (8k);
(E)-1-(3,4-dimethoxyphenyl)-3-(3-(3,4-dimethylphenyl)-1H-pyrazol-5-yl)prop-2-en-1-one (8l);
(E)-1-(3,5-dimethoxyphenyl)-3-(3-phenyl-1H-pyrazol-5-yl)prop-2-en-1-one (9a);
(E)-1-(3,5-dimethoxyphenyl)-3-(3-(4-methoxyphenyl)-1H-pyrazol-5-yl)prop-2-en-1-one (9b);
(E)-1-(3,5-dimethoxyphenyl)-3-(3-(3,4-dimethoxyphenyl)-1H-pyrazol-5-yl)prop-2-en-1-one (9c);
(E)-1-(3,5-dimethoxyphenyl)-3-(3-(3,5-dimethoxyphenyl)-1H-pyrazol-5-yl)prop-2-en-1-one (9d);
(H)-1-(3,5-dimethoxyphenyl)-3-(3-(3,4,5-trimethoxyphenyl)-1H-pyrazol-5-yl)prop-2-en-1-one (9e);
(E)-3-(3-(benzo[d][1,3]dioxol-5-yl)-1H-pyrazol-5-yl)-1-(3,5-dimethoxyphenyl)prop-2-en-1-one (9f);
(E)-3-(3-(3,4-dichlorophenyl)-1H-pyrazol-5-yl)-1-(3,5-dimethoxyphenyl)prop-2-en-1-one (9g);
(E)-3-(3-(3,4-difluorophenyl)-1H-pyrazol-5-yl)-1-(3,5-dimethoxyphenyl)prop-2-en-1-one (9h);
(E)-1-(3,5-dimethoxyphenyl)-3-(3-(4-fluorophenyl)-1H-pyrazol-5-yl)prop-2-en-1-one (9i);
(E)-3-(3-(4-chlorophenyl)-1H-pyrazol-5-yl)-1-(3,5-dimethoxyphenyl)prop-2-en-1-one (9j);
(E)-1-(3,5-dimethoxyphenyl)-3-(3-(2-fluoro-4-methoxyphenyl)-1H-pyrazol-5-yl)prop-2-en-1-one (9k);
(E)-1-(3,5-dimethoxyphenyl)-3-(3-(3,4-dimethylphenyl)-1H-pyrazol-5-yl)prop-2-en-1-one (9l);
(E)-3-(3-phenyl-1 FI-pyrazol-5-yl)-1-(3,4,5-trimethoxyphenyl)prop-2-en-1-one (10a);
(E)-3-(3-(4-methoxyphenyl)-1H-pyrazol-5-yl)-1-(3,4,5-trimethoxyphenyl)prop-2-en-1-one (10b);
(E)-3-(3-(3,4-dimethoxyphenyl)-1H-pyrazol-5-yl)-1-(3,4,5-trimethoxyphenyl)prop-2-en-1-one (10c);
(E)-3-(3-(3,5-dimethoxyphenyl)-1H-pyrazol-5-yl)-1-(3,4,5-trimethoxyphenyl)prop-2-en-1-one (10d);
(E)-1-(3,4,5-trimethoxyphenyl)-3-(3-(3,4,5-trimethoxyphenyl)-1H-pyrazol-5-yl)prop-2-en-1-one (10e);
(E)-3-(3-(benzo[d][1,3]dioxol-5-yl)-1H-pyrazol-5-yl)-1-(3,4,5-trimethoxyphenyl)prop-2-en-1-one (10f);
(E)-3-(3-(3,4-dichlorophenyl)-1H-pyrazol-5-yl)-1-(3,4,5-trimethoxyphenyl)prop-2-en-1-one (10g);
(E)-3-(3-(3,4-difluorophenyl)-1H-pyrazol-5-yl)-1-(3,4,5-trimethoxyphenyl)prop-2-en-1-one (10h);
(E)-3-(3-(4-fluorophenyl)-1H-pyrazol-5-yl)-1-(3,4,5-trimethoxyphenyl)prop-2-en-1-one (10i);
(E)-3-(3-(4-chlorophenyl)-1H-pyrazol-5-yl)-1-(3,4,5-trimethoxyphenyl)prop-2-en-1-one (10j);
(E)-3-(3-(2-fluoro-4-methoxyphenyl)-1H-pyrazol-5-yl)-1-(3,4,5-trimethoxyphenyl)prop-2-en-1-one (10k);
(E)-3-(3-(3,4-dimethylphenyl)-1H-pyrazol-5-yl)-1-(3,4,5-trimethoxyphenyl)prop-2-en-1-one (10l);
(E)-1-(benzo[d][1,3]dioxol-5-yl)-3-(3-phenyl-1H-pyrazol-5-yl)prop-2-en-1-one (11a);
(E)-1-(benzo[d][1,3]dioxol-5-yl)-3-(3-(4-methoxyphenyl)-1H-pyrazol-5-yl)prop-2-en-1-one (11b);
(E)-1-(benzo[d][1,3]dioxol-5-yl)-3-(3-(3,4-dimethoxyphenyl)-1H-pyrazol-5-yl)prop-2-en-1-one (11c);
(E)-1-(benzo[d][1,3]dioxol-5-yl)-3-(3-(3,5-dimethoxyphenyl)-1H-pyrazol-5-yl)prop-2-en-1-one (11d);
(E)-1-(benzo[d][1,3]dioxol-5-yl)-3-(3-(3,4, 5-trimethoxyphenyl)-1H-pyrazol-5-yl)prop-2-en-1-one (11e);
(E)-1-(benzo[d][1,3]dioxol-5-yl)-3-(3-(benzo[d][1,3]dioxol-5-yl)-1H-pyrazol-5-yl)prop-2-en-1-one (11f);
(E)-1-(benzo[d][1,3]dioxol-5-yl)-3-(3-(3,4-dichlorophenyl)-1H-pyrazol-5-yl)prop-2-en-1-one (11g);
(E)-1-(benzo[d][1,3]dioxol-5-yl)-3-(3-(3,4-difluorophenyl)-1H-pyrazol-5-yl)prop-2-en-1-one (11h);
(E)-1-(benzo[d][1,3]dioxol-5-yl)-3-(3-(4-fluorophenyl)-1H-pyrazol-5-yl)prop-2-en-1-one (11i);
(E)-1-(benzo[d][1,3]dioxol-5-yl)-3-(3-(4-chlorophenyl)-1H-pyrazol-5-yl)prop-2-en-1-one (11j);
(E)-1-(benzo[d][1,3]dioxol-5-yl)-3-(3-(2-fluoro-4-methoxyphenyl)-1H-pyrazol-5-yl)prop-2-en-1-one (11k);
(E)-1-(benzo[d][1,3]dioxol-5-yl)-3-(3-(3,4-dimethylphenyl)-1H-pyrazol-5-yl)prop-2-en-1-one (11l);
(E)-1-(3,4-dichlorophenyl)-3-(3-phenyl-1H-pyrazol-5-yl)prop-2-en-1-one (12a);
(E)-1-(3,4-dichlorophenyl)-3-(3-(4-methoxyphenyl)-1H-pyrazol-5-yl)prop-2-en-1-one (12b);
(E)-1-(3,4-dichlorophenyl)-3-(3-(3,4-dimethoxyphenyl)-1H-pyrazol-5-yl)prop-2-en-1-one (12c);
(E)-1-(3,4-dichlorophenyl)-3-(3-(3,5-dimethoxyphenyl)-1H-pyrazol-5-yl)prop-2-en-1-one (12d);
(E)-1-(3,4-dichlorophenyl)-3-(3-(3,4,5-trimethoxyphenyl)-1H-pyrazol-5-yl)prop-2-en-1-one (12e);
(E)-3-(3-(benzo[d][1,3]dioxol-5-yl)-1H-pyrazol-5-yl)-1-(3,4-dichlorophenyl)prop-2-en-1-one (12f);
(E)-1-(3,4-dichlorophenyl)-3-(3-(3,4-dichlorophenyl)-1H-pyrazol-5-yl)prop-2-en-1-one (12g);
(E)-1-(3,4-dichlorophenyl)-3-(3-(3,4-difluorophenyl)-1H-pyrazol-5-yl)prop-2-en-1-one (12h);
(E)-1-(3,4-dichlorophenyl)-3-(3-(4-fluorophenyl)-1H-pyrazol-5-yl)prop-2-en-1-one (12i);
(E)-3-(3-(4-chlorophenyl)-1H-pyrazol-5-yl)-1-(3,4-dichlorophenyl)prop-2-en-1-one (12j);
(E)-1-(3,4-dichlorophenyl)-3-(3-(2-fluoro-4-methoxyphenyl)-1H-pyrazol-5-yl)prop-2-en-1-one (12k);
(E)-1-(3,4-dichlorophenyl)-3-(3-(3,4-dimethylphenyl)-1H-pyrazol-5-yl)prop-2-en-1-one (12l);

(E)-1-(3,4-difluorophenyl)-3-(3-phenyl-1H-pyrazol-5-yl)prop-2-en-1-one (13a);

(E)-1-(3,4-difluorophenyl)-3-(3-(4-methoxyphenyl)-1H-pyrazol-5-yl)prop-2-en-1-one (13b);

(E)-1-(3,4-difluorophenyl)-3-(3-(3,4-dimethoxyphenyl)-1H-pyrazol-5-yl)prop-2-en-1-one (13c);

(E)-1-(3,4-difluorophenyl)-3-(3-(3,5-dimethoxyphenyl)-1H-pyrazol-5-yl)prop-2-en-1-one (13d);

(E)-1-(3,4-difluorophenyl)-3-(3-(3,4,5-trimethoxyphenyl)-1H-pyrazol-5-yl)prop-2-en-1-one (13e);

(E)-3-(3-(benzo[d][1,3]dioxol-5-yl)-1H-pyrazol-5-yl)-1-(3,4-difluorophenyl)prop-2-en-1-one (13f);

(E)-3-(3-(3,4-dichlorophenyl)-1H-pyrazol-5-yl)-1-(3,4-difluorophenyl)prop-2-en-1-one (13g);

(E)-1-(3,4-difluorophenyl)-3-(3-(3,4-difluorophenyl)-1H-pyrazol-5-yl)prop-2-en-1-one (13h);

(E)-1-(3,4-difluorophenyl)-3-(3-(4-fluorophenyl)-1H-pyrazol-5-yl)prop-2-en-1-one (13i);

(E)-3-(3-(4-chlorophenyl)-1H-pyrazol-5-yl)-1-(3,4-difluorophenyl)prop-2-en-1-one (13j);

(E)-1-(3,4-difluorophenyl)-3-(3-(2-fluoro-4-methoxyphenyl)-1H-pyrazol-5-yl)prop-2-en-1-one (13k);

(E)-1-(3,4-difluorophenyl)-3-(3-(3,4-dimethylphenyl)-1H-pyrazol-5-yl)prop-2-en-1-one (13l);

(E)-1-(4-fluorophenyl)-3-(3-phenyl-1H-pyrazol-5-yl)prop-2-en-1-one (14a);

(E)-1-(4-fluorophenyl)-3-(3-(4-methoxyphenyl)-1H-pyrazol-5-yl)prop-2-en-1-one (14b);

(E)-3-(3-(3,4-dimethoxyphenyl)-1H-pyrazol-5-yl)-1-(4-fluorophenyl)prop-2-en-1-one (14c);

(E)-3-(3-(3,5-dimethoxyphenyl)-1H-pyrazol-5-yl)-1-(4-fluorophenyl)prop-2-en-1-one (14d);

(E)-1-(4-fluorophenyl)-3-(3-(3,4,5-trimethoxyphenyl)-1H-pyrazol-5-yl)prop-2-en-1-one (14e);

(E)-3-(3-(benzo[d][1,3]dioxol-5-yl)-1H-pyrazol-5-yl)-1-(4-fluorophenyl)prop-2-en-1-one (14f);

(E)-3-(3-(3,4-dichlorophenyl)-1H-pyrazol-5-yl)-1-(4-fluorophenyl)prop-2-en-1-one (14g);

(E)-3-(3-(3,4-difluorophenyl)-1H-pyrazol-5-yl)-1-(4-fluorophenyl)prop-2-en-1-one (14h);

(E)-1-(4-fluorophenyl)-3-(3-(4-fluorophenyl)-1H-pyrazol-5-yl)prop-2-en-1-one (14i);

(E)-3-(3-(4-chlorophenyl)-1H-pyrazol-5-yl)-1-(4-fluorophenyl)prop-2-en-1-one (14j);

(E)-3-(3-(2-fluoro-4-methoxyphenyl)-1H-pyrazol-5-yl)-1-(4-fluorophenyl)prop-2-en-1-one (14k);

(E)-3-(3-(3,4-dimethylphenyl)-1H-pyrazol-5-yl)-1-(4-fluorophenyl)prop-2-en-1-one (14l);

(E)-1-(4-chlorophenyl)-3-(3-phenyl-1H-pyrazol-5-yl)prop-2-en-1-one (15a);

(E)-1-(4-chlorophenyl)-3-(3-(4-methoxyphenyl)-1H-pyrazol-5-yl)prop-2-en-1-one (15b);

(E)-1-(4-chlorophenyl)-3-(3-(3,4-dimethoxyphenyl)-1H-pyrazol-5-yl)prop-2-en-1-one (15c);

(E)-1-(4-chlorophenyl)-3-(3-(3,5-dimethoxyphenyl)-1H-pyrazol-5-yl)prop-2-en-1-one (15d);

(E)-1-(4-chlorophenyl)-3-(3-(3,4,5-trimethoxyphenyl)-1H-pyrazol-5-yl)prop-2-en-1-one (15e);

(E)-3-(3-(benzo[d][1,3]dioxol-5-yl)-1H-pyrazol-5-yl)-1-(4-chlorophenyl)prop-2-en-1-one (150;

(E)-1-(4-chlorophenyl)-3-(3-(3,4-dichlorophenyl)-1H-pyrazol-5-yl)prop-2-en-1-one (15g);

(E)-1-(4-chlorophenyl)-3-(3-(3,4-difluorophenyl)-1H-pyrazol-5-yl)prop-2-en-1-one (15h);

(E)-1-(4-chlorophenyl)-3-(3-(4-fluorophenyl)-1H-pyrazol-5-yl)prop-2-en-1-one (15i);

(E)-1-(4-chlorophenyl)-3-(3-(4-chlorophenyl)-1H-pyrazol-5-yl)prop-2-en-1-one (15j);

(E)-1-(4-chlorophenyl)-3-(3-(2-fluoro-4-methoxyphenyl)-1H-pyrazol-5-yl)prop-2-en-1-one (15k);

(E)-1-(4-chlorophenyl)-3-(3-(3,4-dimethylphenyl)-1H-pyrazol-5-yl)prop-2-en-1-one (15l);

(E)-1-(2-fluoro-4-methoxyphenyl)-3-(3-phenyl-1H-pyrazol-5-yl)prop-2-en-1-one (16a);

(E)-1-(2-fluoro-4-methoxyphenyl)-3-(3-(4-methoxyphenyl)-1H-pyrazol-5-yl)prop-2-en-1-one (16b);

(E)-3-(3-(3,4-dimethoxyphenyl)-1H-pyrazol-5-yl)-1-(2-fluoro-4-methoxyphenyl)prop-2-en-1-one (16c);

(E)-3-(3-(3,5-dimethoxyphenyl)-1H-pyrazol-5-yl)-1-(2-fluoro-4-methoxyphenyl)prop-2-en-1-one (16d);

(E)-1-(2-fluoro-4-methoxyphenyl)-3-(3-(3,4,5-trimethoxyphenyl)-1H-pyrazol-5-yl)prop-2-en-1-one (16e);

(E)-3-(3-(benzo[d][1,3]dioxol-5-yl)-1H-pyrazol-5-yl)-1-(2-fluoro-4-methoxyphenyl)prop-2-en-1-one (16f);

(E)-3-(3-(3,4-dichlorophenyl)-1H-pyrazol-5-yl)-1-(2-fluoro-4-methoxyphenyl)prop-2-en-1-one (16g);

(E)-3-(3-(3,4-difluorophenyl)-1H-pyrazol-5-yl)-1-(2-fluoro-4-methoxyphenyl)prop-2-en-1-one (16h);

(E)-1-(2-fluoro-4-methoxyphenyl)-3-(3-(4-fluorophenyl)-1H-pyrazol-5-yl)prop-2-en-1-one (16i);

(E)-3-(3-(4-chlorophenyl)-1H-pyrazol-5-yl)-1-(2-fluoro-4-methoxyphenyl)prop-2-en-1-one (16j);

1-(2-fluoro-4-methoxyphenyl)-3-(3-(2-fluoro-4-methoxyphenyl)-1H-pyrazol-5-yl)prop-2-en-1-one (16k);

(E)-3-(3-(3,4-dimethylphenyl)-1H-pyrazol-5-yl)-1-(2-fluoro-4-methoxyphenyl)prop-2-en-1-one (16l);

(E)-1-(3,4-dimethylphenyl)-3-(3-phenyl-1H-pyrazol-5-yl)prop-2-en-1-one (17a);

(E)-1-(3,4-dimethylphenyl)-3-(3-(4-methoxyphenyl)-1H-pyrazol-5-yl)prop-2-en-1-one (17b);

(E)-3-(3-(3,4-dimethoxyphenyl)-1H-pyrazol-5-yl)-1-(3,4-dimethylphenyl)prop-2-en-1-one (17c);

(E)-3-(3-(3,5-dimethoxyphenyl)-1H-pyrazol-5-yl)-1-(3,4-dimethylphenyl)prop-2-en-1-one (17d);

(E)-1-(3,4-dimethylphenyl)-3-(3-(3,4,5-trimethoxyphenyl)-1H-pyrazol-5-yl)prop-2-en-1-one (17e);

(E)-3-(3-(benzo[d][1,3]dioxol-5-yl)-1H-pyrazol-5-yl)-1-(3,4-dimethylphenyl)prop-2-en-1-one (17f);

(E)-3-(3-(3,4-difluorophenyl)-1H-pyrazol-5-yl)-1-(3,4-dimethylphenyl)prop-2-en-1-one (17g);

(E)-3-(3-(3,4-dichlorophenyl)-1H-pyrazol-5-yl)-1-(3,4-dimethylphenyl)prop-2-en-1-one (17h);

(E)-1-(3,4-dimethylphenyl)-3-(3-(4-fluorophenyl)-1H-pyrazol-5-yl)prop-2-en-1-one (17i);

(E)-3-(3-(4-chlorophenyl)-1H-pyrazol-5-yl)-1-(3,4-dimethylphenyl)prop-2-en-1-one (17j);

1-(3,4-dimethylphenyl)-3-(3-(2-fluoro-4-methoxyphenyl)-1H-pyrazol-5-yl)prop-2-en-1-one (17k);

(E)-1-(3,4-dimethylphenyl)-3-(3-(3,4-dimethylphenyl)-1H-pyrazol-5-yl)prop-2-en-1-one (17l);

(E)-1-(3-hydroxy-4-methoxyphenyl)-3-(3-phenyl-1H-pyrazol-5-yl)prop-2-en-1-one (18a);

(E)-1-(3-hydroxy-4-methoxyphenyl)-3-(3-(4-methoxyphenyl)-1H-pyrazol-5-yl)prop-2-en-1-one (18b);

(E)-3-(3-(3,4-dimethoxyphenyl)-1H-pyrazol-5-yl)-1-(3-hydroxy-4-methoxyphenyl)prop-2-en-1-one (18c);

(E)-3-(3-(3,5-dimethoxyphenyl)-1H-pyrazol-5-yl)-1-(3-hydroxy-4-methoxyphenyl)prop-2-en-1-one (18d);

(E)-1-(3-hydroxy-4-methoxyphenyl)-3-(3-(3,4,5-trimethoxyphenyl)-1H-pyrazol-5-yl)prop-2-en-1-one (18e);

(E)-3-(3-(benzo[d][1,3]dioxol-5-yl)-1H-pyrazol-5-yl)-1-(3-hydroxy-4-methoxyphenyl)prop-2-en-1-one (18f);
(E)-3-(3-(3,4-dichlorophenyl)-1H-pyrazol-5-yl)-1-(3-hydroxy-4-methoxyphenyl)prop-2-en-1-one (18g);
(E)-3-(3-(3,4-difluorophenyl)-1H-pyrazol-5-yl)-1-(3-hydroxy-4-methoxyphenyl)prop-2-en-1-one (18h);
(E)-3-(3-(4-fluorophenyl)-1H-pyrazol-5-yl)-1-(3-hydroxy-4-methoxyphenyl)prop-2-en-1-one (18i);
(E)-3-(3-(4-chlorophenyl)-1H-pyrazol-5-yl)-1-(3-hydroxy-4-methoxyphenyl)prop-2-en-1-one (18j);
(E)-3-(3-(2-fluoro-4-methoxyphenyl)-1H-pyrazol-5-yl)-1-(3-hydroxy-4-methoxyphenyl)prop-2-en-1-one (18k);
(E)-3-(3-(3,4-dimethylphenyl)-1H-pyrazol-5-yl)-1-(3-hydroxy-4-methoxyphenyl)prop-2-en-1-one (18l);
(E)-1-(4-aminophenyl)-3-(3-phenyl-1H-pyrazol-5-yl)prop-2-en-1-one (19a);
(E)-1-(4-aminophenyl)-3-(3-(4-methoxyphenyl)-1H-pyrazol-5-yl)prop-2-en-1-one (19b);
(E)-1-(4-aminophenyl)-3-(3-(3,4-dimethoxyphenyl)-1H-pyrazol-5-yl)prop-2-en-1-one (19c);
(E)-1-(4-aminophenyl)-3-(3-(3,5-dimethoxyphenyl)-1H-pyrazol-5-yl)prop-2-en-1-one (19d);
(E)-1-(4-aminophenyl)-3-(3-(3,4,5-trimethoxyphenyl)-1H-pyrazol-5-yl)prop-2-en-1-one (19e);
(E)-1-(4-aminophenyl)-3-(3-(benzo[d][1,3]dioxol-5-yl)-1H-pyrazol-5-yl)prop-2-en-1-one (19f);
(E)-1-(4-aminophenyl)-3-(3-(3,4-dichlorophenyl)-1H-pyrazol-5-yl)prop-2-en-1-one (19g);
(E)-1-(4-aminophenyl)-3-(3-(3,4-difluorophenyl)-1H-pyrazol-5-yl)prop-2-en-1-one (19h);
(E)-1-(4-aminophenyl)-3-(3-(4-fluorophenyl)-1H-pyrazol-5-yl)prop-2-en-1-one (19i);
(E)-1-(4-aminophenyl)-3-(3-(4-chlorophenyl)-1H-pyrazol-5-yl)prop-2-en-1-one (19j);
(E)-1-(4-aminophenyl)-3-(3-(2-fluoro-4-methoxyphenyl)-1H-pyrazol-5-yl)prop-2-en-1-one (19k);
(E)-1-(4-aminophenyl)-3-(3-(3,4-dimethylphenyl)-1H-pyrazol-5-yl)prop-2-en-1-one (19l);
(E)-3-(3-phenyl-1H-pyrazol-5-yl)-1-p-tolylprop-2-en-1-one (20a);
(E)-3-(3-(4-methoxyphenyl)-1H-pyrazol-5-yl)-1-p-tolylprop-2-en-1-one (20b);
(E)-3-(3-(3,4-dimethoxyphenyl)-1H-pyrazol-5-yl)-1-p-tolylprop-2-en-1-one (20c);
(E)-3-(3-(3,5-dimethoxyphenyl)-1H-pyrazol-5-yl)-1-p-tolylprop-2-en-1-one (20d);
(E)-1-p-tolyl-3-(3-(3,4,5-trimethoxyphenyl)-1H-pyrazol-5-yl)prop-2-en-1-one (20e);
(E)-3-(3-(benzo[d][1,3]dioxol-5-yl)-1H-pyrazol-5-yl)-1-p-tolylprop-2-en-1-one (20f);
(E)-3-(3-(3,4-dichlorophenyl)-1H-pyrazol-5-yl)-1-p-tolylprop-2-en-1-one (20g);
(E)-3-(3-(3,4-difluorophenyl)-1H-pyrazol-5-yl)-1-p-tolylprop-2-en-1-one (20h);
(E)-3-(3-(4-fluorophenyl)-1H-pyrazol-5-yl)-1-p-tolylprop-2-en-1-one (20i);
(E)-3-(3-(4-chlorophenyl)-1H-pyrazol-5-yl)-1-p-tolylprop-2-en-1-one (20j);
(E)-3-(3-(2-fluoro-4-methoxyphenyl)-1H-pyrazol-5-yl)-1-p-tolylprop-2-en-1-one (20k);
(E)-3-(3-(3,4-dimethylphenyl)-1H-pyrazol-5-yl)-1-p-tolylprop-2-en-1-one (20l);
(E)-1-(3-chloro-4-nitrophenyl)-3-(3-phenyl-1H-pyrazol-5-yl)prop-2-en-1-one (21a);
(E)-1-(3-chloro-4-nitrophenyl)-3-(3-(4-methoxyphenyl)-1H-pyrazol-5-yl)prop-2-en-1-one (21b);
(E)-1-(3-chloro-4-nitrophenyl)-3-(3-(3,4-dimethoxyphenyl)-1H-pyrazol-5-yl)prop-2-en-1-one (21c);
(E)-1-(3-chloro-4-nitrophenyl)-3-(3-(3,5-dimethoxyphenyl)-1H-pyrazol-5-yl)prop-2-en-1-one (21d);
(E)-1-(3-chloro-4-nitrophenyl)-3-(3-(3,4,5-trimethoxyphenyl)-1H-pyrazol-5-yl)prop-2-en-1-one (21e);
(E)-3-(3-(benzo[d][1,3]dioxol-5-yl)-1H-pyrazol-5-yl)-1-(3-chloro-4-nitrophenyl)prop-2-en-1-one (21f);
(E)-1-(3-chloro-4-nitrophenyl)-3-(3-(3,4-dichlorophenyl)-1H-pyrazol-5-yl)prop-2-en-1-one (21g);
(E)-1-(3-chloro-4-nitrophenyl)-3-(3-(3,4-difluorophenyl)-1H-pyrazol-5-yl)prop-2-en-1-one (21h);
(E)-1-(3-chloro-4-nitrophenyl)-3-(3-(4-fluorophenyl)-1H-pyrazol-5-yl)prop-2-en-1-one (21i);
(E)-1-(3-chloro-4-nitrophenyl)-3-(3-(4-chlorophenyl)-1H-pyrazol-5-yl)prop-2-en-1-one (21j);
(E)-1-(3-chloro-4-nitrophenyl)-3-(3-(2-fluoro-4-methoxyphenyl)-1H-pyrazol-5-yl)prop-2-en-1-one (21k);
(E)-1-(3-chloro-4-nitrophenyl)-3-(3-(3,4-dimethylphenyl)-1H-pyrazol-5-yl)prop-2-en-1-one (21l);
(E)-2-((3-phenyl-1H-pyrazol-5-yl)methylene)-2,3-dihydro-1H-inden-1-one (22a);
(E)-2-((3-(4-methoxyphenyl)-1H-pyrazol-5-yl)methylene)-2,3-dihydro-1H-inden-1-one (22b);
(E)-2-((3-(3,4-dimethoxyphenyl)-1H-pyrazol-5-yl)methylene)-2,3-dihydro-1H-inden-1-one (22c);
(E)-2-((3-(3,5-dimethoxyphenyl)-1H-pyrazol-5-yl)methylene)-2,3-dihydro-1H-inden-1-one (22d);
(E)-2-((3-(3,4,5-trimethoxyphenyl)-1H-pyrazol-5-yl)methylene)-2,3-dihydro-1H-inden-1-one (22e);
(E)-2-((3-(benzo[d][1,3]dioxol-5-yl)-1H-pyrazol-5-yl) methylene)-2,3-dihydro-1H-inden-1-one (22f);
(E)-2-((3 chlorophenyl)-1H-pyrazol-5-yl)methylene)-2,3-dihydro-1H-inden-1-one (22g);
(E)-2-((3-(3,4-difluorophenyl)-1H-pyrazol-5-yl)methylene)-2,3-dihydro-1H-inden-1-one (22h);
(E)-2-((3-(4-fluorophenyl)-1H-pyrazol-5-yl)methylene)-2,3-dihydro-1H-inden-1-one (22i);
(E)-2-((3-(4-chlorophenyl)-1H-pyrazol-5-yl)methylene)-2,3-dihydro-1H-inden-1-one (22j);
(E)-2-((3-(2-fluoro-4-methoxyphenyl)-1H-pyrazol-5-yl) methylene)-2,3-dihydro-1H-inden-1-one (22k);
(E)-2-((3-(3,4-dimethylphenyl)-1H-pyrazol-5-yl)methylene)-2,3-dihydro-1H-inden-1-one (22l);
(E)-5-methoxy-2-((3-phenyl-1H-pyrazol-5-yl)methylene)-2,3-dihydro-1H-inden-1-one (23a);
(E)-5-methoxy-2-((3-(4-methoxyphenyl)-1H-pyrazol-5-yl) methylene)-2,3-dihydro-1H-inden-1-one (23b);
(E)-2-((3-(3,4-dimethoxyphenyl)-1H-pyrazol-5-yl)methylene)-5-methoxy-2,3-dihydro-1H-inden-1-one (23c);
(E)-2-((3-(3,5-dimethoxyphenyl)-1H-pyrazol-5-yl)methylene)-5-methoxy-2,3-dihydro-1H-inden-1-one (23d);
(E)-5-methoxy-2-((3-(3,4,5-trimethoxyphenyl)-1H-pyrazol-5-yl)methylene)-2,3-dihydro-1H-inden-1-one (23e);
(E)-2-((3-(benzo[d][1,3]dioxol-5-yl)-1H-pyrazol-5-yl) methylene)-5-methoxy-2,3-dihydro-1H-inden-1-one (23f);
(E)-2-((3-(3,4-dichlorophenyl)-1H-pyrazol-5-yl)methylene)-5-methoxy-2,3-dihydro-1H-inden-1-one (23g);
(E)-2-((3-(3,4-difluorophenyl)-1H-pyrazol-5-yl)methylene)-5-methoxy-2,3-dihydro-1H-inden-1-one (23h);
(E)-2-((3-(4-fluorophenyl)-1H-pyrazol-5-yl)methylene)-5-methoxy-2,3-dihydro-1H-inden-1-one (23i);
(E)-2-((3-(4-chlorophenyl)-1H-pyrazol-5-yl)methylene)-5-methoxy-2,3-dihydro-1H-inden-1-one (23j);

(E)-2-((3-(2-fluoro-4-methoxyphenyl)-1H-pyrazol-5-yl)methylene)-5-methoxy-2,3-dihydro-1H-inden-1-one (23k);

(E)-2-((3-(3,4-dimethylphenyl)-1H-pyrazol-5-yl)methylene)-5-methoxy-2,3-dihydro-1H-inden-1-one (23l);

(E)-5,6-dimethoxy-2-((3-phenyl-1H-pyrazol-5-yl)methylene)-2,3-dihydro-1H-inden-1-one (24a);

(E)-5,6-dimethoxy-2-((3-(4-methoxyphenyl)-1H-pyrazol-5-yl)methylene)-2,3-dihydro-1H-inden-1-one (24b);

(E)-2-((3-(3,4-dimethoxyphenyl)-1H-pyrazol-5-yl)methylene)-5,6-dimethoxy-2,3-dihydro-1H-inden-1-one (24c);

(E)-2-((3-(3,5-dimethoxyphenyl)-1H-pyrazol-5-yl)methylene)-5,6-dimethoxy-2,3-dihydro-1H-inden-1-one (24d);

(E)-5,6-dimethoxy-2-((3-(3,4,5-trimethoxyphenyl)-1H-pyrazol-5-yl)methylene)-2,3-dihydro-1H-inden-1-one (24e);

(E)-2-((3-(benzo[d][1,3]dioxol-5-yl)-1H-pyrazol-5-yl)methylene)-5,6-dimethoxy-2,3-dihydro-1H-inden-1-one (24f);

(E)-2-((3-(3,4-dichlorophenyl)-1H-pyrazol-5-yl)methylene)-5,6-dimethoxy-2,3-dihydro-1H-inden-1-one (24g);

(E)-2-((3-(3,4-difluorophenyl)-1H-pyrazol-5-yl)methylene)-5,6-dimethoxy-2,3-dihydro-1H-inden-1-one (24h);

(E)-2-((3-(4-fluorophenyl)-1H-pyrazol-5-yl)methylene)-5,6-dimethoxy-2,3-dihydro-1H-inden-1-one (24i);

(E)-2-((3-(4-chlorophenyl)-1H-pyrazol-5-yl)methylene)-5,6-dimethoxy-2,3-dihydro-1H-inden-1-one (24j);

(E)-2-((3-(2-fluoro-4-methoxyphenyl)-1H-pyrazol-5-yl)methylene)-5,6-dimethoxy-2,3-dihydro-1H-inden-1-one (24k); and (E)-2-((3-(3,4-dimethylphenyl)-1H-pyrazol-5-yl)methylene)-5,6-dimethoxy-2,3-dihydro-1H-inden-1-one (24l).

The pyrazolochalcone of formula A is selected from the group consisting of:

6a

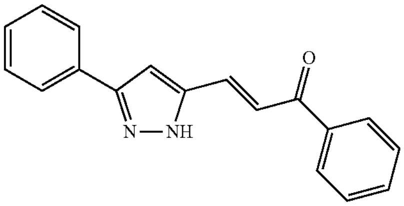

;

6b

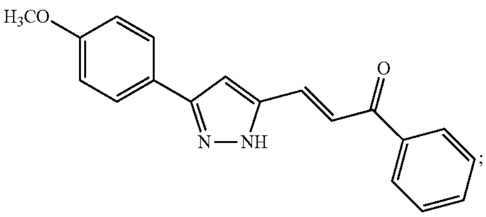

;

6c

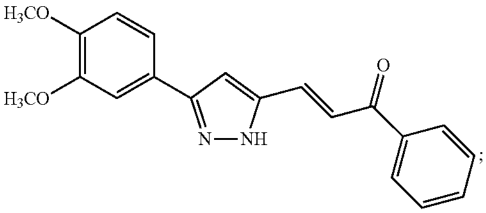

;

-continued

6d

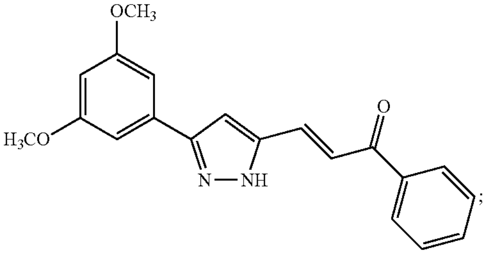

;

6e

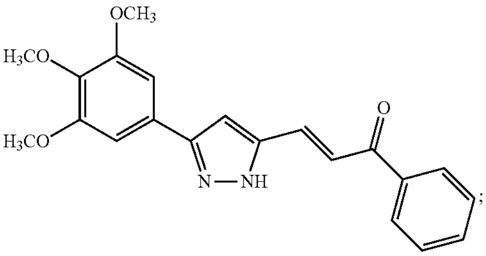

;

6f

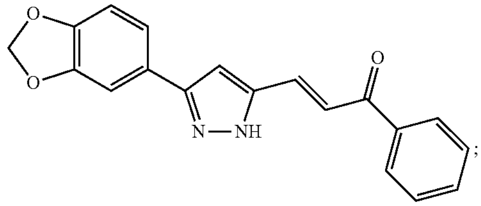

;

6g

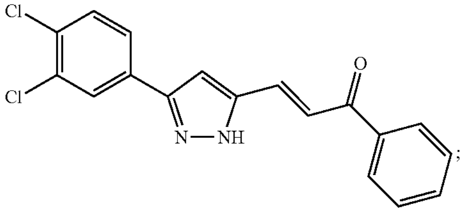

;

6h

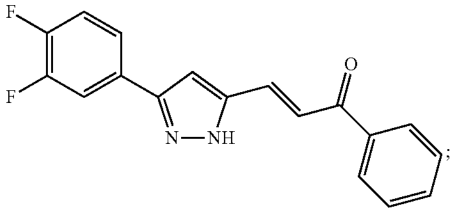

;

6i

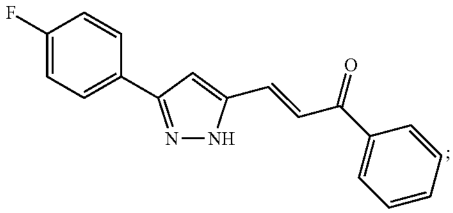

;

6j

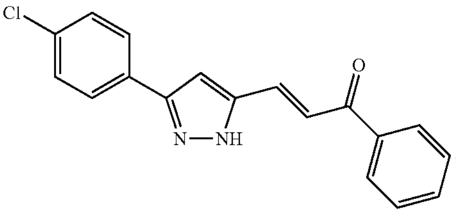

;

-continued
6k
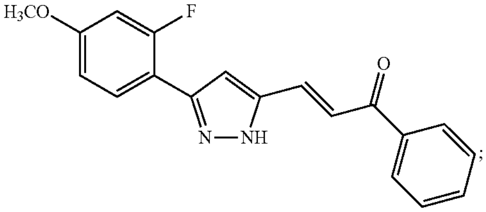
6l
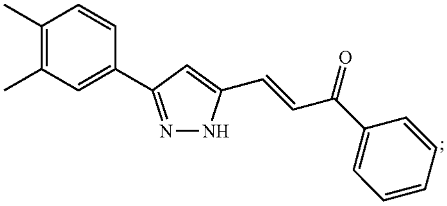
7a
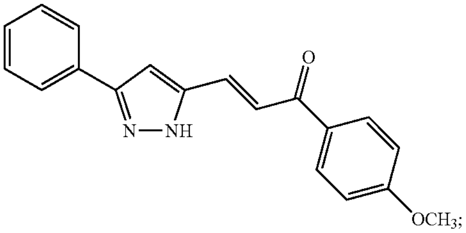
7b
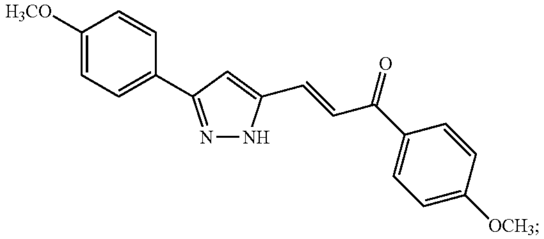
7c
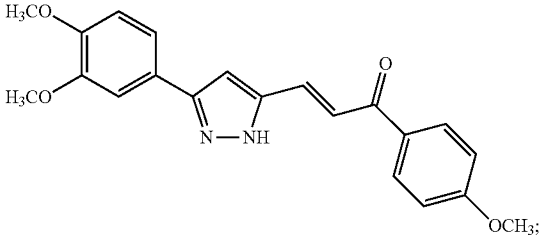
7d
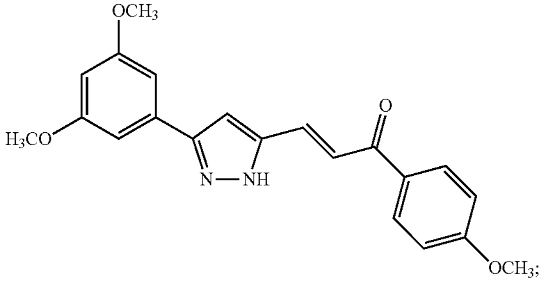
-continued
7e
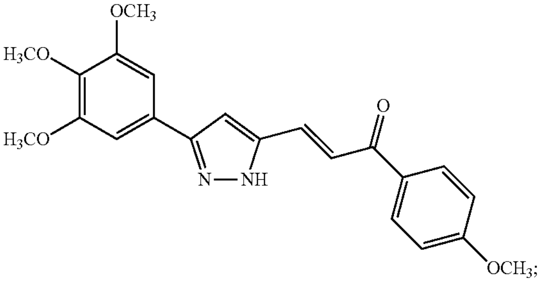
7f
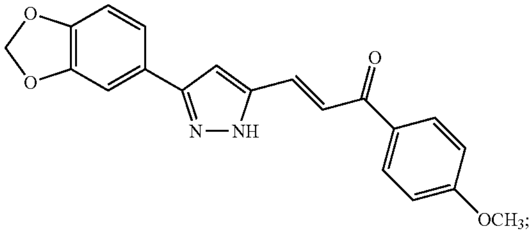
7g
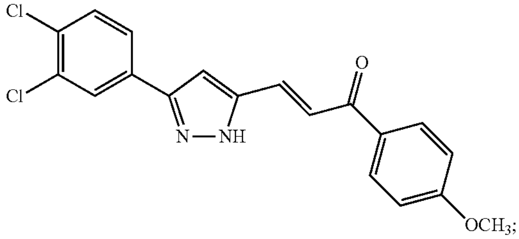
7h
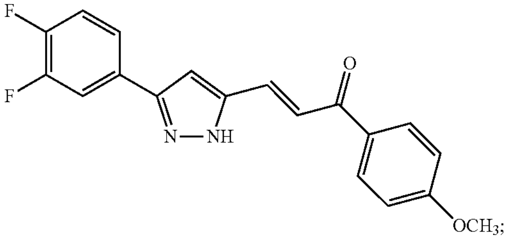
7i
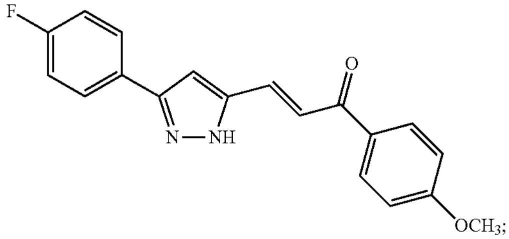
7j
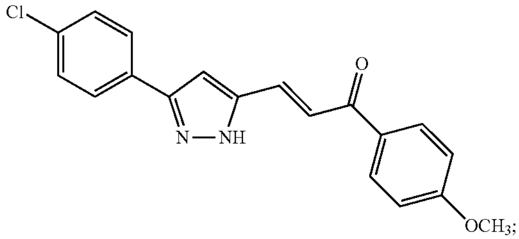

-continued
7k
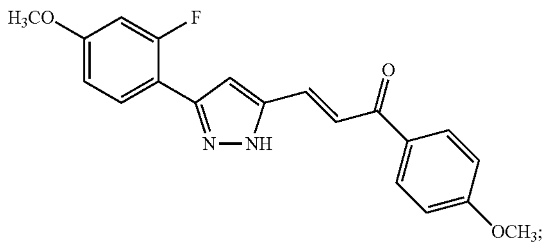
7l
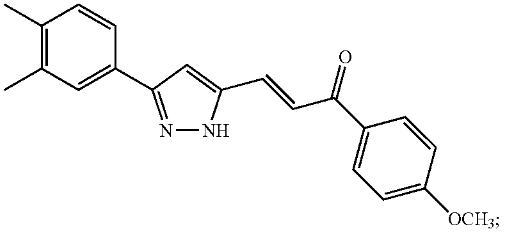
8a
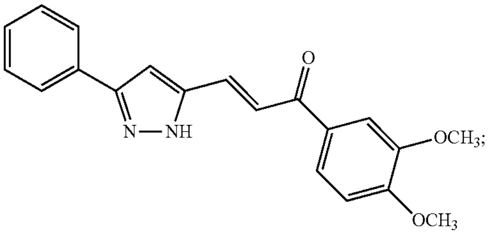
8b
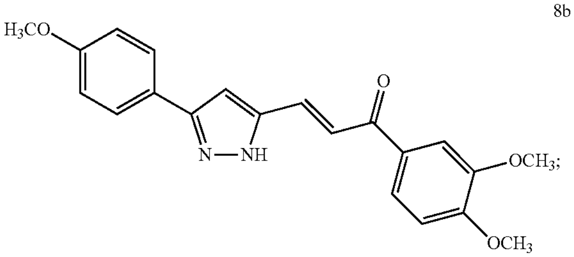
8c
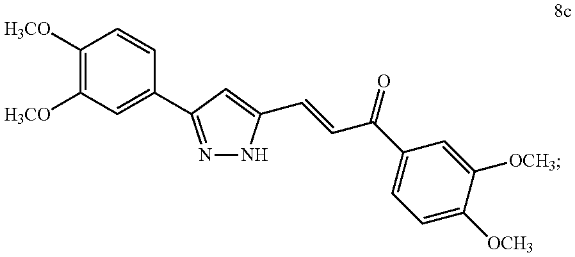
8d
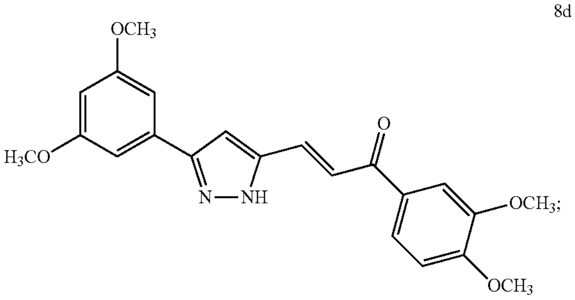
-continued
8e
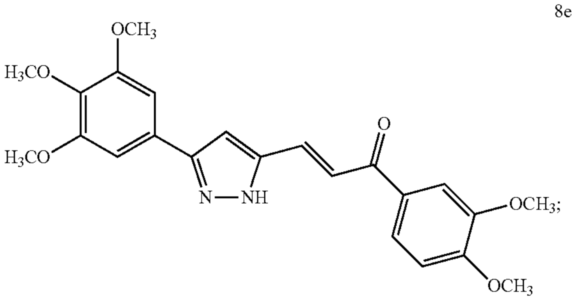
8f
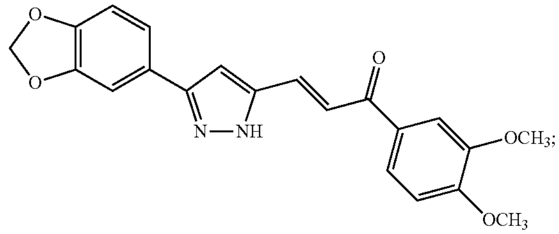
8g
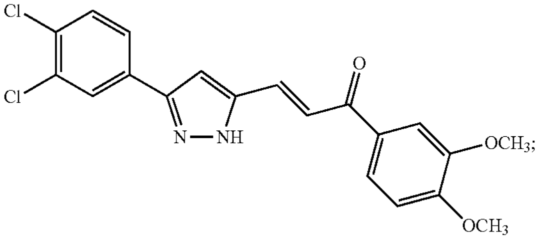
8h
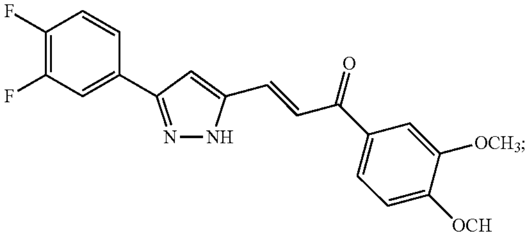
8i
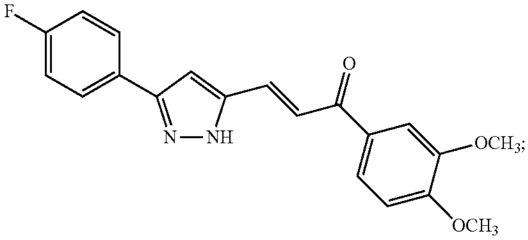
8j
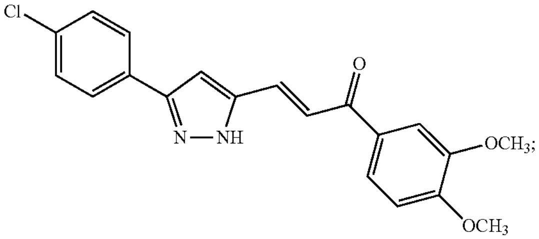

-continued
8k
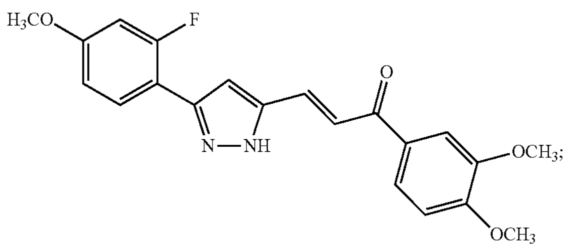
8l
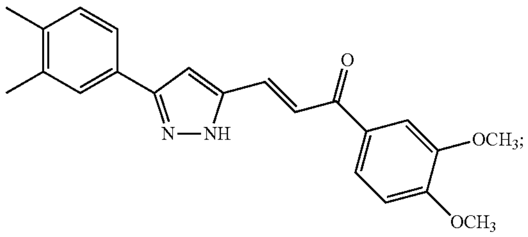
9a
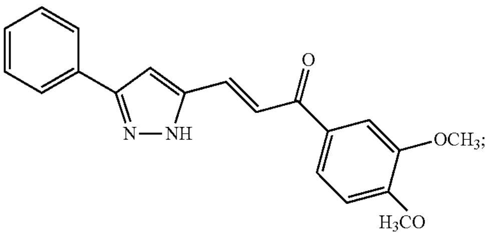
9b
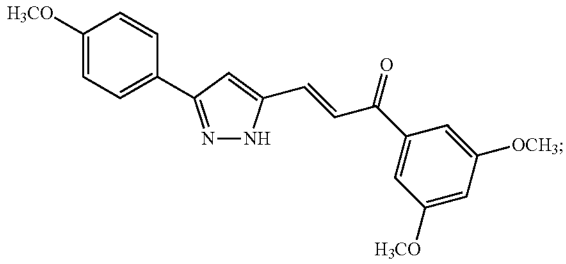
9c
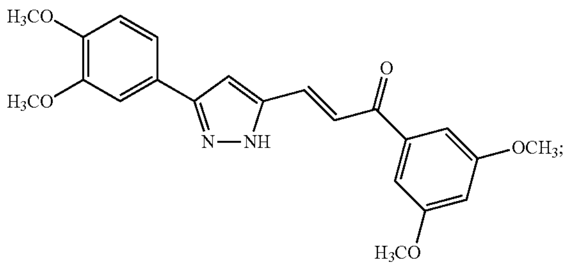
-continued
9d
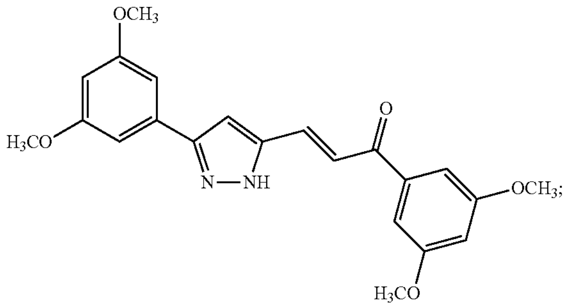
9e
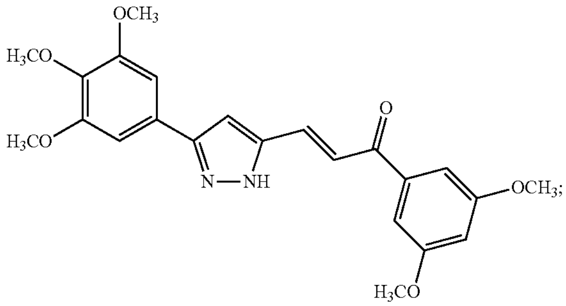
9f
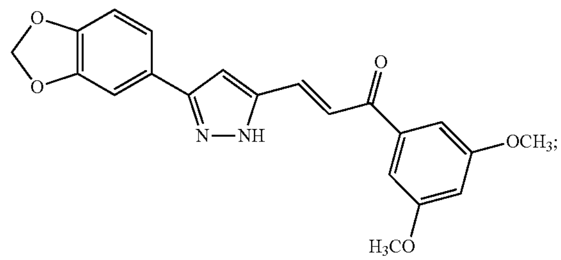
9g
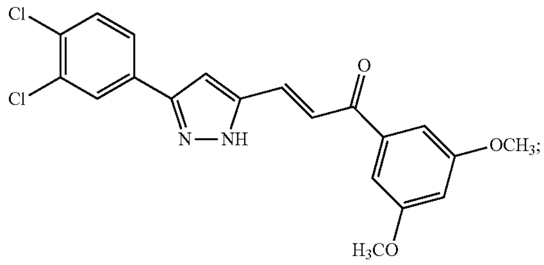
9h
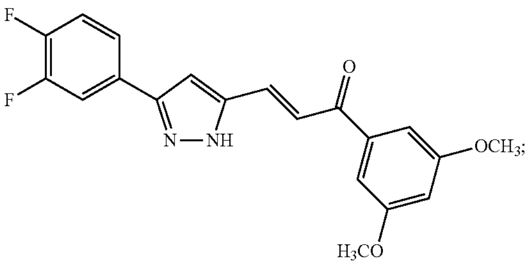

-continued
9i
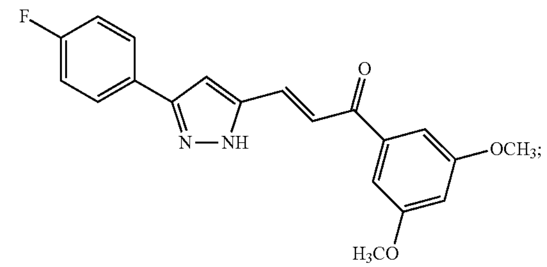
9j
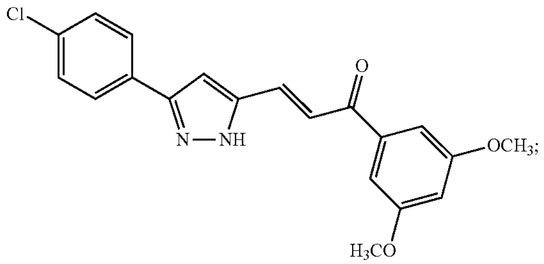
9k
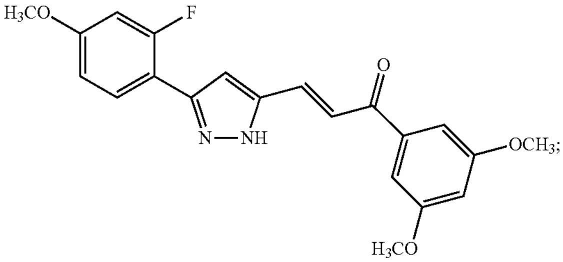
9l
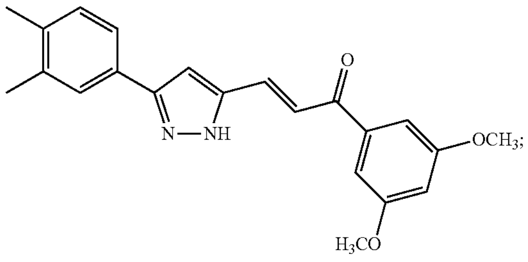
10a
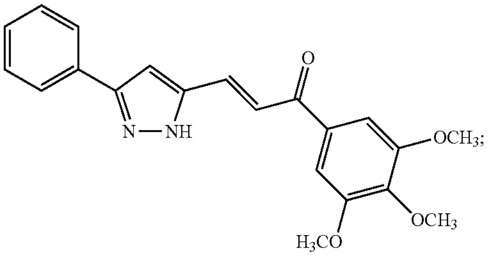
-continued
10b
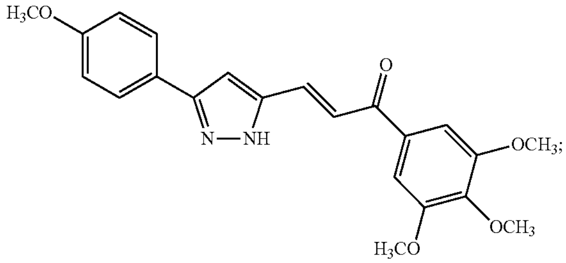
10c
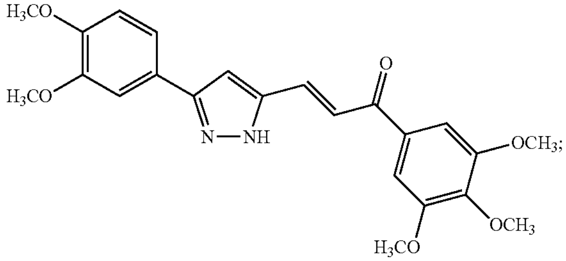
10d
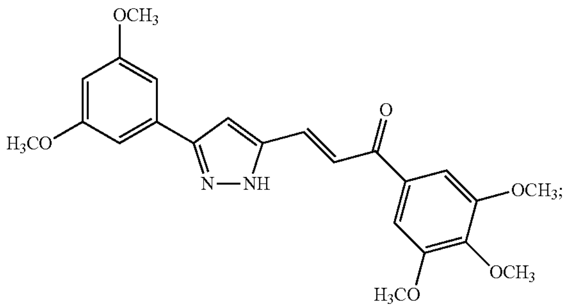
10e
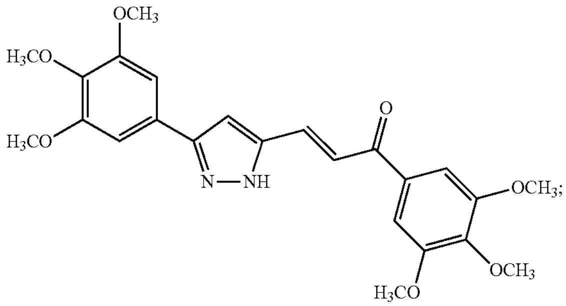
10f
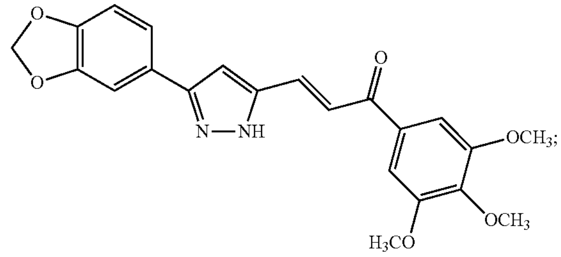

-continued
10g
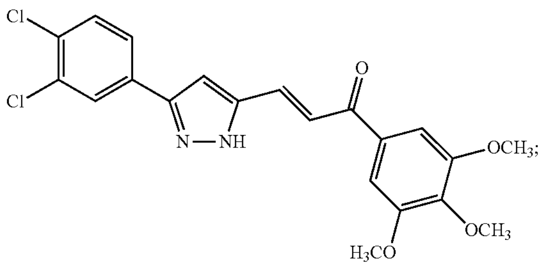
10h
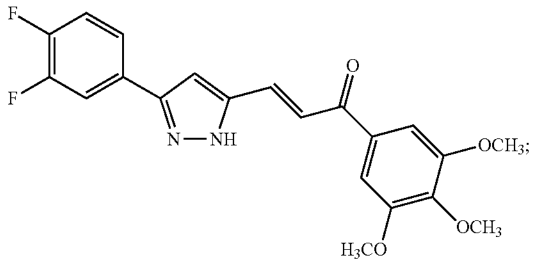
10i
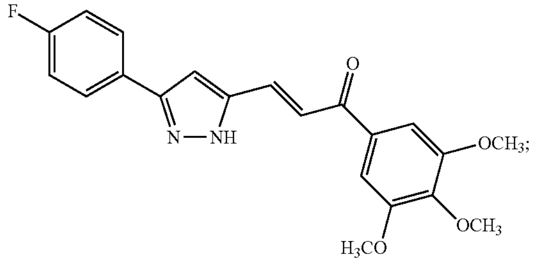
10j
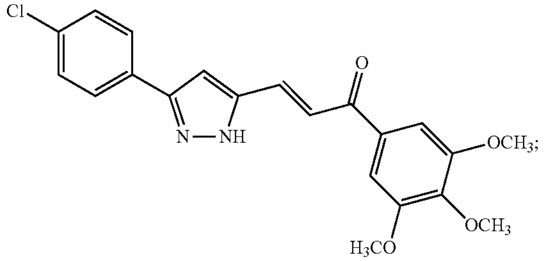
10k
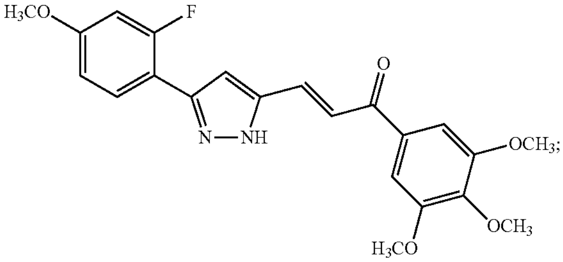
-continued
10l
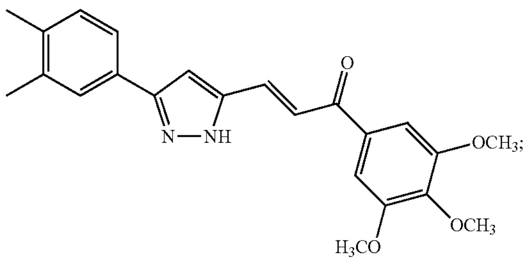
11a
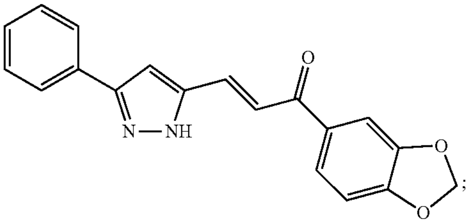
11b
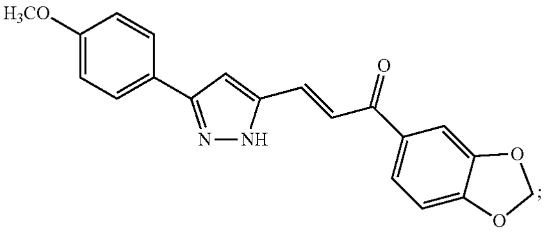
11c
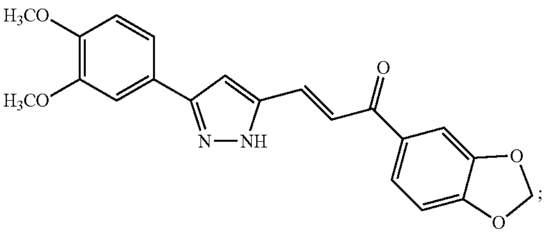
11d
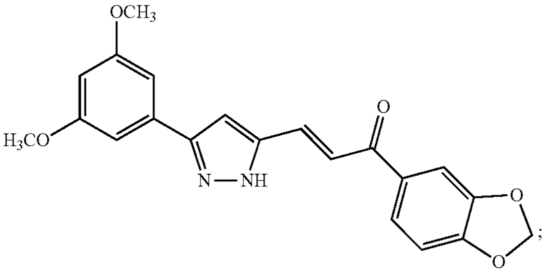
11e
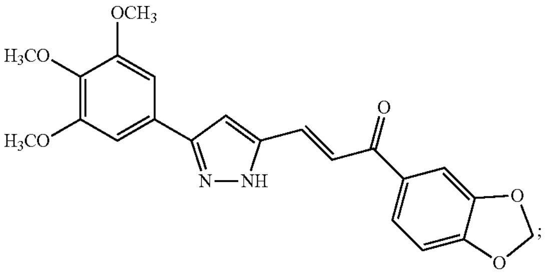

-continued
11f
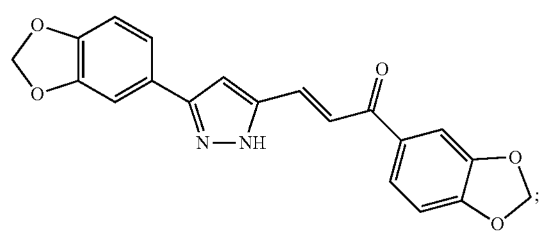
11g
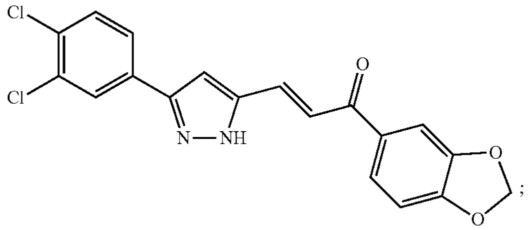
11h
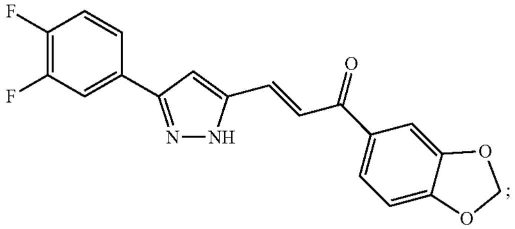
11i
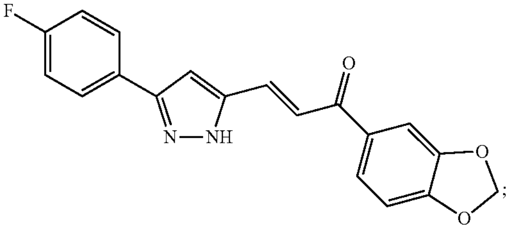
11j
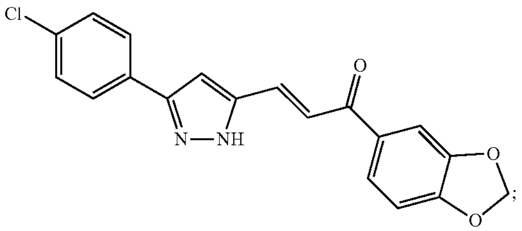
11k
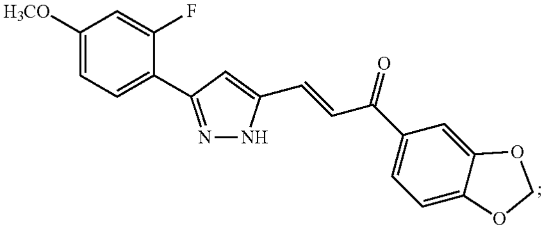
-continued
11l
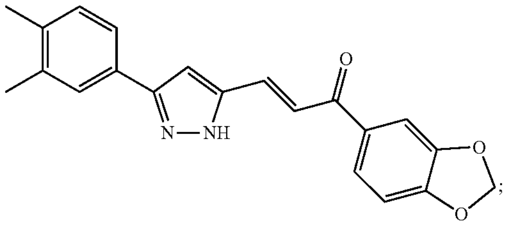
12a
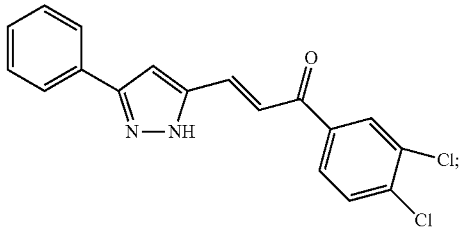
12b
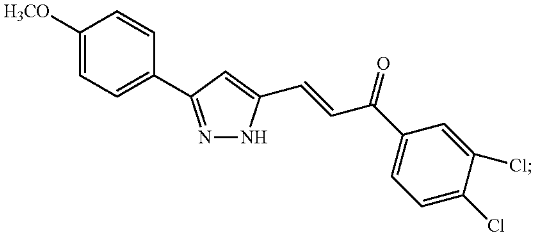
12c
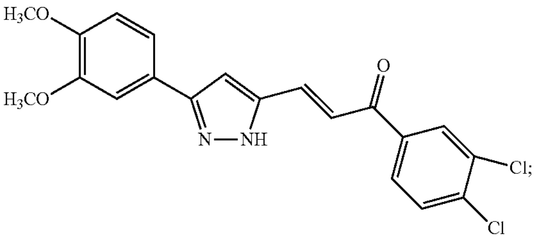
12d
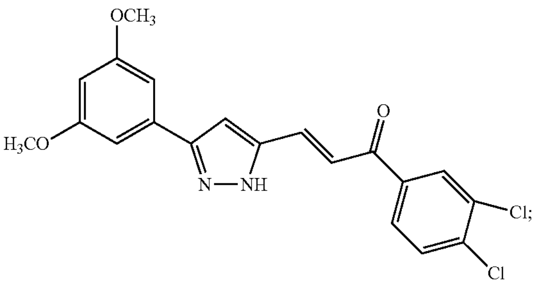
12e
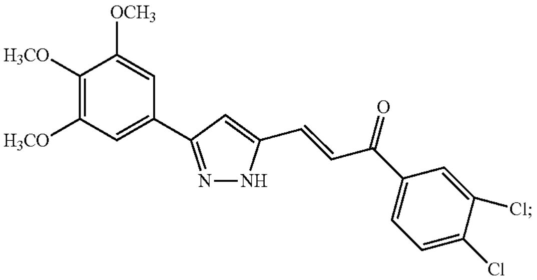

-continued
12f
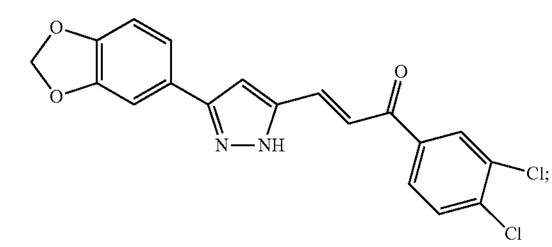
12g
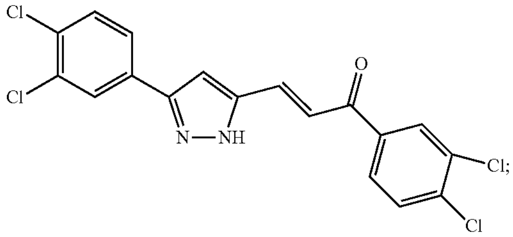
12h
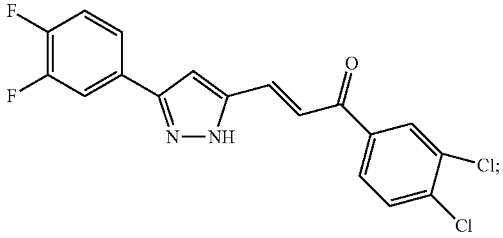
12i
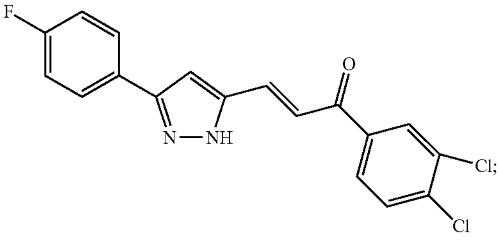
12j
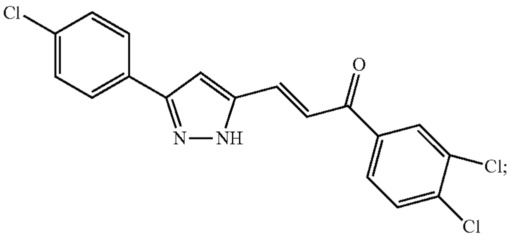
12k
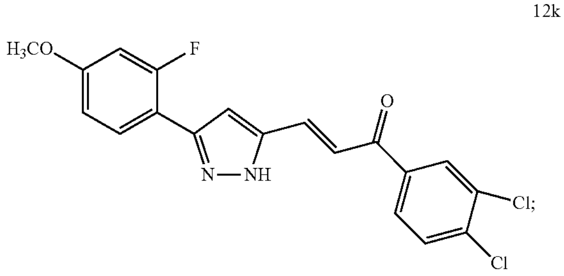
-continued
12l
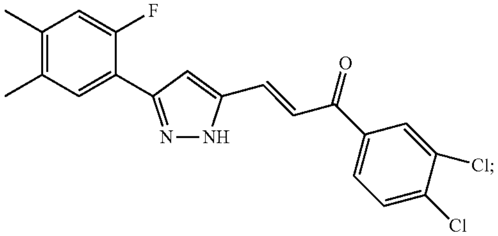
13a
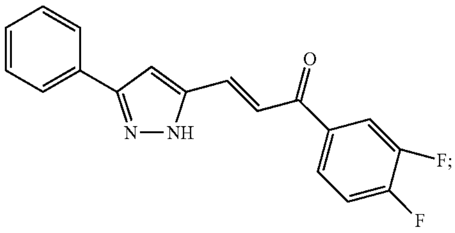
13b
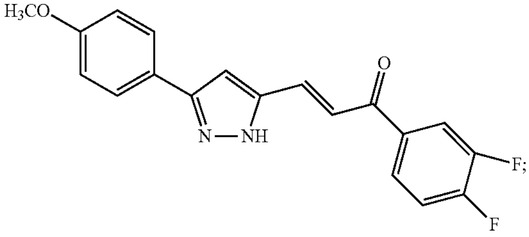
13c
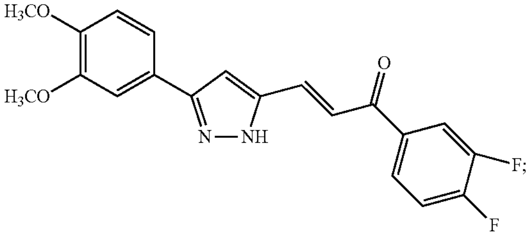
13d
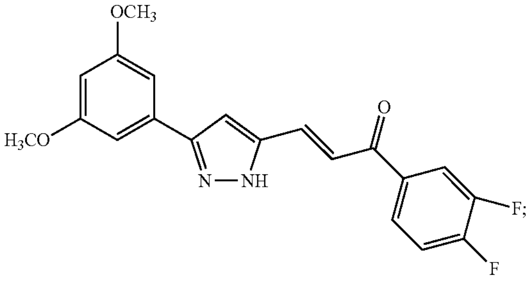
13e
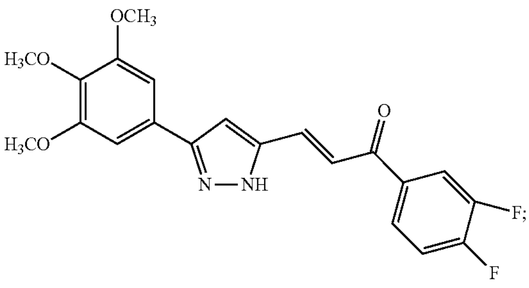

-continued
13f
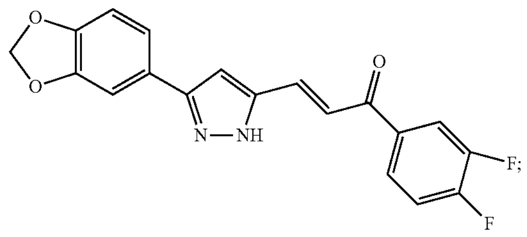
13g
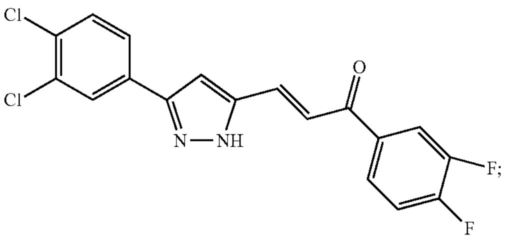
13h
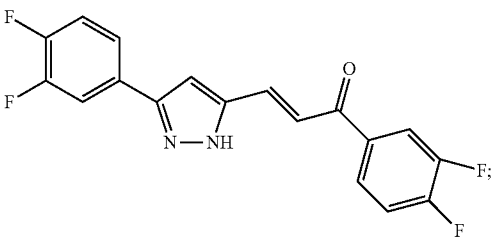
13i
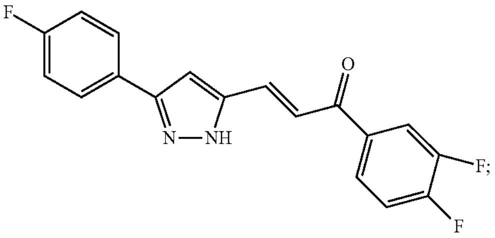
13j
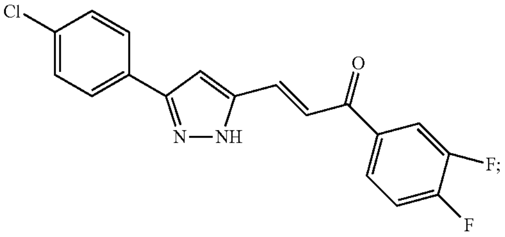
13k
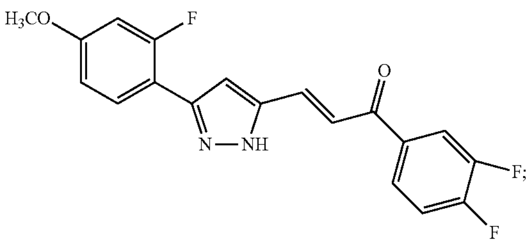
-continued
13l
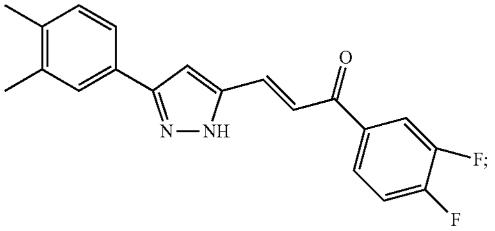
14a
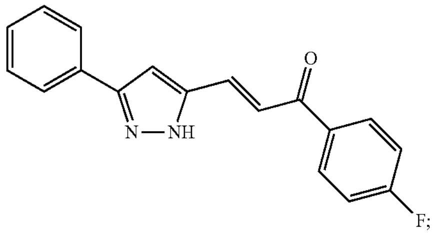
14b
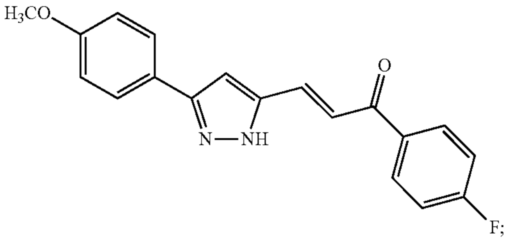
14c
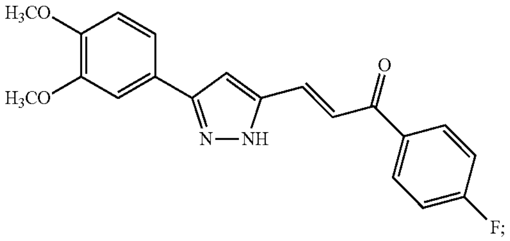
14d
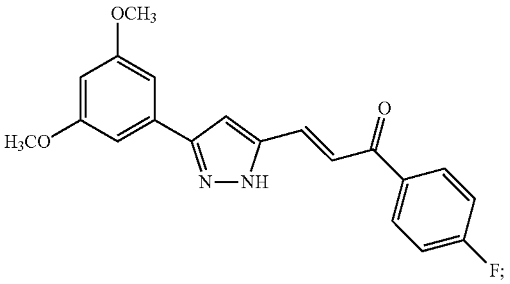
14e
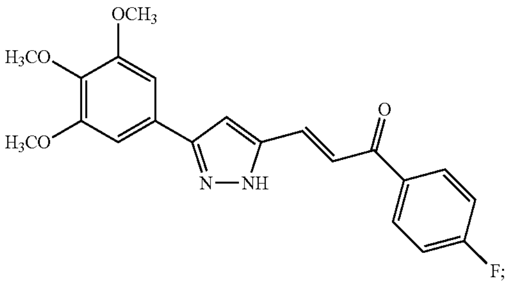

-continued
14f
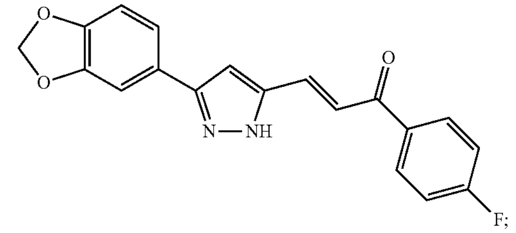
14g
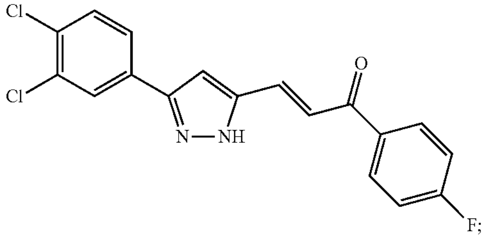
14h
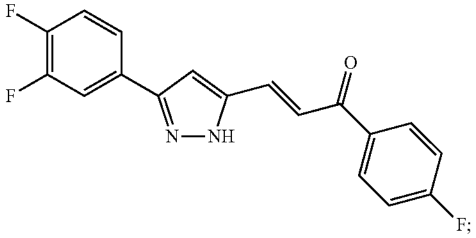
14i
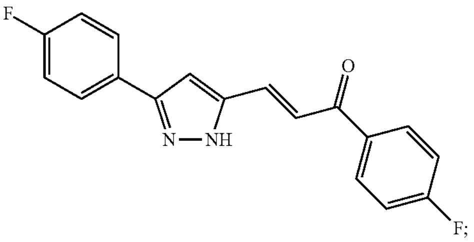
14j
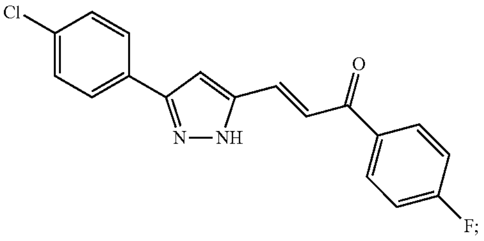
14k
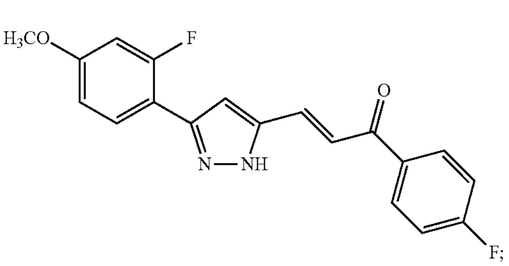
-continued
14l
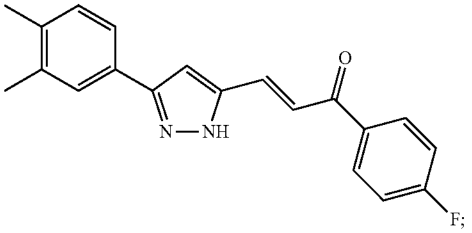
15a
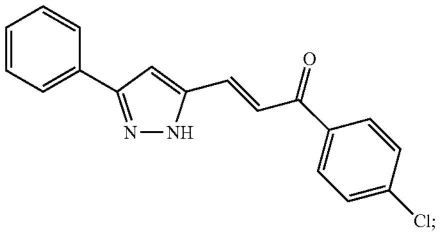
15b
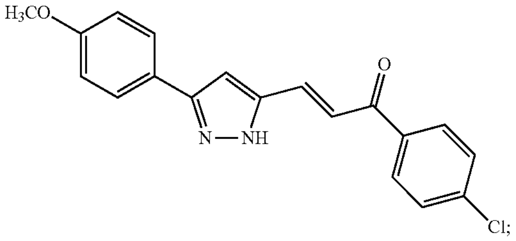
15c
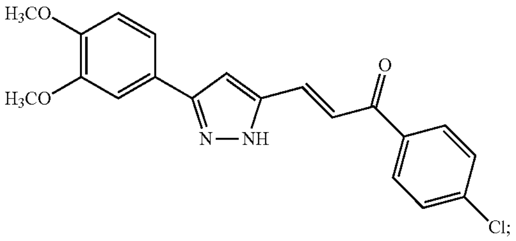
15d
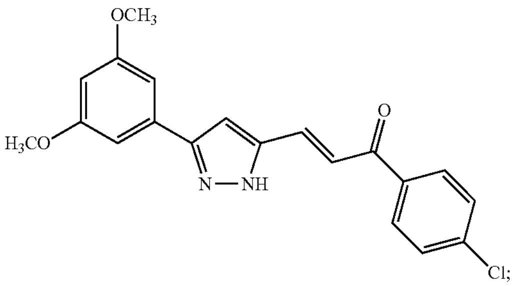
15e
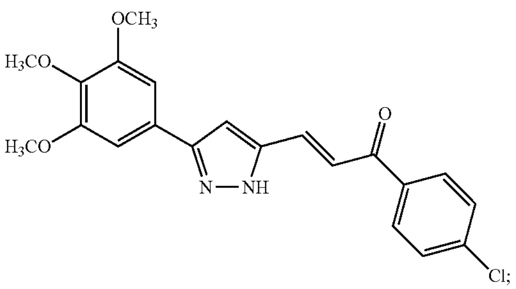

-continued
15f
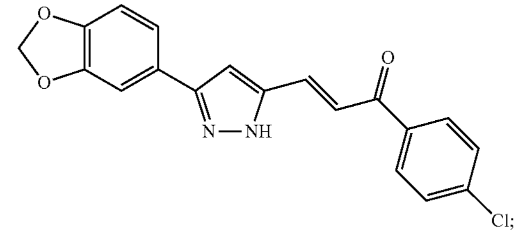
15g
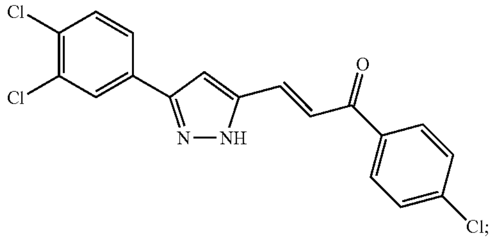
15h
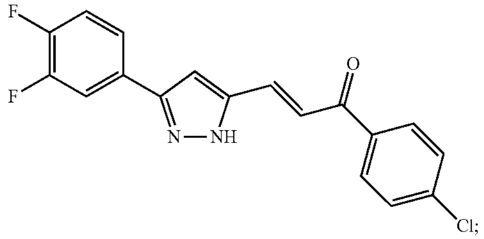
15i
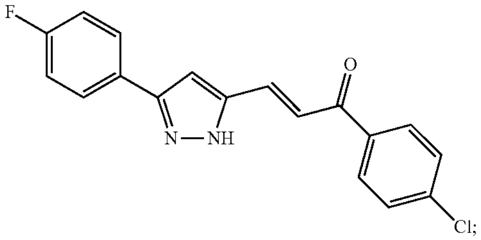
15j
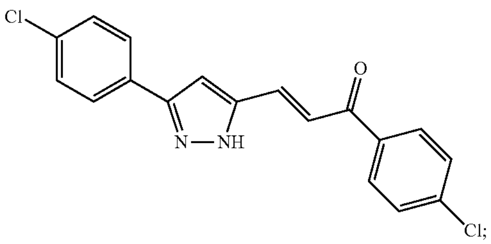
15k
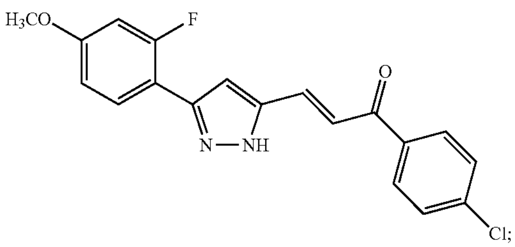
-continued
15l
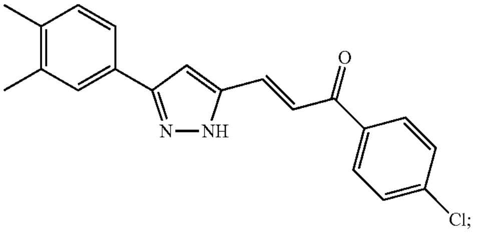
16a
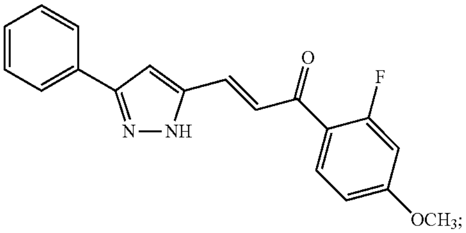
16b
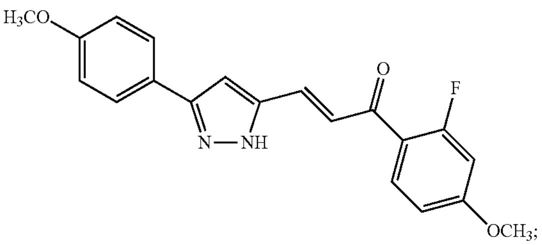
16c
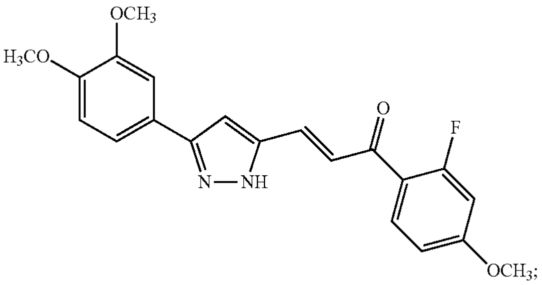
16d
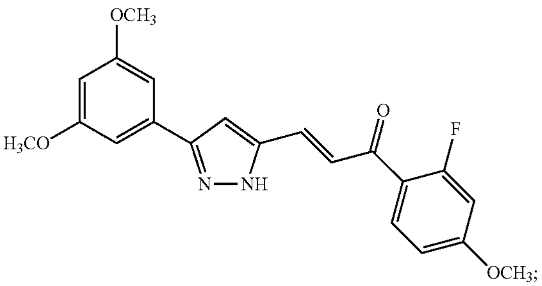

-continued
16e
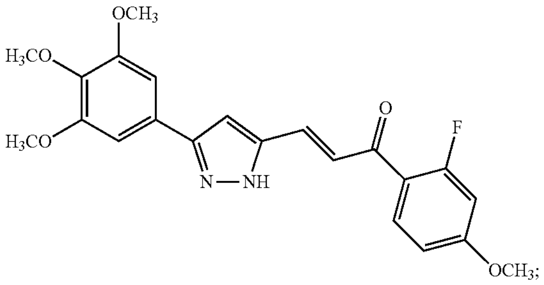
16f
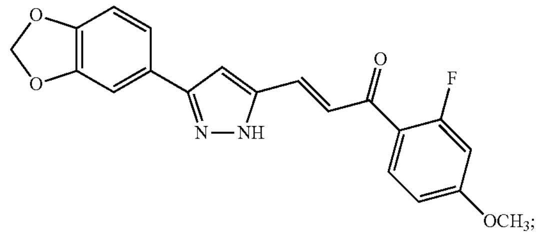
16g
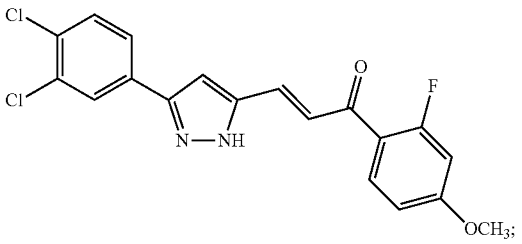
16h
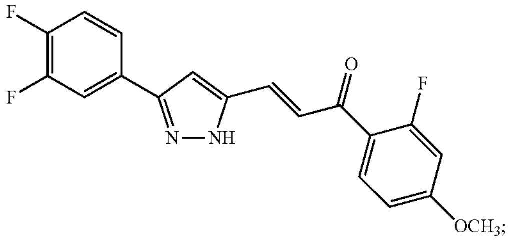
16i
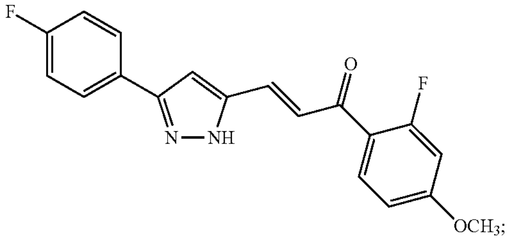
16j
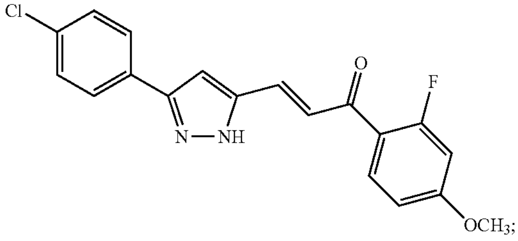
-continued
16k
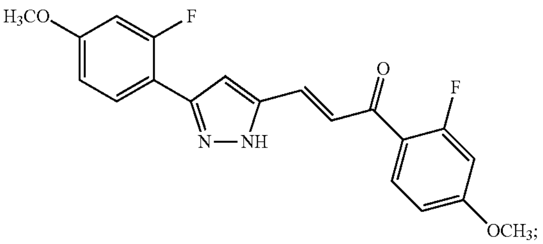
16l
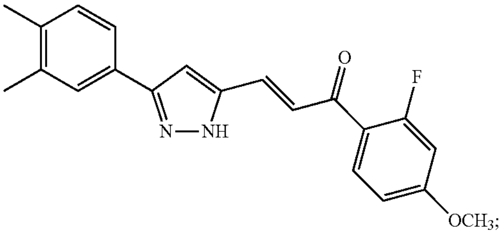
17a
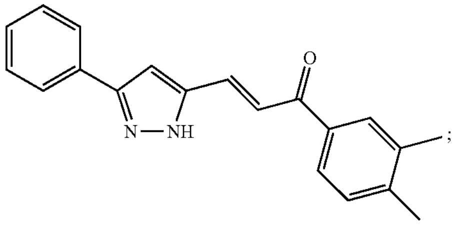
17b
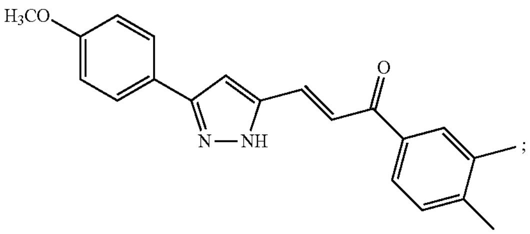
17c
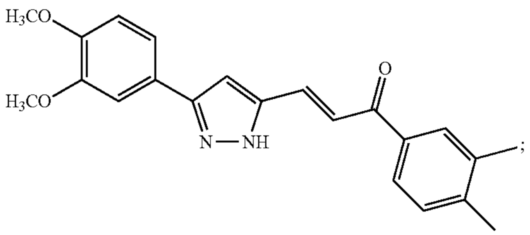
17d
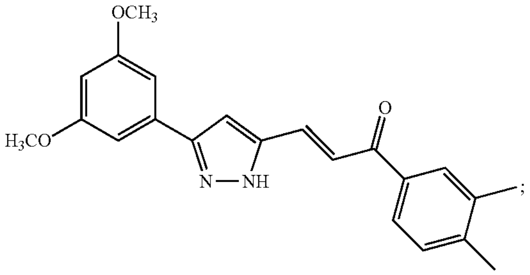

-continued
17e
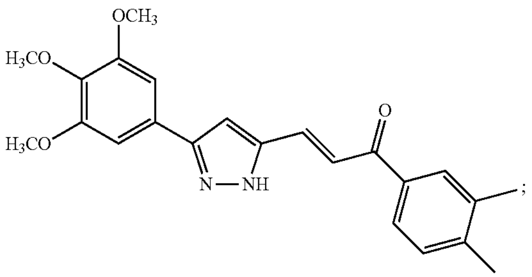
17f
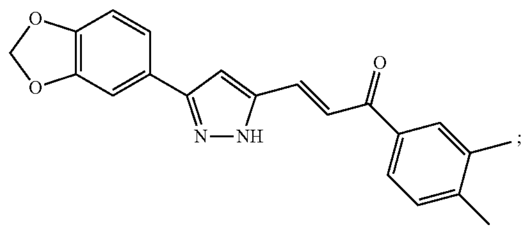
17g
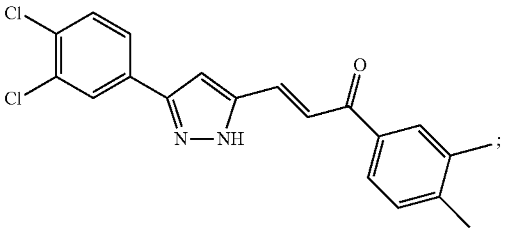
17h
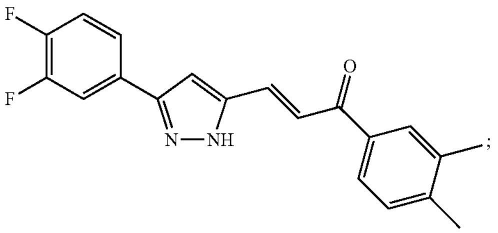
17i
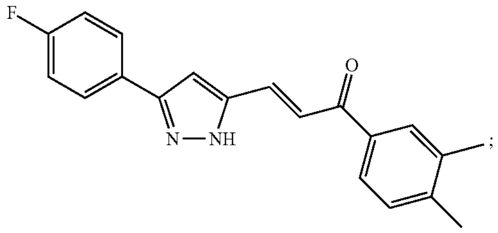
17j
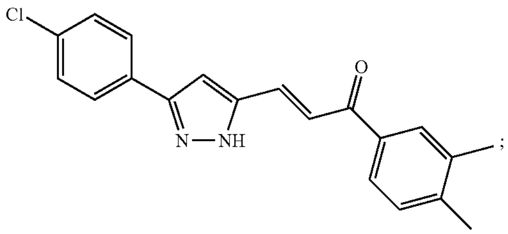
-continued
17k
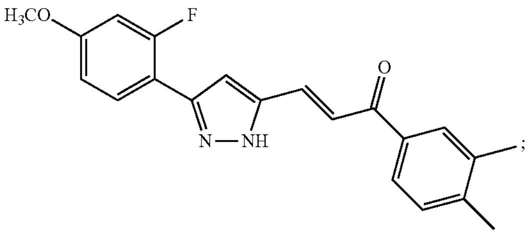
17l
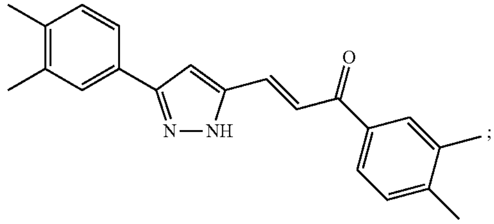
18a
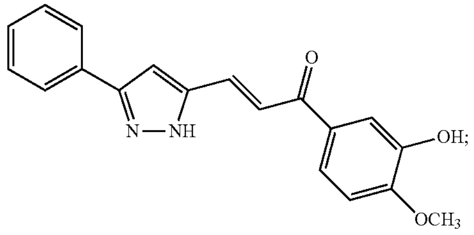
18b
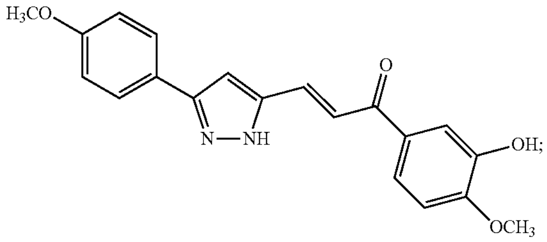
18c
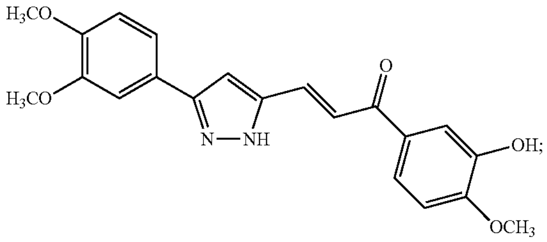
18d
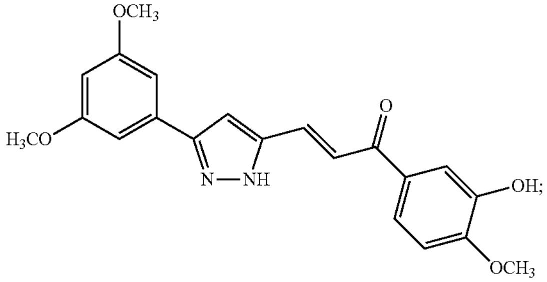

-continued
18e
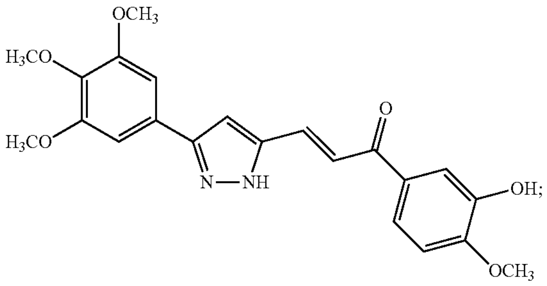
18f
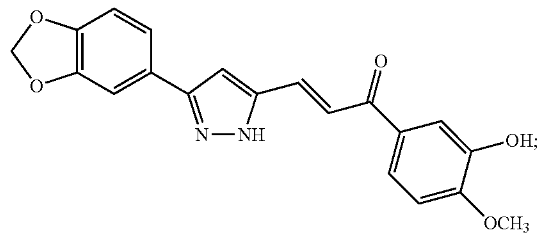
18g
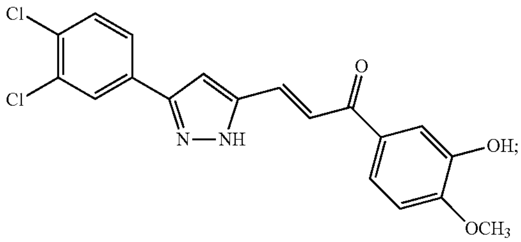
18h
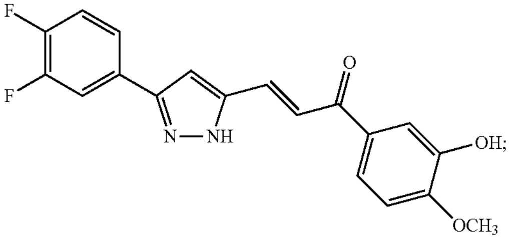
18i
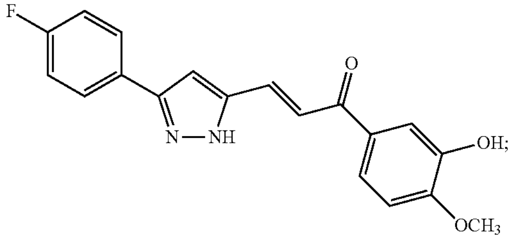
18j
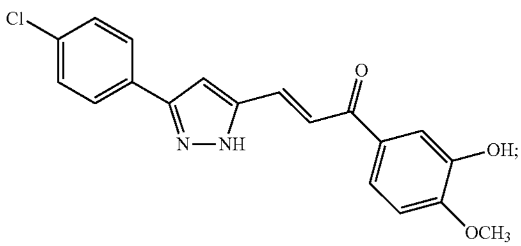
-continued
18k
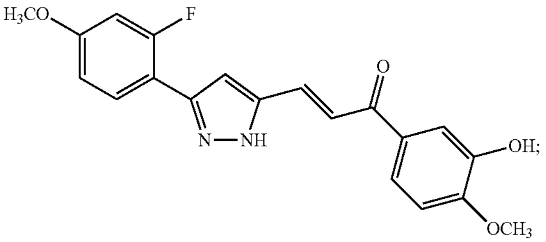
18l
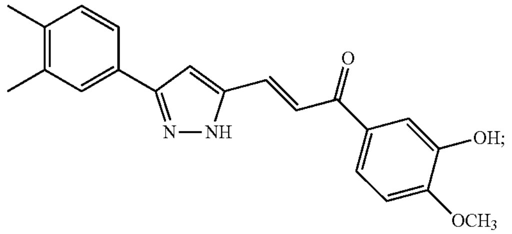
19a
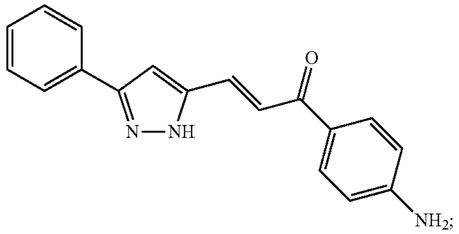
19b
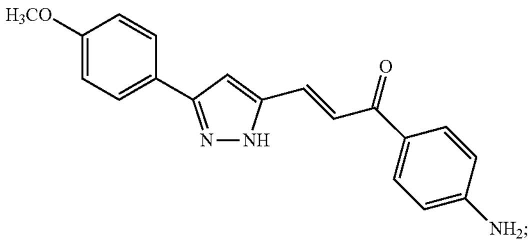
19c
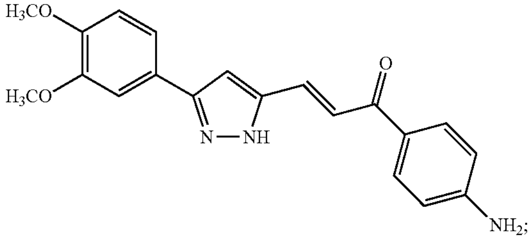
19d
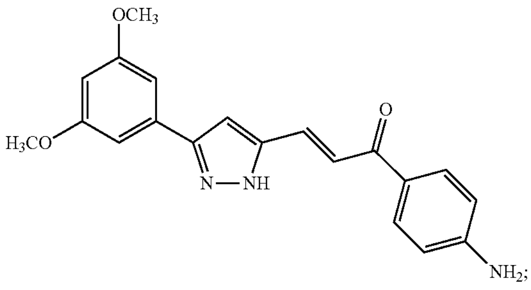

-continued
19e
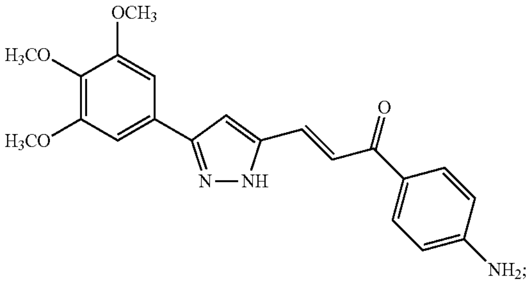
19f
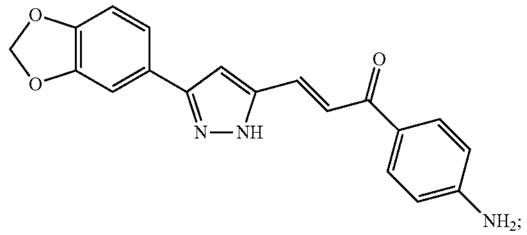
19g
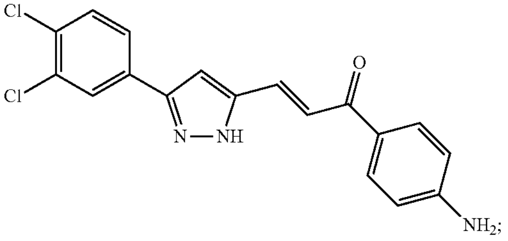
19h
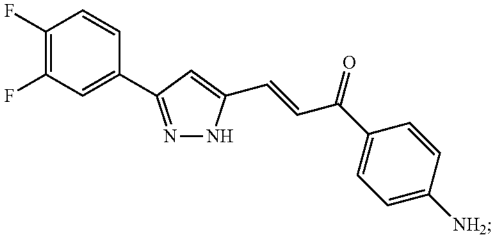
19i
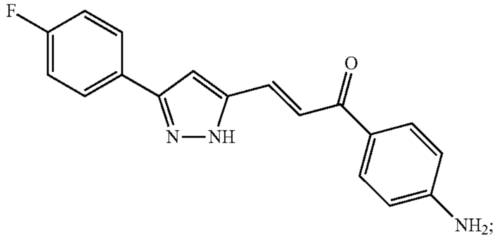
19j
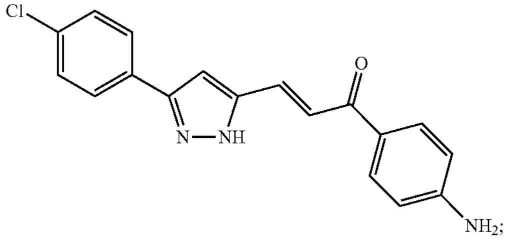
-continued
19k
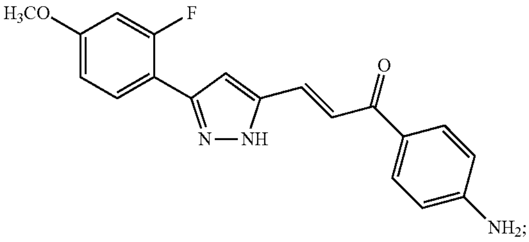
19l
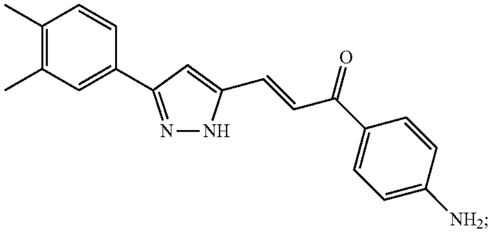
20a
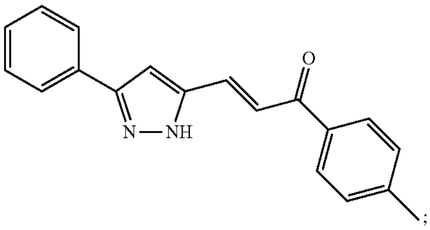
20b
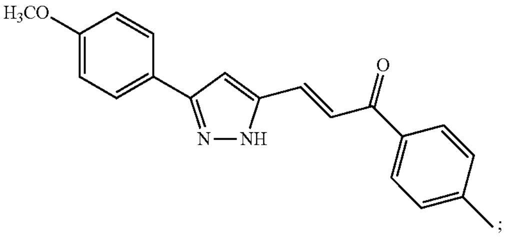
20c
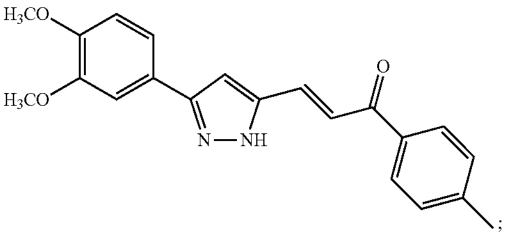
20d
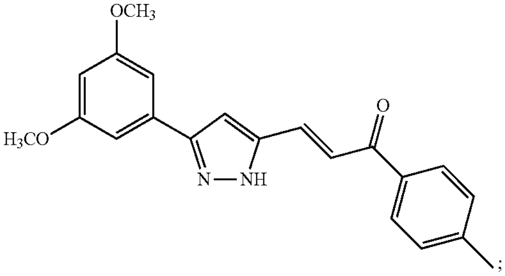

-continued
20e
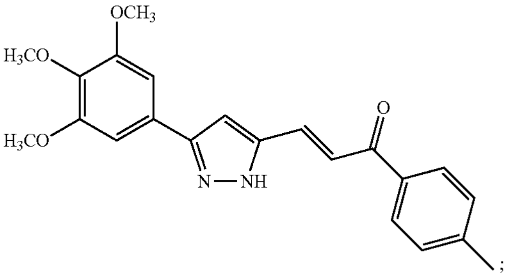
20f
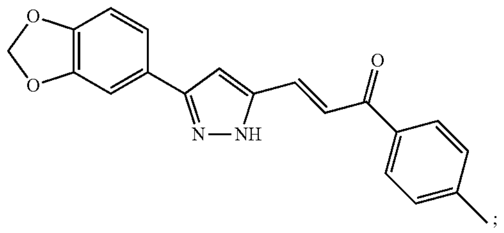
20g
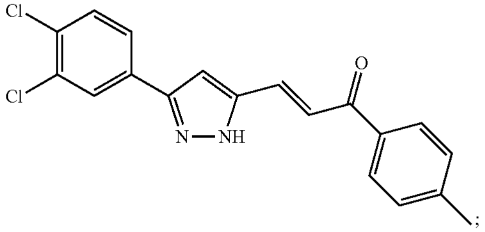
20h
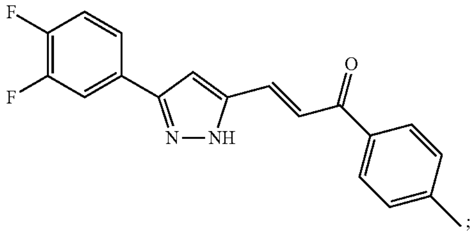
20i
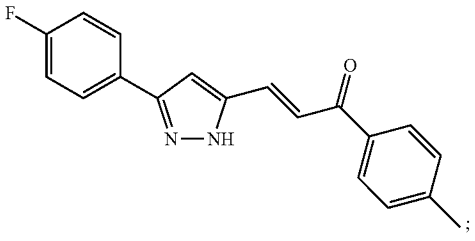
20j
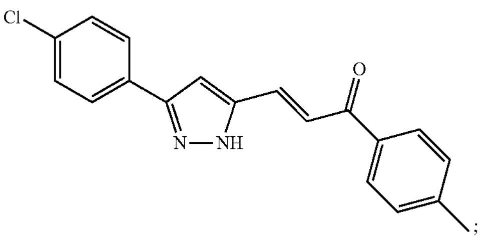
-continued
20k
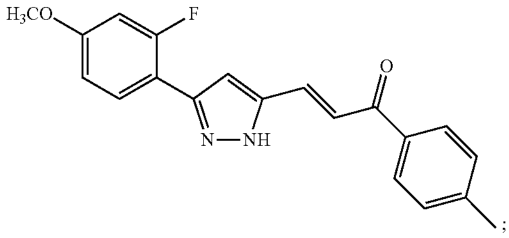
20l
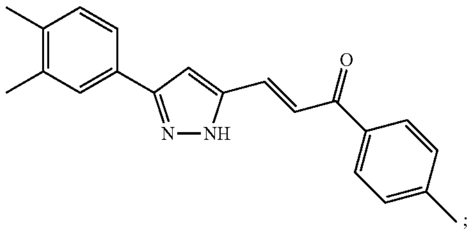
21a
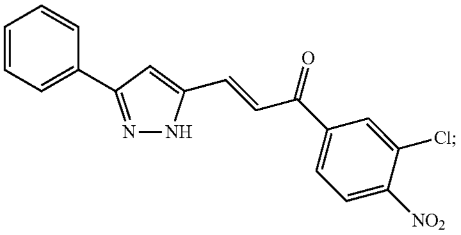
21b
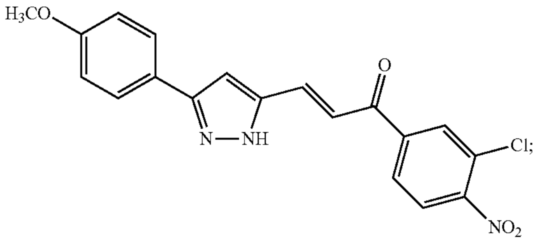
21c
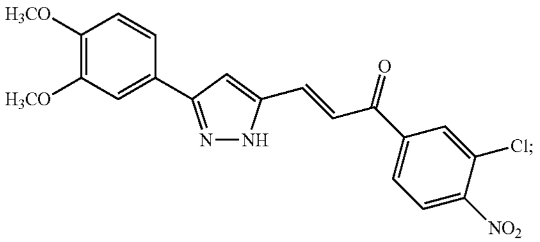
21d
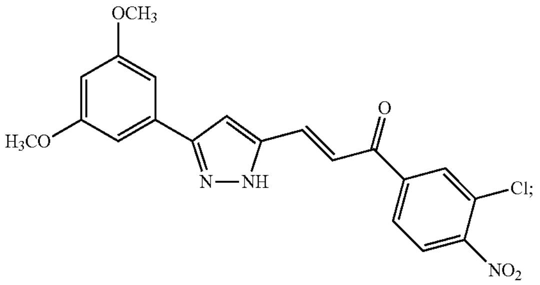

-continued
21e
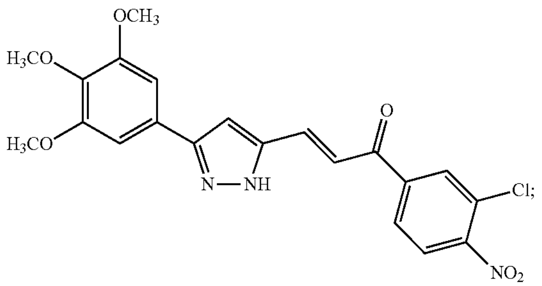
21f
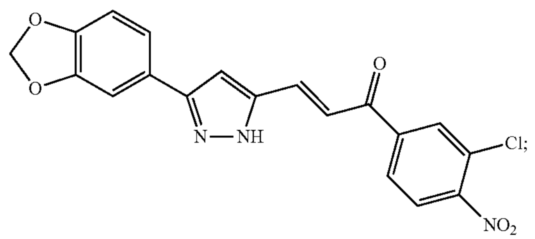
21g
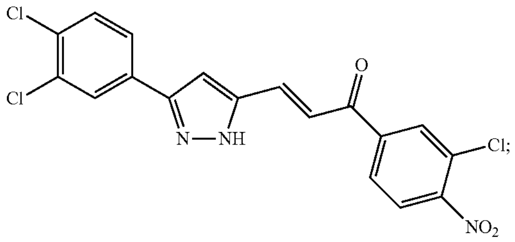
21h
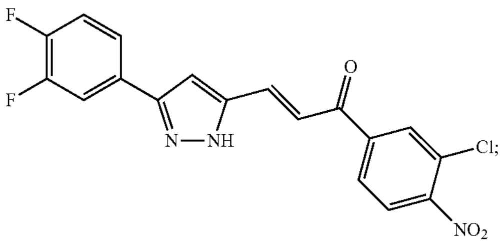
21i
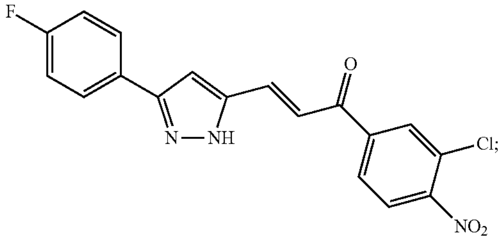
21j
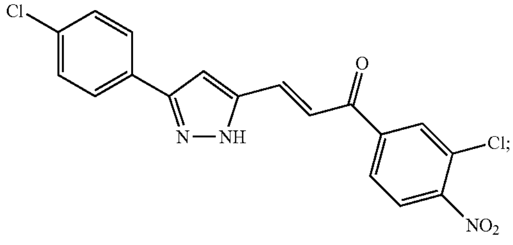
-continued
21k
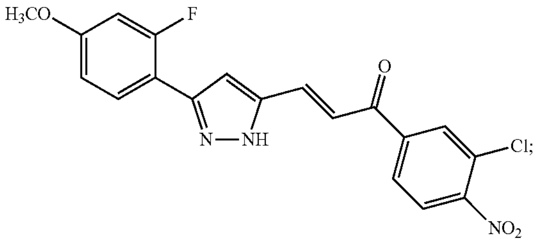
21l
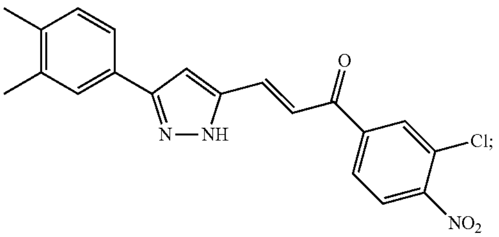
22a
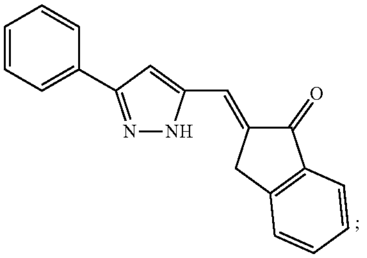
22b
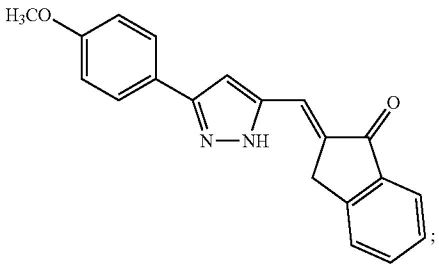
22c
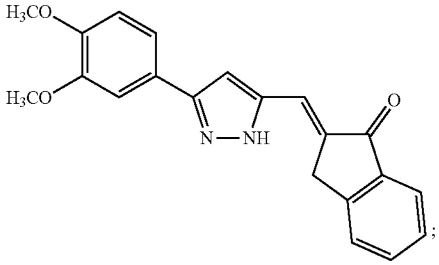
22d
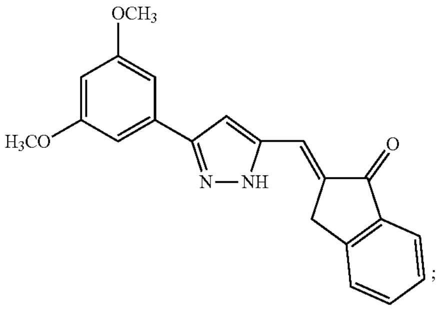

-continued
22e
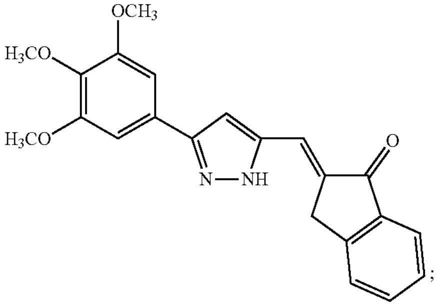
22f
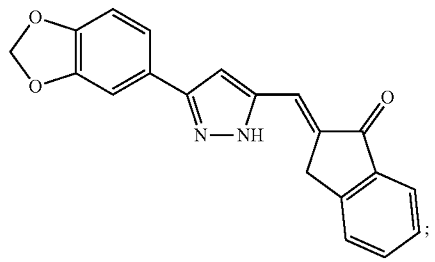
22g
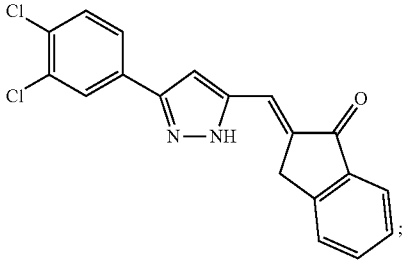
22h
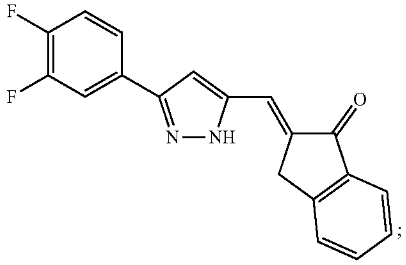
22i
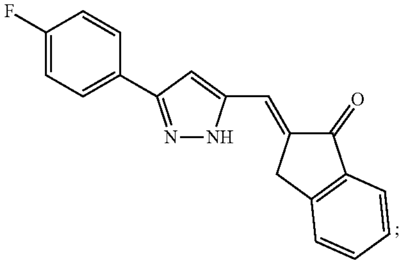
-continued
22j
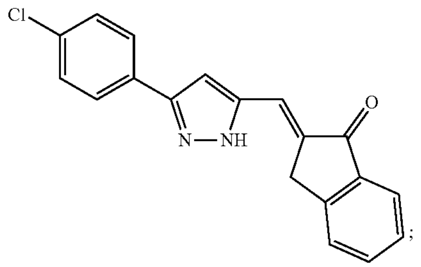
22k
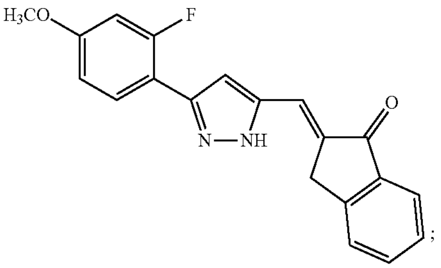
22l
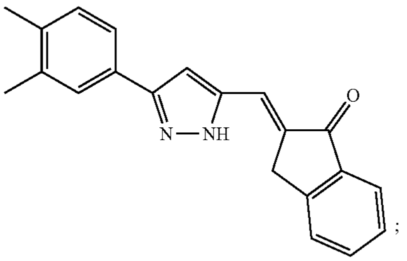
23a
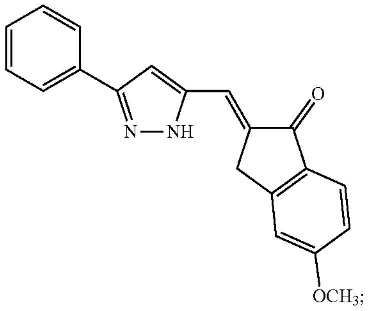
23b
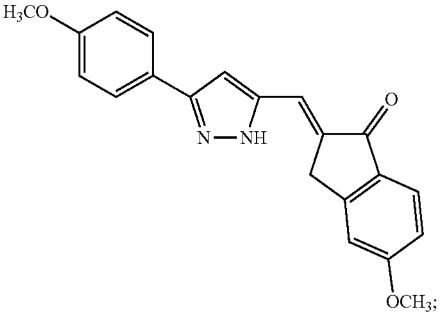

-continued
23c
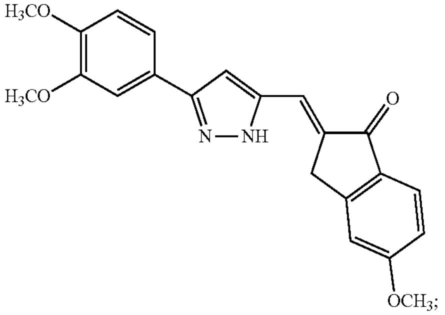
23d
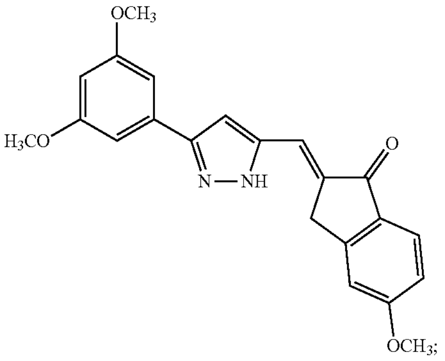
23e
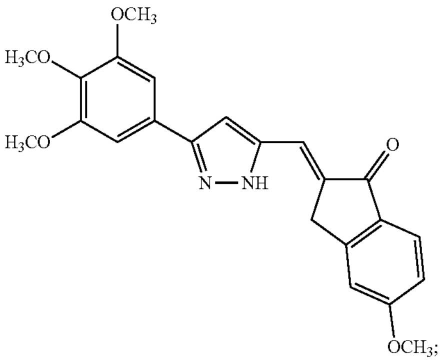
23f
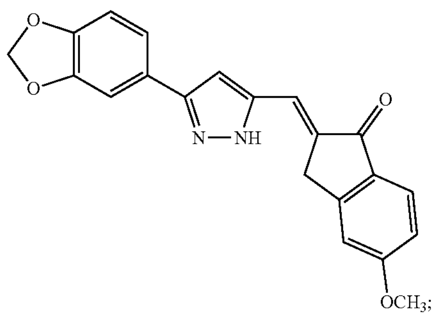
-continued
23g
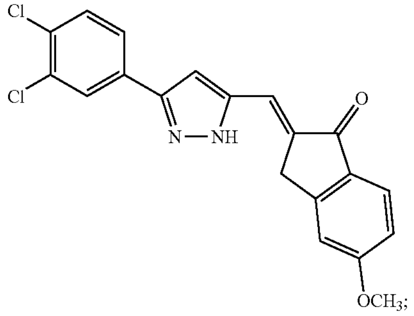
23h
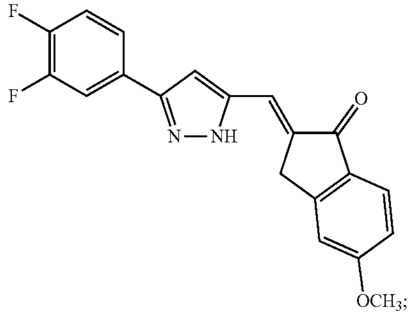
23i
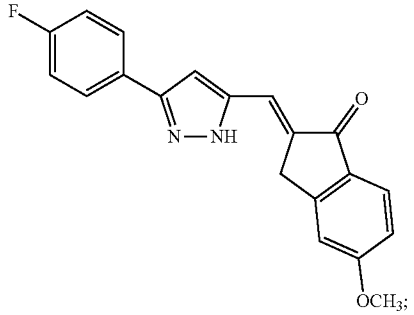
23j
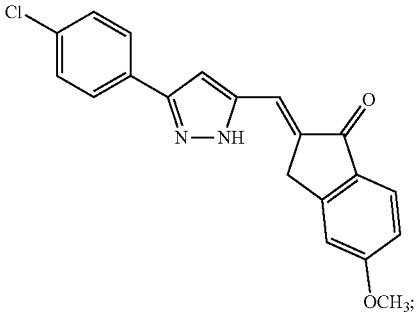
23k
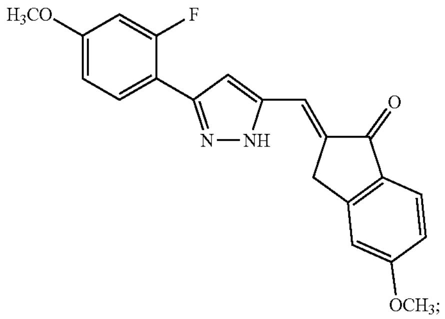

-continued
23l
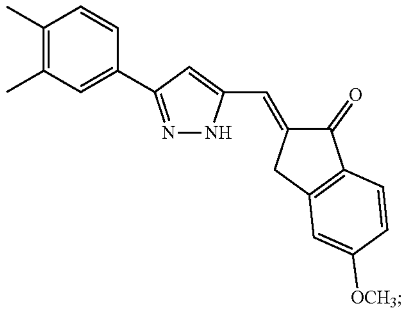
24a
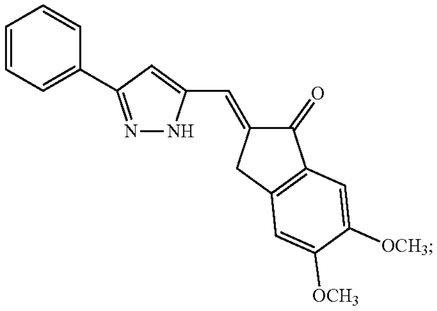
24b
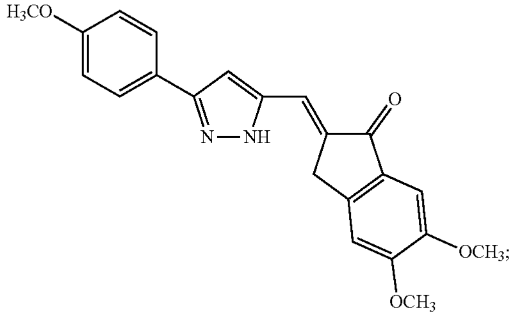
24c
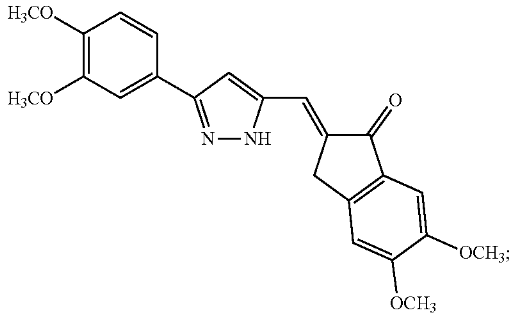
24d
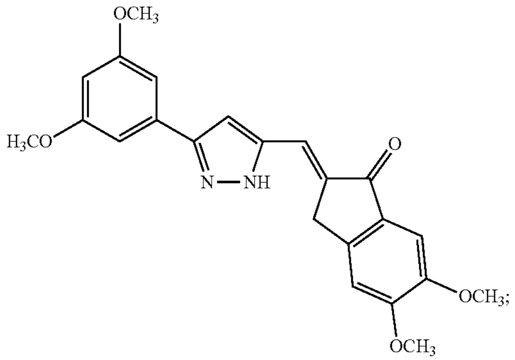
-continued
24e
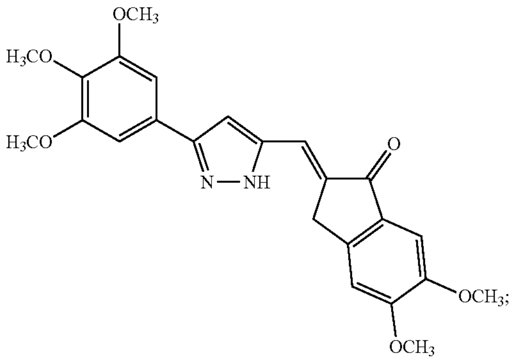
24f
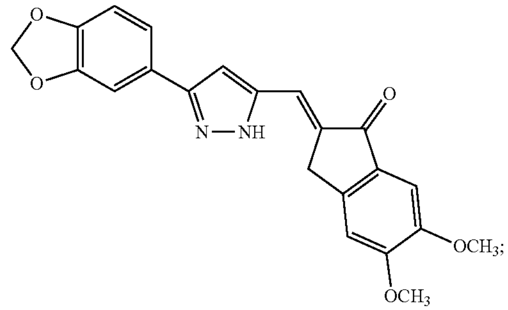
24g
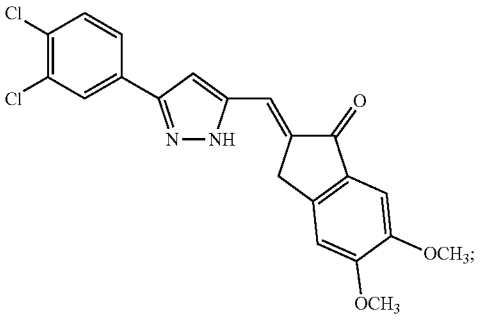
24h
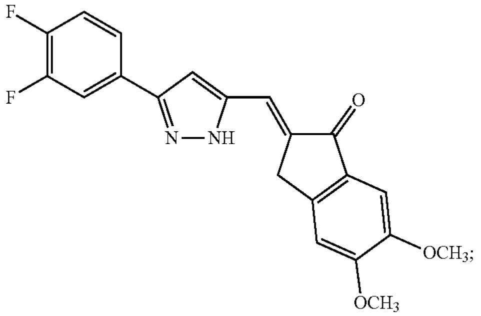
24i
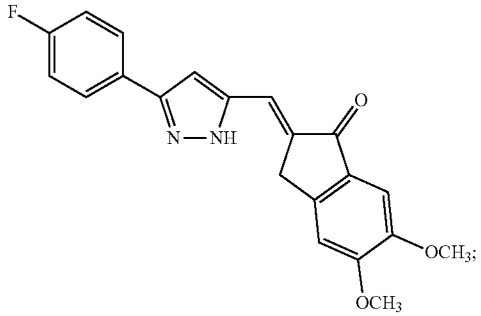

-continued

24j

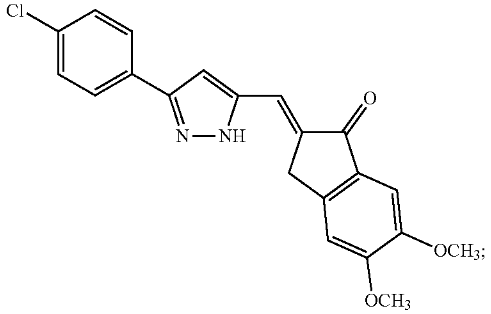

24k

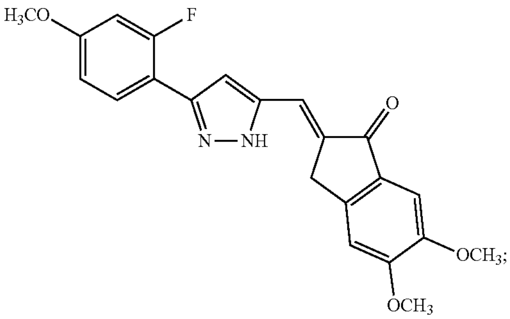

and

24l

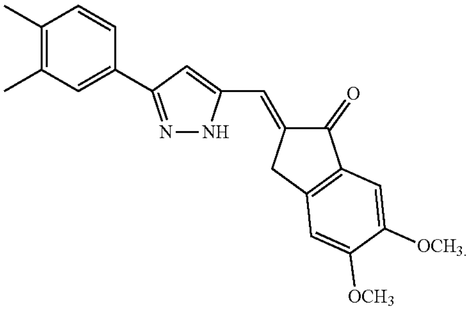

The pyrazolochalcone of formula A for use as antitumor agent, wherein the cancer is selected from the group consisting of leukemia, non-small cell lung cancer, colon cancer, CNS cancer, melanoma, ovarian cancer, renal cancer, prostate cancer, and breast cancer.

A process for the preparation of compounds of formula A,

Formula A

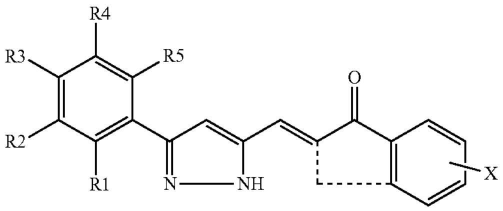

wherein,

R1, R2, R3, R4, R5=H, Cl, F, $CH_3$, $OCH_3$, 3,4($OCH_2O$)

X=H, Cl, F, $CH_3$, $OCH_3$, 3,4($OCH_2O$), $NH_2$, $NO_2$, OH.

wherein, the process comprises reacting 3-aryl-1H-pyrazole-5-carbaldehydes of formula (5a-l)

5(a-I)

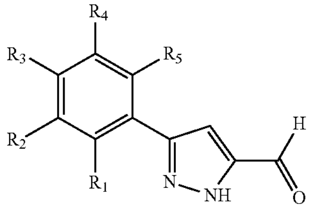

wherein $R_1$, $R_2$, $R_3$, $R_4$, $R_5$=[H, Cl, F, $CH_3$, $OCH_3$,3,4 ($OCH_2O$)]

with a compound selected from the group consisting of compounds of formulae a, b, c, d, e, f, g, h, i, j, k, l, m, n, o, p, q, r, or s.

a

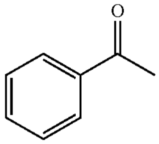

b

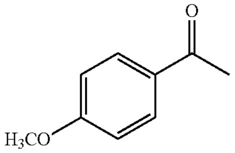

c

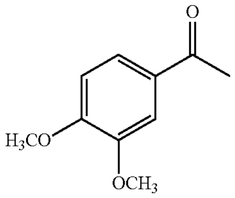

d

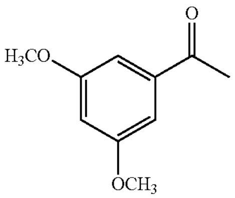

e

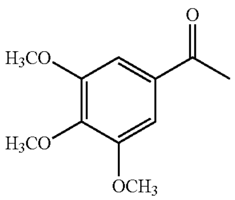

f

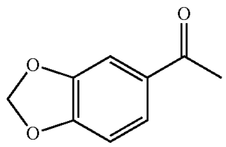

-continued g

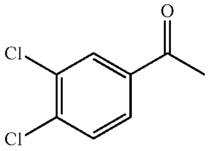

h

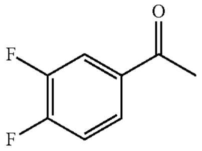

i

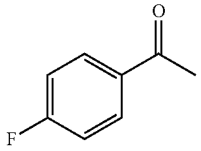

j

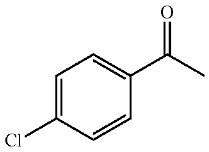

k

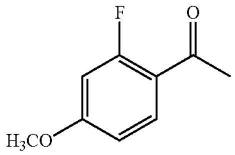

l

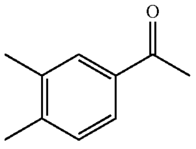

m

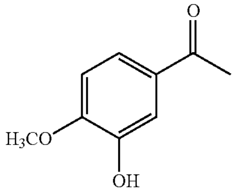

n

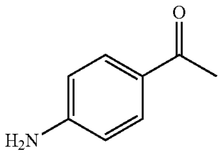

o

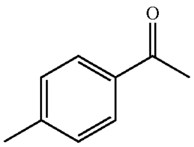

-continued p

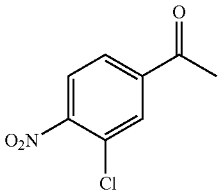

q

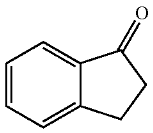

r

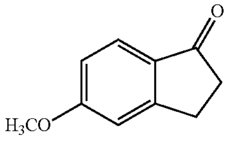

s

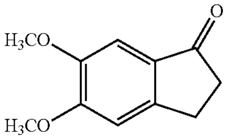

in an alcohol in the presence of a base at a temperature ranging between 28° C. to 35° C. for a period ranging between 2 to 4 h to obtain a reaction mixture, evaporating the reaction mixture by vacuum distillation and neutralizing the residue with dil. HCl followed by extraction with water immiscible solvent; drying over anhydrous $Na_2SO_4$ and evaporating the solvent to provide a crude product, purifying the product by chromatographic method using ethyl acetate/hexane as eluent to obtain the pure desired compounds of formulae: 6a-21a, 6b-21b, 6c-21c, 6d-21d, 6e-21e, 6f-21f, 6g-21g, 6h-21h, 6i-21i, 6j-21j, 6k-21k, 6l-21l and 22a-24a, 22b-24b, 22c-24c, 22d-24d, 22e-24e, 22f-24f, 22g-24g, 22h-24h, 22i-24i, 22j-24j, 22k-24k, 22l-24l.

In one more embodiment of the invention the alcohol used is selected from ethanol or methanol.

In a further embodiment of the invention the base used is selected from NaOH or KOH.

In still further embodiment of the invention the water immiscible solvent is selected from the group consisting of ethyl acetate, chloroform or dichloromethane.

DETAILED DESCRIPTION OF THE INVENTION

The precursors 3-phenyl-1H-pyrazole-5-carbaldehydes of formulae 5(a-l) have been prepared using literature method (Yamazaki, Y., Tanaka, K., Nicholson, B., Deyanat-Yazdi, G., Potts, B., Yoshida, T., Oda, A., Kitagawa, T., Orikasa, S., Kiso, Y., Yasui, H., Akamatsu, M., Chinen, T., Usui, T., Shinozaki, Y., Yakushiji, F., Miller, B. R., Neuteboom, S., Palladino, M., Kanoh, K., Lloyd, G. K. and Hayashi, Y. Synthesis and structure-activity relationship study of anti-microtubule agents phenylahistin derivatives with a didehydropiperazine-2,5-dione structure. *J. Med. Chem.* 2012, 55, 1056-1071). The crucial intermediates for the preparation of precursors 3-phenyl-1H-pyrazole-5-carbaldehydes of formulae 5(a-l) are ethyl 3-phenyl-1H-pyrazole-5-carboxylates 4(a-l) have been prepared using literature methods (Nagarapu, L., Gaikwad, H. K., Sarikonda, K., Mateti, J., Bantu, R., Raghu, P. S., Manda, K. M. and Kalvendi. S. V. Synthesis and cytotoxicity evaluation of 1-[3-(9H-carbazol-4-yloxy)-2-hydroxypropyl]-3-aryl-1H-pyrazole-5-carboxylic acid derivatives. Eur. J. Med. Chem. 2010, 45, 4720-4725, Sidique, S., Ardecky, R., Su, Y., Narisawa, S., Brown, B., Millan, J. L., Sergienko, E. and Cosford, N. D., Design and synthesis of pyrazole derivatives as potent and selective inhibitors of tissue-nonspecific alkaline phosphatase (TNAP). *Bioorg. Med. Chem. Lett.* 2009, 19, 222-225).

These pyrazolochalcones have shown promising anticancer activity in various cell lines. The molecules synthesized are of immense biological significance. This resulted in design and synthesis of new congeners as illustrated in scheme 1 which comprises: The Claisen condensation between 3-phenyl-1H-pyrazole-5-carbaldehydes of formulae 5(a-l) and the compounds of formulae a, b, c, d, e, f, g, h, j, k, l, m, n, o, p for synthesis of the compounds (6a-21a to 6l-21l) or q, r, s for synthesis of the compounds (22a-24a to 22l-24l), respectively.

The Synthesis of pyrazolochalcones described in the present invention are outlined in Scheme 1. The final step has been carried out by the application of Claisen condensation between equimolar mixture of 3-phenyl-1H-pyrazole-5-carbaldehydes formulae 5(a-l) and substituted acetophenones/indanones in the presence of base in alcohol. The key intermediates 3-substituted phenyl-1H-pyrazole-5-carbaldehydes 5(a-l) were prepared in four sequential steps. Initially substituted acetophenones 1(a-l) reacted with diethyl oxalate in the presence of sodium ethanolate in ethanol yielded ethyl 2,4-dioxo-4-(substituted phenyl)butanoates 2(a-l). This was further cyclised with $NH_2$—$NH_2$.2HCl in ethanol to produce ethyl 3-substituted phenyl-1H-pyrazole-5-carboxylates 3(a-l) in good yields. The obtained carboxylates were reduced to (3-substituted phenyl-1H-pyrazol-5-yl) methanols 4(a-l) by $LiAlH_4$. These were selectively oxidized to 3-substituted phenyl-1H-pyrazole-5-carbaldehydes 5(a-l) by IBX in DMSO.

Scheme 1

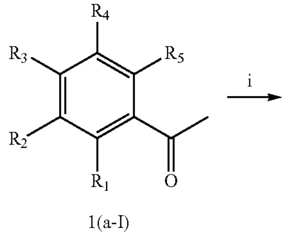

1(a-I)

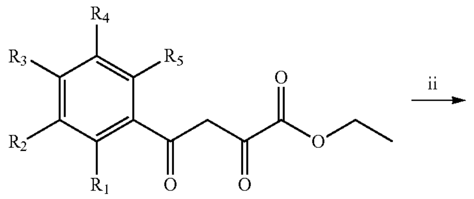

2(a-I)

-continued

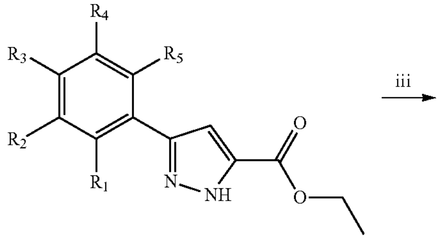

3(a-I)

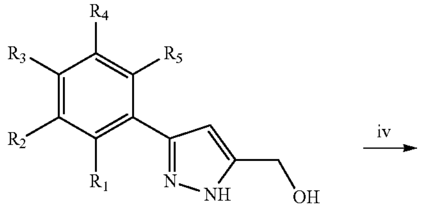

4(a-I)

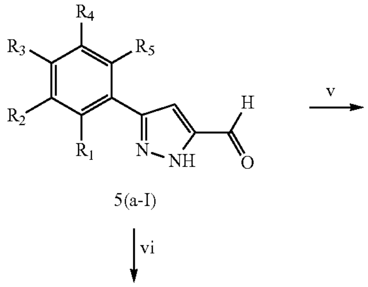

5(a-I)

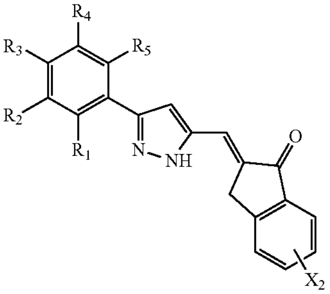

22to24(a-I)

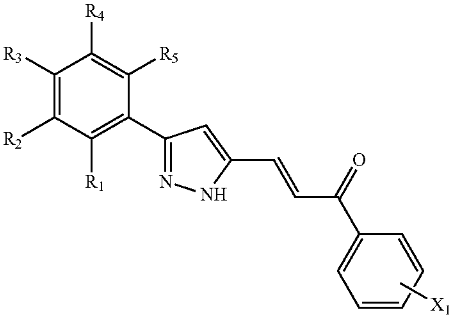

6to21(a-I)

Reagents and conditions (i) NaOEt, EtOH, 8 h, 0° C. then rt, (80-90%); (ii) $NH_2$—$NH_2$.2HCl, EtOH, 4 h, reflux, (72-79%); (iii) $LiAlH_4$, THF, 1 h, 0° C. then rt, (65-70%); (iv) IBX, dry DMSO, 1 h, rt, (80-90%); (v) NaOH/KOH, EtOH/MeOH, acetophenones, 4 h, rt, (50-70%); (vi) NaOH/KOH, EtOH/MeOH, indanones, 2 h, rt, (50-60%).

The present invention further provides a process for the preparation of new pyrazolochalcones of formulae 6a-21a, 6b-21b, 6c-21c, 6d-21d, 6e-21e, 6f-21f, 6g-21g, 6h-21h, 6i-21i, 6j-21j, 6k-21k, 6l-21l and 22a-24a, 22b-24b, 22c-24c, 22d-24d, 22e-24e, 22f-24f, 22g-24g, 22h-24h, 22i-24i, 22j-24j, 22k-24k, 22l-24l which comprises reacting 3-phenyl-1H-pyrazole-5-carbaldehydes of formula 5(a-l) with different acetophenones of formulae a, b, c, d, e, f, g, h, i, j, k, 1, m, n, o, p for synthesis of the compounds (6a-21a to 6l-21l) or q, r, s for synthesis of the compounds (22a-24a to 22l-24l) respectively, in protic water miscible solvent (ethanol or methanol) in the presence of NaOH or KOH at room temperature. The stirring continued for 4h or 2h. Solvent was removed by vacuum evaporation and the resultant residue was neutralized by using dilute HCl and extracted with ethyl acetate followed by evaporation of solvent which resulted in a crude product which was further purified by column chromatography to obtain the desired products of formulae: 6a-21a, 6b-21b, 6c-21c, 6d-21d, 6e-21e, 6f-21f, 6g-21g, 6h-21h, 6i-21i, 6j-21j, 6k-21k, 6k-21l and 22a-24a, 22b-24b, 22c-24c, 22d-24d, 22e-24e, 22f-24f, 22g-24g, 22h-24h, 22i-24i, 22j-24j, 22k-24k, 22l-24l, respectively.

5(a-I)

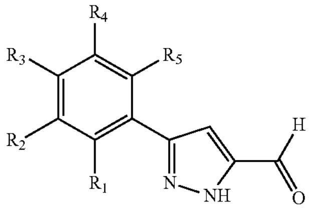

wherein $R_1$, $R_2$, $R_3$, $R_4$, $R_5$=[H, Cl, F, $CH_3$, $OCH_3$,3,4 ($OCH_2O$)]

a

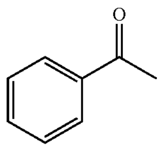

b

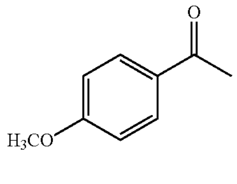

c

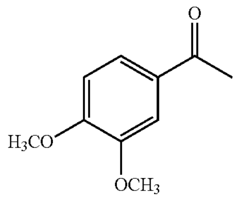

-continued d

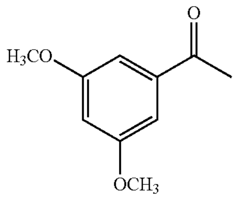

e

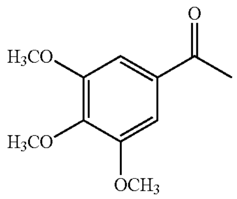

f

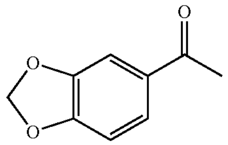

g

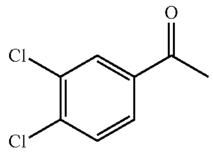

h

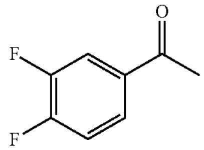

i

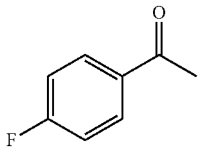

j

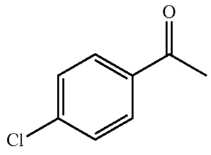

k

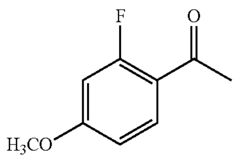

l

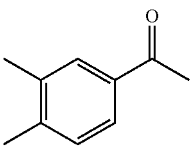

-continued m

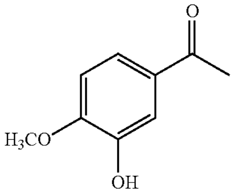

n

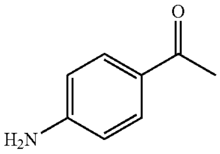

o

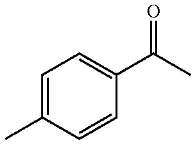

p

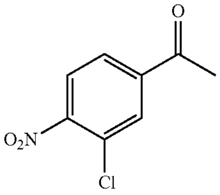

q

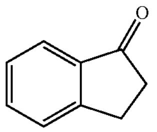

r

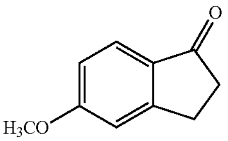

s

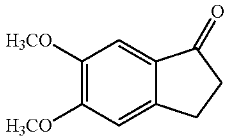

EXAMPLES

The following examples are given by way of illustration and therefore should not be construed to the present limit of the scope of invention.

Example 1

(E)-1-(4-methoxyphenyl)-3-(3-(3,4,5-trimethoxyphenyl)-1H-pyrazol-5-yl)prop-2-en-1-one (7e)

1-(4-methoxyphenyl)ethanone (b) (150 mg, 1.0 mmol) was added to 3-(3,4,5-trimethoxyphenyl)-1H-pyrazole-5-carbaldehyde (5e) (262 mg, 1.0 mmol) in ethanol (10 mL) and catalytic amount (5 mg) of sodium hydroxide (NaOH) to obtain a reaction mixture. The reaction mixture was stirred at 30° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and then the solvent was evaporated to obtain a crude product. The crude product was further purified by column chromatography using ethyl acetate/hexane (3:7) as eluent to obtain the pure compound 7e (210 mg, 53.3% yield).

$^1$H NMR ($CDCl_3$+DMSO): δ 3.77 (s, 3H), 3.88 (s, 9H), 7.13 (s, 4H), 7.40 (d, 1H, J=8.4 Hz), 7.55-7.66 (m, 1H, J=15.8 Hz, trans H), 7.77-7.96 (m, 1H, J=15.8 Hz trans H), 8.10 (d, 2H, J=8.1 Hz), 13.52 (brs, NH) ppm. FABMS: 395. M+H)$^+$.

Example 2

(E)-1-(3,4-dimethoxyphenyl)-3-(3-(3,4,5-trimethoxyphenyl)-1H-pyrazol-5-yl)prop-2-en-1-one (8e)

1-(3,4-dimethoxyphenyl)ethanone (c) (180 mg, 1.0 mmol) was added to 3-(3,4,5-trimethoxyphenyl)-1H-pyrazole-5-carbaldehyde (5e) (262 mg, 1.0 mmol) in ethanol (10 mL) and catalytic amount (5 mg) of sodium hydroxide (NaOH) to obtain a reaction mixture. The reaction mixture was stirred at 29° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (4:6) as eluent to obtain the pure compound 8e (225 mg, 52.9% yield).

$^1$H NMR ($CDCl_3$+DMSO-$d_6$): δ 3.70 (s, 3H), 3.76 (s, 6H), 3.88 (s, 6H), 7.06-7.18 (m, 3H), 7.39 (d, 2H, J=14.9 Hz), 7.56-7.62 (m, 1H), 7.65 (d, 1H, J=7.7 Hz), 7.79-7.97 (m, 2H, J=15.6 Hz) ppm; FABMS: 425M+H)$^+$.

Example 3

(E)-1-(3,4,5-trimethoxyphenyl)-3-(3-(3,4,5-trimethoxyphenyl)-1H-pyrazol-5-yl)prop-2-en-1-one (10e)

1-(3,4,5-trimethoxyphenyl)ethanone (e) (210 mg, 1.0 mmol) was added to 3-(3,4,5-trimethoxyphenyl)-1H-pyrazole-5-carbaldehyde (5e) (262 mg, 1.0 mmol) in ethanol (10 mL) and catalytic amount (5 mg) of sodium hydroxide (NaOH) to obtain a reaction mixture. The reaction mixture was stirred at 32° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (4:6) as eluent to obtain the pure compound 10e (285 mg, 62.7% yield).

$^1$H NMR ($CDCl_3$+DMSO-$d_6$): δ 3.74-4.00 (m, 18H), 6.85 (s, 1H), 6.90 (s, 1H), 7.25 (d, 2H, J=4.7 Hz), 7.36 (s, 1H), 7.55 (d, 1H J=15.8 Hz), 7.76 (d, 1H, J=15.6 Hz) ppm; FABMS: 455M+H)$^+$.

Example 4

(E)-1-(benzo[d][1,3]dioxol-5-yl)-3-(3-(3,4,5-trimethoxyphenyl)-1H-pyrazol-5-yl)prop-2-en-1-one (11e)

1-(benzo[d][1,3]dioxol-5-yl)ethanone (f) (164 mg, 1.0 mmol) was added to 3-(3,4,5-trimethoxyphenyl)-1H-pyrazole-5-carbaldehyde (5e) (262 mg, 1.0 mmol) in ethanol (10 mL) and catalytic amount (5 mg) of sodium hydroxide (NaOH) to obtain a reaction mixture. The reaction mixture was stirred at 30° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (3:7) as eluent to obtain the pure compound 11e (260 mg, 63.6% yield).

$^1$H NMR ($CDCl_3$+DMSO-$d_6$): δ 3.81 (s, 3H), 3.92 (s, 6H), 6.96 (d, 1H, J=13.8 trans H), 7.08 (s, 2H), 7.55 (s, 1H), 7.69 (s, 1H), 7.73 (d, 1H J=16.8 Hz), 7.81-7.85 (m, 1H) ppm; FABMS: 409M+H)$^+$.

Example 5

(E)-1-(3,4-dichlorophenyl)-3-(3-(3,4,5-trimethoxyphenyl)-1H-pyrazol-5-yl)prop-2-en-1-one (12e)

1-(3,4-dichlorophenyl)ethanone (g) (189 mg, 1.0 mmol) was added to 3-(3,4,5-trimethoxyphenyl)-1H-pyrazole-5-carbaldehyde (5e) (262 mg, 1.0 mmol) in ethanol (10 mL) and catalytic amount (5 mg) of sodium hydroxide (NaOH) to obtain a reaction mixture. The reaction mixture was stirred at 32° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (3:7) as eluent to obtain the pure compound 12e (210 mg, 53.3% yield).

$^1$H NMR ($CDCl_3$): □δ 3.85 (s, 3H), 3.94 (s, 6H), 3.99 (s, 3H) 6.89 (s, 1H) 7.06 (s, 2H), 7.12 (d, 1H, J=8.4 Hz), 7.49-7.55 (m, 2H), 7.67-7.95 (m, 2H J=15.4, 16.8 Hz) ppm; FABMS: 434M+H)$^+$.

Example 6

(E)-1-(3,4-difluorophenyl)-3-(3-(3,4,5-trimethoxyphenyl)-1H-pyrazol-5-yl)prop-2-en-1-one (13e)

1-(3,4-difluorophenyl)ethanone (h) (156 mg, 1.0 mmol) was added to 3-(3,4,5-trimethoxyphenyl)-1H-pyrazole-5-carbaldehyde (5e) (262 mg, 1.0 mmol) in ethanol (10 mL) and catalytic amount (5 mg) of sodium hydroxide (NaOH) to obtain a reaction mixture. The reaction mixture was stirred at 28° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (3:7) as eluent to obtain the pure compound 13e (280 mg, 69.9% yield).

$^1$H NMR ($CDCl_3$+DMSO-$d_6$): δ3.83 (s, 6H), 3.84 (s, 3H), 5.90 (s, 1H) 6.19 (s, 1H) 6.54 (s, 1H), 6.85-7.02 (m, 1HJ=16.6 Hz), 7.06-7.16 (m, 1H), 7.23-7.33 (m, 2H), 7.33-7.55 (m, 1H J=16.8 Hz) ppm; FABMS: 401M+Hr.

Example 7

(E)-3-(3-(benzo[d][1,3]dioxol-5-yl)-1H-pyrazol-5-yl)-1-(3,4-dimethoxyphenyl)prop-2-en-1-one (8f)

1-(3,4-dimethoxyphenyl)ethanone (c) (180 mg, 1.0 mmol) was added to 3-(benzo[d][1,3]dioxol-5-yl)-1H-pyrazole-5-carbaldehyde (5f) (216 mg, 1.0 mmol) in ethanol (10 mL) and catalytic amount (5 mg) of sodium hydroxide (NaOH) to obtain a reaction mixture. The reaction mixture was stirred at 34° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (4:6) as eluent to obtain the pure compound 8f (262 mg, 69.2% yield).

$^1$H NMR ($CDCl_3$+DMSO-$d_6$): δ 3.86 (s, 3H), 3.89 (s, 3H), 6.07 (s, 2H), 6.94-7.08 (m, 1H), 7.15 (d, 1H, J=8.4), 7.25-7.38 (m, 2H J=16.8), 7.54-7.64 (m, 2H J=15.4, 16.8 Hz), 7.84 (d, 2H J=8.4 Hz), 13.45 (brs, NH) ppm; FABMS: 379M+H)$^+$.

Example 8

(E)-5-methoxy-2-((3-(3,4,5-trimethoxyphenyl)-1H-pyrazol-5-yl)methylene)-2,3-dihydro-1H-inden-1-one (23e)

5-methoxy-2,3-dihydro-1H-inden-1-one (r) (162 mg, 1.0 mmol) was added to 3-(3,4,5-trimethoxyphenyl)-1H-pyrazole-5-carbaldehyde (5e) (262 mg, 1.0 mmol) in ethanol (10 mL) and catalytic amount (5 mg) of sodium hydroxide (NaOH) to obtain a reaction mixture. The reaction mixture was stirred at 35° C. for 2 h and the reaction was monitored by TLC using ethyl acetate/hexane (4:6) as a solvent system. This solution was then evaporated by vacuum distillation and the residue was neutralized with dil.

HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (4:6) as eluent to obtain the pure compound 23e (274 mg, 67.4% yield).

$^1$H NMR ($CDCl_3$): δ=1.25 (s, 2H), 2.36 (s, 3H), 3.94 (s, 6H), 4.01 (s, 3H), 6.80 (s, 1H), 6.91-6.99 (m, 1H), 7.07 (s, 2H) 7.57 (d, 2H, J=8.4 Hz) ppm; FABMS: 407M+H)$^+$.

Example 9

(E)-1-(4-aminophenyl)-3-(3-(3,4,5-trimethoxyphenyl)-1H-pyrazol-5-yl)prop-2-en-1-one (19e)

1-(4-aminophenyl)ethanone (n) (135 mg, 1.0 mmol) was added to 3-(3,4,5-trimethoxyphenyl)-1H-pyrazole-5-carbaldehyde (5e) (262 mg, 1.0 mmol) in ethanol (10 mL) and catalytic amount (5 mg) of sodium hydroxide (NaOH) to obtain a reaction mixture. The reaction mixture was stirred at 28° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (3:7) as eluent to obtain the pure compound 19e (264 mg, 64.8% yield).

$^1H$ NMR ($CDCl_3$): δ 3.77 (s, 3H), 3.85 (s, 6H), 4.74 (brs, NH), 6.62 (d, 2H, J=8.9 Hz), 6.75 (s, 1H), 6.97 (s, 2H) 7.37 (s, 1H) 7.55-7.66 (m, 2H, J=15.8 Hz), 7.84 (d, 2H, J=8.4 Hz) ppm; FABMS: 380M+H)$^+$.

Example 10

(E)-1-(benzo[d][1,3]dioxol-5-yl)-3-(3-(benzo[d][1,3]dioxol-5-yl)-1H-pyrazol-5-yl)prop-2-en-1-one (11f)

1-(benzo[d][1,3]dioxol-5-yl)ethanone (f) (164 mg, 1.0 mmol) was added to 3-(benzo[d][1,3]dioxol-5-yl)-1H-pyrazole-5-carbaldehyde (5f) (216 mg, 1.0 mmol) in ethanol (10 mL) and catalytic amount (5 mg) of sodium hydroxide (NaOH) to obtain a reaction mixture. The reaction mixture was stirred at 30° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (3:7) as eluent to obtain the pure compound 11f (227 mg, 62.6% yield).

$^1H$ NMR ($CDCl_3$+DMSO-d6): δ 6.03 (s, 2H), 6.13 (s, 2H), 6.87 (d, 1H J=8.0 Hz), 6.99 (d, 1H, J==8.4), 7.03 (s, 1H), 7.30 (d, 1H, J=8.1 Hz), 7.56 (s, 1H), 7.64 (d, 1H, J=15.4 Hz), 7.72-7.79 (m, 2H, J=15.2 Hz) 8.04 (s, 1H) ppm; FABMS: 363M+H)$^+$.

Example 11

(E)-3-(3-(4-methoxyphenyl)-1H-pyrazol-5-yl)-1-(3,4,5-trimethoxyphenyl)prop-2-en-1-one (10b)

1-(3,4,5-trimethoxyphenyl)ethanone (e) (210 mg, 1.0 mmol) was added to 3-(4-methoxyphenyl)-1H-pyrazole-5-carbaldehyde (5b) (202 mg, 1.0 mmol) in methanol (10 mL) and catalytic amount (5 mg) of potassium hydroxide (KOH) to obtain a reaction mixture. The reaction mixture was stirred at 34° C. for 4 h and the reaction was monitored by TLC using ethyl acetate/hexane (3:7) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (3:7) as eluent to obtain the pure compound 10b (250 mg, 64.7% yield).

$^1H$ NMR ($CDCl_3$+DMSO-d6): δ 3.75 (s, 3H), 3.80 (s, 3H), 3.87 (s, 6H), 6.81 (s, 1H), 6.86 (d, 2H) J=8.4 Hz), 7.26 (s, 2H), 7.55-7.69 (m, 4H, J=15.8 Hz J=8.4 Hz) ppm; FABMS: 395M+H)$^+$.

Example 12

(E)-3-(3-(3,4-dimethoxyphenyl)-1H-pyrazol-5-yl)-1-(3,4,5-trimethoxyphenyl)prop-2-en-1-one (10c)

1-(3,4,5-trimethoxyphenyl)ethanone (e) (210 mg, 1.0 mmol) was added to 3-(3,4-dimethoxyphenyl)-1H-pyrazole-5-carbaldehyde (5c) (202 mg, 1.0 mmol) in methanol (10 mL) and catalytic amount (5 mg) of potassium hydroxide (KOH) to obtain a reaction mixture. The reaction mixture was stirred at 35° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (3:7) as eluent to obtain the pure compound 10c (280 mg, 66% yield).

$^1H$ NMR ($CDCl_3$+DMSO-d6): δ 3.92 (s, 3H), 3.93 (s, 3H), 3.97 (s, 6H), 6.86 (s, 1H), 6.94 (d, 1H) J=8.3 Hz), 7.31-7.42 (m, 3H), 7.42-7.53 (m, 2H), 7.65 (d, 1H, trans J=15.8 Hz), 7.79 (d, 1H, trans J=15.8 Hz) ppm; FABMS: 425M+H)$^+$.

Example 13

(E)-1-(4-aminophenyl)-3-(3-(benzo[d][1,3]dioxol-5-yl)-1H-pyrazol-5-yl)prop-2-en-1-one (19f)

1-(4-aminophenyl)ethanone (n) (135 mg, 1.0 mmol) was added to 3-(benzo[d][1,3]dioxol-5-yl)-1H-pyrazole-5-carbaldehyde (5f) (216 mg, 1.0 mmol) in ethanol (10 mL) and catalytic amount (5 mg) of potassium hydroxide (KOH) to obtain a reaction mixture. The reaction mixture was stirred at 30° C. for 4 h and the reaction was monitored by TLC using ethyl acetate/hexane (3:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (3:7) as eluent to obtain the pure compound 19f (210 mg, 63% yield).

$^1H$ NMR ($CDCl_3$+DMSO-d6): δ 5.51 (brs, 2H), 6.02 (s, 2H), 6.69 (d, 2H, J=8.3 Hz), 6.8-6.94 (m, 2H), 7.24-7.36 (m, 2H), 7.65 (d, 1H, trans J=15.8 Hz), 7.70 (d, 1H, trans J=15.8 Hz) 7.81 (s, 1H), 7.88 (d, 1H, J=8.6 Hz) ppm; FABMS: 333M+H)$^+$.

Example 14

(E)-3-(3-(benzo[d][1,3]dioxol-5-yl)-1H-pyrazol-5-yl)-1-(3,4,5-trimethoxyphenyl)prop-2-en-1-one (10f)

1-(3,4,5-trimethoxyphenyl)ethanone (e) (210 mg, 1.0 mmol) was added to 3-(benzo[d][1,3]dioxol-5-yl)-1H-pyrazole-5-carbaldehyde (5f) (216 mg, 1.0 mmol) in methanol (10 mL) and catalytic amount (5 mg) of sodium hydroxide (NaOH) to obtain a reaction mixture. The reaction mixture was stirred at 34° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (3:7) as eluent to obtain the pure compound 10f (225 mg, 55% yield).

$^1$H NMR ($CDCl_3$+DMSO-d6): δ 3.9 (s, 3H), 3.96 (s, 6H), 6.01 (s, 2H), 6.82-6.92 (m, 2H), 7.27-7.37 (m, 3H, $J_1$=8.3 Hz, trans $J_2$=15.8 Hz), 7.66-7.76 (m, 2H, $J_j$=8.3 Hz, trans $J_2$=15.8 Hz) ppm; FABMS: 409M+H)$^+$.

Example 15

(E)-1-(3,4-dimethoxyphenyl)-3-(3-(4-methoxyphenyl)-1H-pyrazol-5-yl)prop-2-en-1-ine (8b)

1-(3,4-dimethoxyphenyl)ethanone (c) (180 mg, 1.0 mmol) was added to 3-(4-methoxyphenyl)-1H-pyrazole-5-carbaldehyde (5b) (202 mg, 1.0 mmol) in ethanol (10 mL) and catalytic amount (5 mg) of sodium hydroxide (NaOH) to obtain a reaction mixture. The reaction mixture was stirred at 30° C. for 4 h and the reaction was monitored by TLC using ethyl acetate/hexane (4:6) as a solvent system. This solution was then evaporated by vacuum distillation and the residue was neutralized with dil. HCl solution which was further extracted with ethyl acetate (25 mL×4). The organic solution was dried over anhydrous $Na_2SO_4$ and the solvent was evaporated to obtain a crude product. The crude product was further purified by column chromatography using ethyl acetate/hexane (3:7) as eluent to obtain the pure compound 8b (215 mg, 59% yield).

$^1$H NMR ($CDCl_3$+DMSO-d6): δ 3.76 (s, 3H), 3.87 (s, 6H), 6.76-6.90 (m, 3H), 6.90-6.99 (m, 1H), 7.53 (s, 1H), 7.58-7.75 (m, 4H, $J_1$=8.4 Hz, trans $J_2$=15.8 Hz), 7.83 (s, 1H) ppm; FABMS: 365M+H)$^+$.

Anticancer Activity:

Some of in vitro biological activity studies were carried out at the National Cancer Institute, Maryland, USA.

In Vitro Cytotoxicity

The pyrazolochalcones (7e, 8e, 10e, 11e, 12e, 13e and 8f) have been tested against fifty nine human tumor cell lines derived from nine cancer types (leukemia, non-small cell lung cancer, colon cancer, CNS cancer, melanoma, ovarian cancer, renal cancer, prostate cancer and breast cancer) as per the NCI protocol. For each compound, dose response curves for individual cell lines have been measured at a minimum of five concentrations at 10 fold dilutions. A protocol of 48 h continuous drug exposure has been used, and a sulforhodamine B (SRB) protein assay has been used to estimate cell viability or growth. The concentration for 50% cell growth inhibition ($GI_{50}$), 50% cell death ($LC_{50}$, 50% growth) and total cell growth inhibition (TGI, 0% growth) values were tabulated (Table-1). DMSO was used as control to calculate the values of $GI_{50}$, $LC_{50}$ and TGI. The compounds 7e, 8e, 10e, 11e, 12e, 13e and 8f has been evaluated for their in vitro cytotoxicity in sixty cell lines from nine human cancer types of leukemia (K-562, SR), non-small cell lung (Hop-62, NCI-H226, NCI-H522), colon (HCT-116, HCT-15, HCC-2998), CNS (SF-539), melanoma (SK-MEL-5, UACC-62, M14), ovarian (IGROV1), renal (A498), prostate (PC3) and breast (BT-549, MDA-MB-435, HS578T) origin. The results are expressed as percent of cell growth determined relative to that of untreated control cells (Table 2). The representative compounds 7e, 8e, 10e, 11e, 12e, 13e and 8f showed significant cytotoxicity against some cancer cell lines.

TABLE 1

$Log_{10}$ $GI_{50}$ (concentration in mol/L causing 50% growth inhibition) and $Log_{10}$ $LC_{50}$ (concentration in mol/L causing 50% cell death) and $Log_{10}$ TGI (concentration in mol/L causing 0% growth inhibition) values for pyrazolochalcones (7e, 8e, 10e, 11e, 12e, 13e and 8f)

| | $Log_{10}$ $GI_{50}$ | | | | | | | $Log_{10}$ $LC_{50}$ | | | |
|---|---|---|---|---|---|---|---|---|---|---|---|
| Cell Lines | 7e | 8e | 10e | 11e | 12e | 13e | 8f | 7e | 8e | 10e | 11e |
| Leukemia | −5.92 | −6.1 | −5.92 | −4.91 | −5.68 | −5.57 | −5.69 | −4 | −4.01 | −4 | −4 |
| Non-small cell lung | −5.74 | −5.91 | −5.89 | −4.27 | −5.18 | −5.54 | −5.6 | −4.66 | −5.19 | −4.87 | −4.27 |
| Colon | −5.76 | −5.85 | −5.79 | −4.66 | −5.32 | −5.52 | −5.52 | −4.72 | −5.21 | −5.22 | −4.66 |
| CNS | −5.78 | −5.85 | −5.79 | −4.2 | −5.07 | −5.47 | −5.65 | −4.61 | −5.21 | −5.1 | −4.2 |
| Melanoma | −5.68 | −5.77 | −5.77 | −4.14 | −4.88 | −5.56 | −5.79 | −4.44 | −5.21 | −5.19 | −4.14 |
| Ovarian | −5.62 | −5.68 | −5.66 | −4 | −5 | −5.5 | −5.58 | −4.32 | −4.82 | −4.84 | −4 |
| Renal | −5.74 | −5.82 | −5.8 | −4.37 | −5.05 | −5.56 | −5.46 | −4.74 | −5.18 | −5.12 | −4.37 |
| Prostate | −5.83 | −6.06 | −5.83 | −4 | −5.23 | −5.78 | −5.66 | NT | −5.28 | −5.13 | −4 |
| Breast | −5.72 | −5.91 | −5.87 | −3.53 | −5.35 | −5.56 | −4.76 | −4.47 | −4.82 | −5 | −3.53 |

| | $Log_{10}$ $LC_{50}$ | | | $Log_{10}$ TGI | | | | | | |
|---|---|---|---|---|---|---|---|---|---|---|
| Cell Lines | 12e | 13e | 8f | 7e | 8e | 10e | 11e | 12e | 13e | 8f |
| Leukemia | −4 | −4 | −4 | −5.18 | −5.19 | −4.80 | −5.00 | −4.61 | −4.76 | −5.03 |
| Non-small cell lung | −3.7 | −4.06 | −3.29 | −5.36 | −5.58 | −5.42 | −4.70 | −4.52 | −4.75 | −5.08 |
| Colon | −4 | −4.23 | −3.17 | −5.41 | −5.52 | −5.50 | −5.33 | −4.34 | −4.70 | −4.85 |
| CNS | −4.06 | −4.04 | −3.81 | −5.46 | −5.53 | −5.46 | −4.83 | −4.25 | −4.38 | −5.14 |
| Melanoma | −4.02 | −4.19 | −2.98 | −5.32 | −5.49 | −5.47 | −4.52 | −4.21 | −5.00 | −4.80 |
| Ovarian | −4.02 | −4.05 | −4.28 | −5.15 | −5.29 | −5.23 | −4.38 | −4.27 | −4.45 | −4.87 |
| Renal | −4.03 | −4.03 | −4.49 | −5.43 | −5.51 | −5.45 | −4.94 | −4.22 | −4.71 | −5.01 |
| Prostate | −4 | −4 | −4.5 | −5.55 | −5.64 | −5.48 | −4.94 | −4.00 | −5.24 | −5.05 |
| Breast | −4 | −4.01 | −4.4 | −5.08 | −5.47 | −5.35 | −4.60 | −4.41 | −4.83 | −5.05 |

Each cancer type represents the average of six to eight different cancer cell lines.

The compounds 7e, 8e, 10e, 11e, 12e, 13e and 8f exhibited a wide spectrum of activity against fifty nine cell lines in nine cell panels, with $GI_{50}$ value range of 0.18-29.2 μM. Particularly, the compounds 7e, 8e, and 10e were more potent than the compounds 8f, 11e, 12e, 13e, against all the tested cell lines. In detail, the $GI_{50}$ values for the compound 7e against leukemia SR, RPMI-8226, and CCRF-CEM cell lines were 0.34, 0.43 and 1.42 μM, respectively. In the non-small cell lung cancer panel, the growth of HOP-62 and HOP92 cell lines were affected by compound 7e with $GI_{50}$ values as 1.76 and 1.06 μM, respectively. The $GI_{50}$ value for the compound 8e against non-small lung cancer cell line NCI-H522 is 0.18 μM, whereas the colon cancer cell line HCT-116 affected by compound 8e has $GI_{50}$ value of 0.88 μM. The $GI_{50}$ values for compound 8e against breast MCF7 and MDA-MB-435 cell lines were 0.82 and 0.75 μM, respectively. In the leukemia cancer panel the cell lines CCRF-CEM, RPMI-8226 and SR were affected by 8e with $GI_{50}$ values 0.62, 0.24 and 0.27 μM, respectively and the $GI_{50}$ values for the compound 8e against prostate cancer cell line DU-145 is 0.55 μM. In the non-small cell lung cancer panel, the growth of HOP-92 and NCI-H522 cell lines were affected by compound 10e with $GI_{50}$ values as 0.86 and 0.52 μM, respectively. The $GI_{50}$ values for the compound 10e against leukemia RPMI-8226 and SR are 0.31 and 0.39 μM, respectively, whereas in the breast cancer cell line MCF-7, the growth was affected by 10e with $GI_{50}$ value 0.64 μM. The $GI_{50}$ values for the compound 11e against leukemia RPMI-8226 and SR are 0.51 and 0.55 μM, respectively. In the non-small cell lung cancer panel, the growth of NCI-H522 cell line was affected by compound 11e and 12e with $GI_{50}$ values 1.03 and 1.33 μM, respectively. The $GI_{50}$ values for the compound 12e against leukemia RPMI-8226 and SR are 0.53 and 0.39 μM, respectively. The $GI_{50}$ values for the compounds 13e and 8f against non-small cell lung cancer panel, the growth of NCI-H522 cell line were 1.57 and 1.82 μM, respectively. The $GI_{50}$ values for the compound 8f against leukemia RPMI-8226 and SR were 1.03 and 1.27 μM, respectively. Overall, the growth affected by the compounds 7e, 8e, and 10e against all the cancer cell lines with $GI_{50}$ values range 0.18-4.14 μM.

Compounds 7e, 8e, 10e, 11e, 12e, 13e and 8f exhibited activity against fifty nine cell lines in nine cancer cell panels with $GI_{50}$ values of <29.2 μm. In vitro cytotoxicity of compounds 7e, 8e, 10e, 11e, 12e, 13e and 8f in the selected cancer cell lines has been illustrated in Table 2. The average $GI_{50}$ values for each cancer panel of compounds 7e, 8e, 10e, 11e, 12e, 13e and 8f have been illustrated in Table 2.

TABLE 2

In vitro cytotoxicity of compounds 7e, 8e, 10e, 11e, 12e, 13e and 8f in a panel of fifty nine cancer cell lines.

| Cancer panel/ | $GI_{50}$ (μM) | | | | | | |
|---|---|---|---|---|---|---|---|
| cell line | 7e | 8e | 10e | 11e | 12e | 13e | 8f |
| Leukemia | | | | | | | |
| CCRF-CEM | 1.42 | 0.62 | 1.68 | 1.57 | 2.15 | 3.80 | 2.52 |
| HL-60(TB) | 2.16 | 1.44 | 1.93 | 2.17 | 7.18 | 2.48 | 2.82 |
| K-562 | 2.32 | 1.91 | 2.96 | 3.20 | 4.96 | 3.31 | 2.47 |
| MOLT-4 | 2.67 | 2.11 | 2.32 | 2.98 | 4.38 | 2.72 | 3.00 |
| RPMI-8226 | 0.43 | 0.24 | 0.31 | 0.51 | 0.53 | 1.76 | 1.03 |
| SR | 0.34 | 0.27 | 0.39 | 0.55 | 0.39 | 2.92 | 1.27 |

TABLE 2-continued

In vitro cytotoxicity of compounds 7e, 8e, 10e, 11e, 12e, 13e and 8f in a panel of fifty nine cancer cell lines.

| Cancer panel/ | $GI_{50}$ (μM) | | | | | | |
|---|---|---|---|---|---|---|---|
| cell line | 7e | 8e | 10e | 11e | 12e | 13e | 8f |
| Non-small cell lung | | | | | | | |
| A549/ATCC | 2.27 | 1.86 | 2.72 | 4.32 | 18.7 | 2.43 | 2.70 |
| HOP-62 | 1.76 | 1.44 | 1.46 | 2.18 | 1.72 | 4.39 | 2.08 |
| HOP92 | 1.06 | NT | 0.86 | NT | 2.53 | NT | 2.16 |
| NCI-H226 | 1.89 | 1.69 | 1.60 | 3.31 | 18.6 | 3.72 | 3.40 |
| NCI-H23 | 3.04 | 2.15 | 3.04 | 2.02 | 23.4 | 2.60 | 4.12 |
| NCIH322M | 1.92 | 1.52 | 2.00 | 3.01 | 14.5 | 3.37 | 2.48 |
| NCI-H460 | 1.72 | 1.41 | 1.89 | 2.12 | 4.9 | 2.96 | 1.81 |
| NCI-H522 | 1.47 | 0.18 | 0.52 | 1.03 | 1.33 | 1.57 | 1.82 |
| Colon | | | | | | | |
| COLO-205 | 1.73 | 1.74 | 1.75 | 1.87 | 1.26 | 1.69 | 3.84 |
| HCC-2998 | 1.78 | 2.13 | 1.83 | 1.95 | 9.56 | 3.69 | 4.99 |
| HCT-116 | 1.73 | 0.88 | 1.31 | 1.85 | 2.95 | 4.00 | 2.43 |
| HCT-15 | 1.58 | 1.27 | 1.50 | 2.12 | 4.29 | 3.01 | 2.81 |
| HT29 | 1.97 | 1.62 | 1.79 | 2.18 | 1.15 | 2.62 | 2.98 |
| KM12 | 1.56 | 1.07 | 1.49 | 1.76 | 3.37 | 3.06 | 2.86 |
| SW-620 | 1.62 | 1.37 | 1.59 | 2.47 | 8.63 | 3.42 | 2.05 |
| CNS | | | | | | | |
| SF-268 | 1.99 | 1.82 | 1.94 | 2.97 | 13.7 | 3.15 | 2.53 |
| SF-295 | NT | NT | NT | NT | NT | NT | 2.51 |
| SF-539 | 1.62 | 1.27 | 1.29 | 2.07 | 4.31 | 3.76 | 1.91 |
| SNB-19 | 1.51 | 1.42 | 1.66 | 4.30 | 9.83 | 3.64 | 3.20 |
| SNB-75 | 1.49 | 1.23 | 1.54 | 2.01 | 8.70 | 2.90 | 1.98 |
| U251 | NT | NT | NT | NT | NT | NT | 1.58 |
| Melanoma | | | | | | | |
| LOX IMVI | 1.58 | 1.38 | 1.52 | 1.82 | 3.39 | 3.18 | 1.97 |
| MALME-3M | 1.86 | 1.99 | 1.86 | 4.42 | 29.2 | 2.96 | 7.32 |
| M14 | 2.20 | 1.84 | 1.79 | 3.86 | 18.2 | 2.70 | 6.36 |
| MDA-MB-435 | 2.20 | 1.34 | 1.49 | 2.39 | 5.65 | 2.88 | 3.03 |
| SK-MEL-2 | 4.14 | 1.85 | 1.96 | 10.3 | 13.9 | 2.30 | 6.93 |
| SK-MEL-28 | 2.12 | 1.78 | 1.82 | 2.48 | 18.5 | 5.31 | 5.76 |
| SK-MEL-5 | 1.72 | 1.65 | 1.57 | 4.51 | 13.4 | 2.27 | 6.74 |
| UACC-257 | 1.75 | 1.49 | 1.57 | 2.46 | 16.3 | 1.75 | 7.06 |
| UACC-62 | 1.85 | 1.74 | 1.78 | 4.67 | 18.8 | 2.38 | 4.10 |
| Ovarian | | | | | | | |
| IGROV1 | 2.21 | 1.80 | 3.14 | 5.00 | 24.0 | 3.62 | 2.79 |
| OVCAR-3 | 1.74 | 1.68 | 1.75 | 3.38 | 6.99 | 2.39 | 2.02 |
| OVCAR-4 | 2.20 | 2.69 | 1.45 | 3.80 | 10.8 | 2.20 | 2.11 |
| OVCAR-5 | 1.88 | 1.59 | 1.64 | 3.37 | 20.5 | 4.48 | 3.36 |
| OVCAR-8 | 2.43 | 1.32 | 1.58 | 2.85 | 6.30 | 2.88 | 2.15 |
| NCI/ADR-RES | 2.7 | 3.13 | 3.47 | 4.23 | 10.6 | 3.46 | NT |
| SK-OV-3 | 3.99 | 2.79 | 3.20 | 5.76 | 4.19 | 3.53 | 3.97 |
| Renal | | | | | | | |
| 786-0 | 1.95 | 1.40 | 1.56 | 2.33 | 10.1 | 3.35 | 3.12 |
| A498 | 1.74 | 1.48 | 1.61 | 2.76 | 5.89 | 2.11 | 1.55 |
| ACHN | 1.96 | 1.66 | 1.62 | 1.88 | 21.4 | 3.26 | 3.49 |
| CAKI-1 | 2.34 | 2.20 | 2.58 | 5.51 | 16.9 | 2.98 | 1.90 |
| RXF 393 | 1.27 | 1.35 | 1.26 | 1.48 | 2.70 | 2.05 | 2.42 |
| SN12C | 1.81 | 1.54 | 1.47 | 3.94 | 13.7 | 3.37 | 3.25 |
| TK-10 | 2.22 | 1.33 | 1.46 | 2.33 | 8.34 | 2.29 | 2.8 |
| UO-31 | 1.45 | 1.28 | 1.19 | 1.91 | 5.73 | 2.63 | 2.3 |
| Prostate | | | | | | | |
| PC-3 | 1.51 | 1.36 | 1.47 | 2.81 | 5.95 | 1.66 | 2.5 |
| DU-145 | 1.43 | 0.55 | NT | 2.72 | NT | NT | 1.8 |
| Breast | | | | | | | |
| MCF7 | 1.15 | 0.82 | 0.64 | 1.67 | 1.80 | 3.20 | 3.2 |
| MDA-MB-231/ATCC | 1.88 | 1.48 | 1.52 | 3.50 | 8.65 | 1.64 | 2.4 |
| HS 578T | 3.60 | 2.57 | 2.68 | 3.71 | 16.6 | 3.58 | 2.6 |
| BT-549 | 1.86 | 1.44 | 1.57 | 2.37 | 8.40 | 4.11 | 1.9 |
| T-47D | 2.31 | 1.63 | 1.13 | 2.51 | 1.66 | 2.45 | 3.2 |
| MDA-MB-435 | 1.29 | 0.75 | 1.15 | 1.40 | 1.98 | 2.22 | 1.8 |

*NT = not tested

The mean graph midpoint values of $Log_{10}$ TGI and $Log_{10}$ $LC_{50}$ as well as $Log_{10}$ $GI_{50}$ for compounds 7e, 8e, 10e, 11e, 12e, 13e and 8f is listed in Table-3. As demonstrated by mean graph pattern, compounds 7e, 8e, 10e, 11e, 12e, 13e and 8f exhibited an interesting profile of activity and selectivity for various cell lines. The mean graph mid points of $Log_{10}$ TGI and $Log_{10}$, $LC_{50}$ have shown similar pattern to the $log_{10}$ $GI_{50}$ mean graph mid points.

TABLE 3

$Log_{10}$ $GI_{50}$, $Log_{10}$ TGI and $Log_{10}$ $LC_{50}$ mean graphs midpoints (MG_MID) of in vitro cytotoxicity data for the compound 7e, 8e, 10e, 11e, 12e, 13e and 8f against human tumor cell lines.

| Compound | $Log_{10}$ $GI_{50}$ | $Log_{10}$ TGI | $Log_{10}$ $LC_{50}$ |
|---|---|---|---|
| 7e | −5.75 | −5.31 | −4.47 |
| 8e | −5.87 | −5.47 | −4.98 |
| 10e | −5.81 | −5.36 | −4.94 |
| 11e | −5.57 | −4.77 | −4.21 |
| 12e | −5.18 | −4.35 | −4.05 |
| 13e | −5.55 | −4.74 | −4.09 |
| 8f | −5.56 | −4.98 | −4.36 |

SIGNIFICANCE OF THE WORK CARRIED OUT

The new pyrazolochalcones that have been synthesized exhibited significant cytotoxicity against fifty nine human tumor cell lines.

ADVANTAGES OF THE INVENTION

1. The present invention provides a new pyrazolochalcones useful as antitumor agents.

2. It also provides a process for the preparation of novel pyrazolochalcones.

We claim:

1. A pyrazolochalcone selected from the group consisting of:

6a

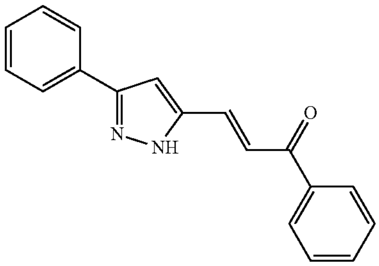

;

6b

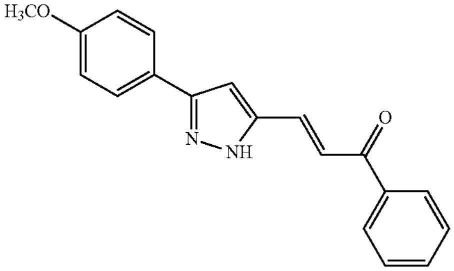

;

-continued

6c

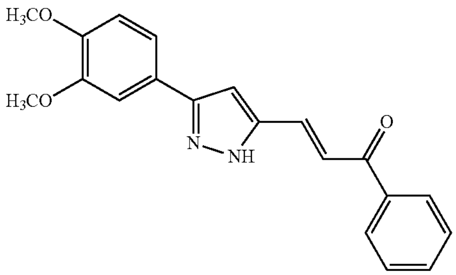

;

6d

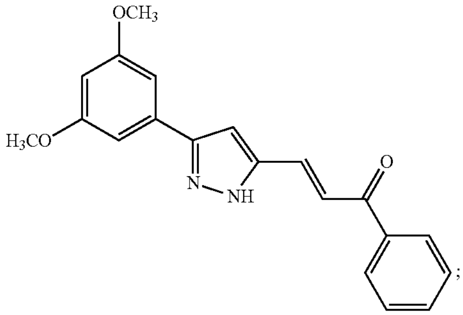

;

6e

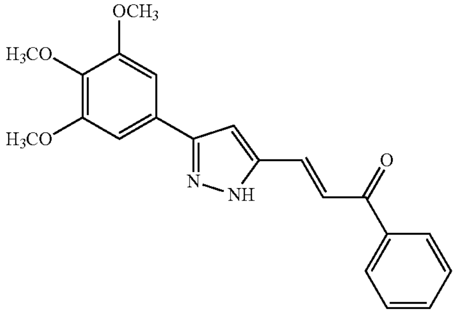

;

6f

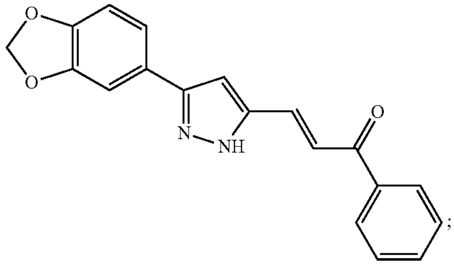

;

6g

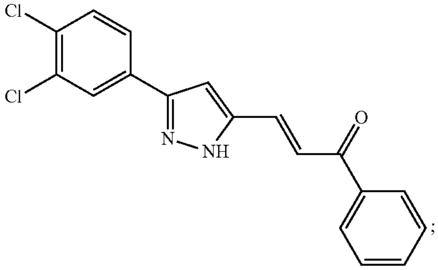

;

-continued
6h
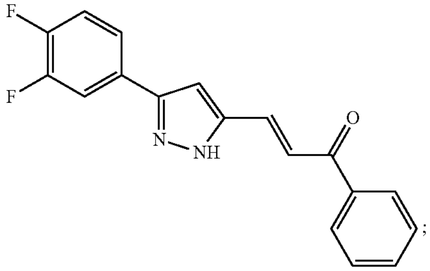
6i
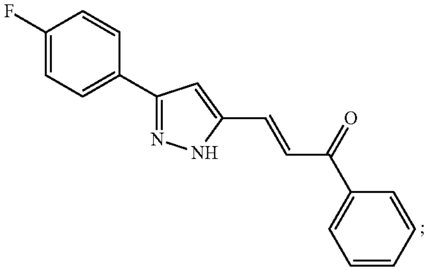
6j
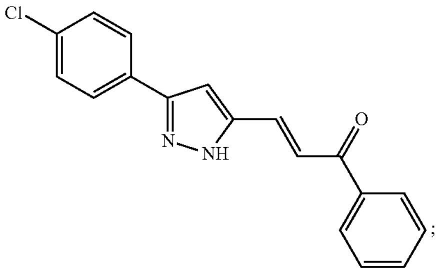
6k
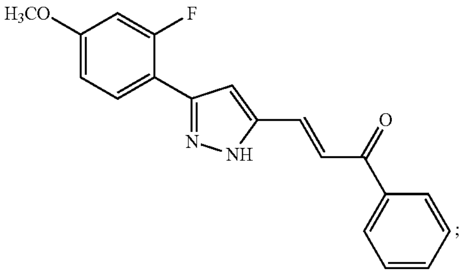
6l
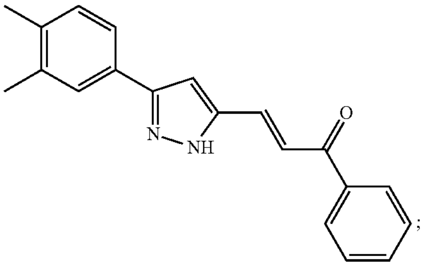
-continued
7a
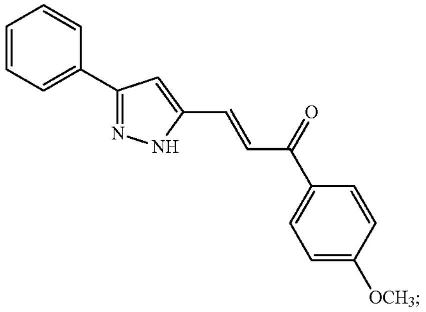
7b
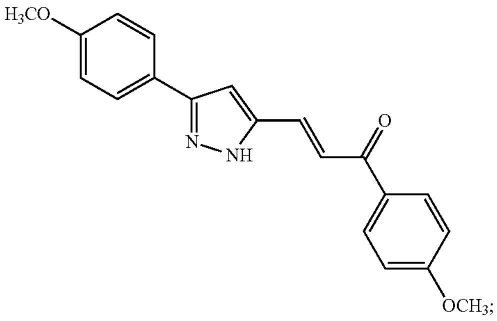
7c
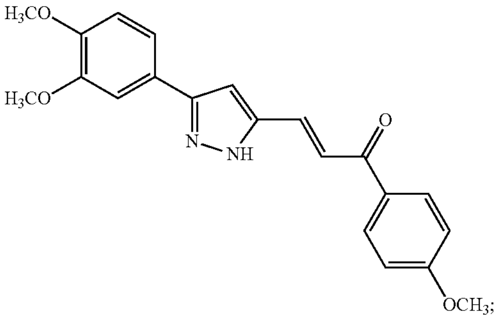
7d
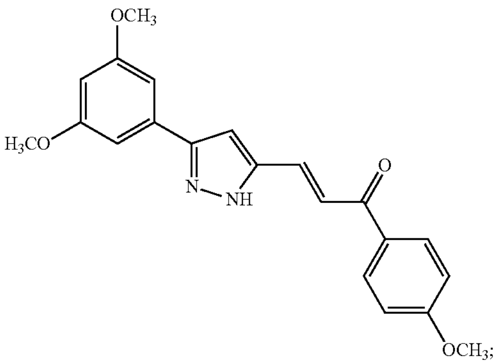

-continued
7e
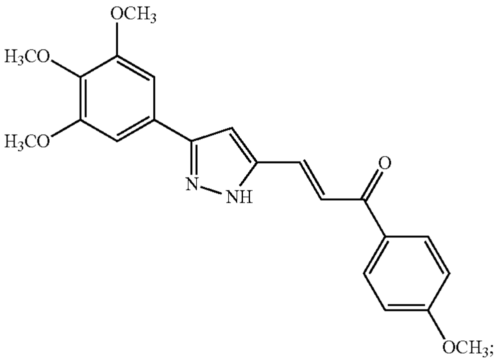
7f
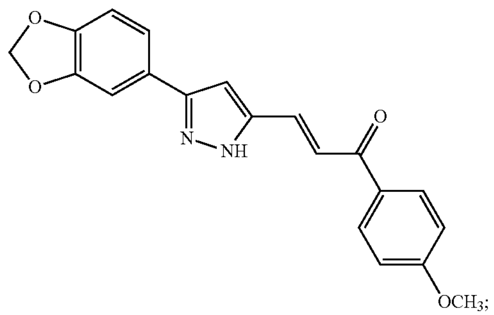
7g
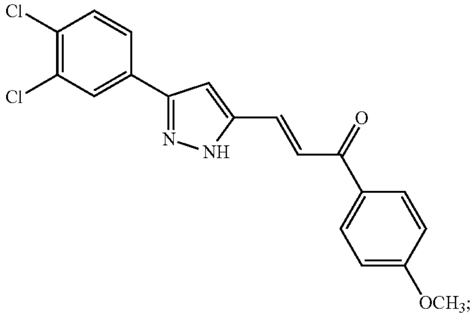
7h
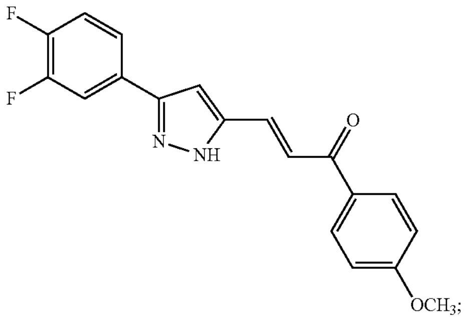
-continued
7i
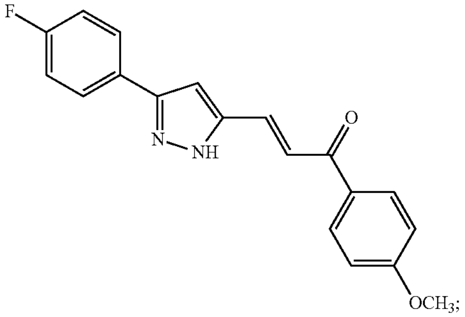
7j
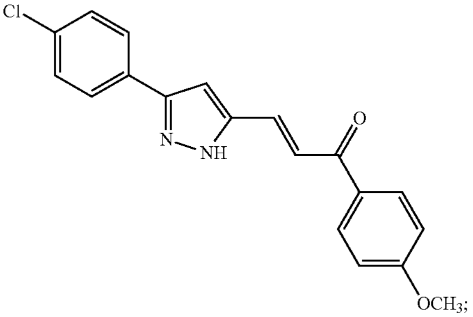
7k
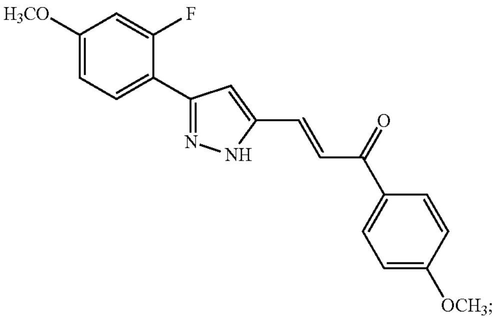
7l
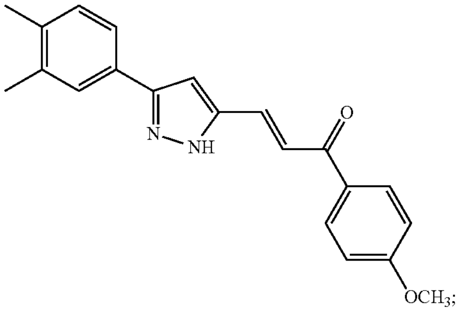
14a
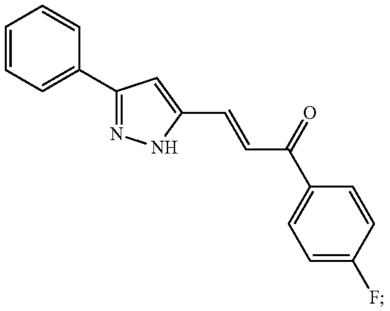

-continued
14b
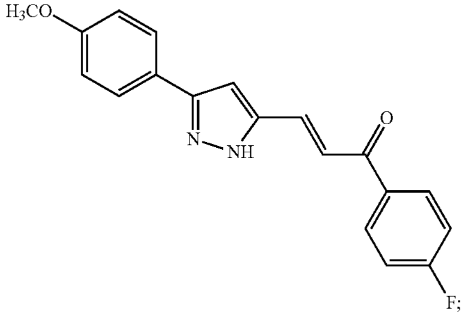
14c
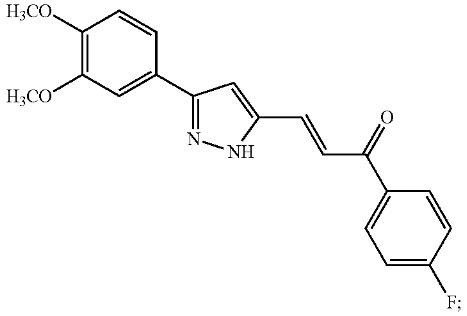
14d
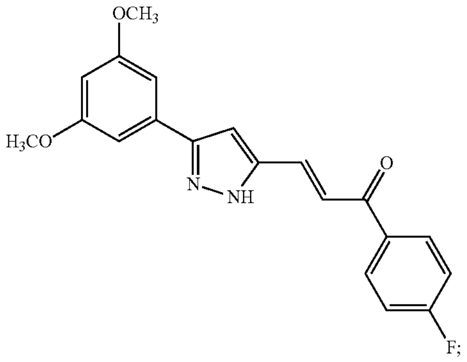
14e
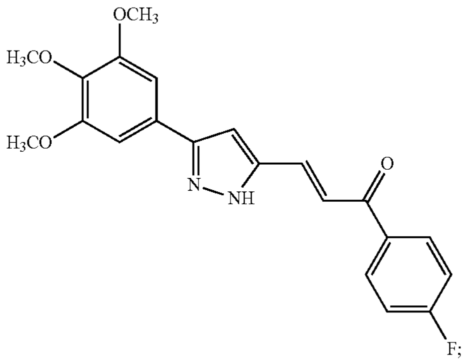
-continued
14f
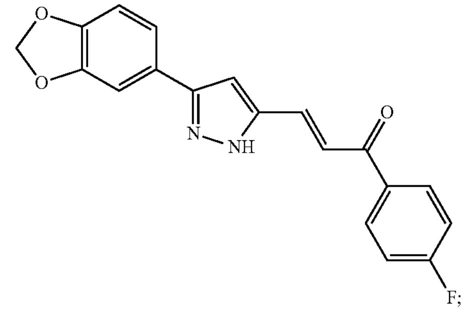
14g
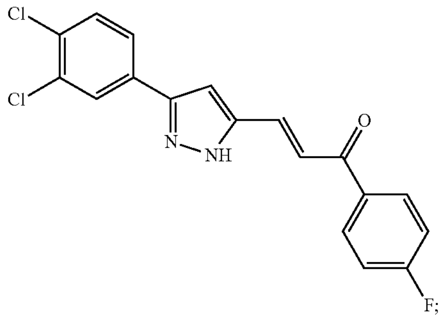
14h
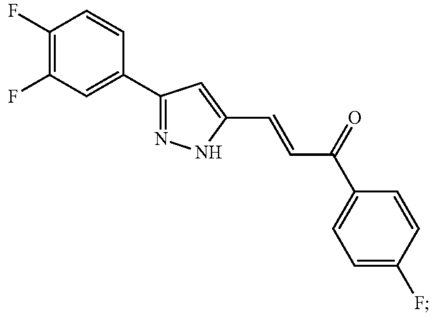
14i
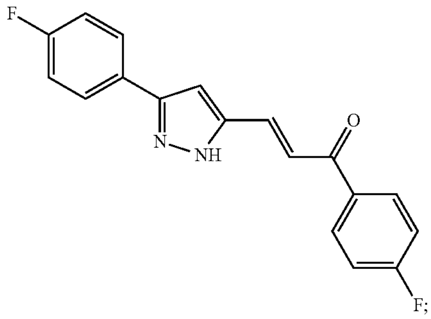
14j
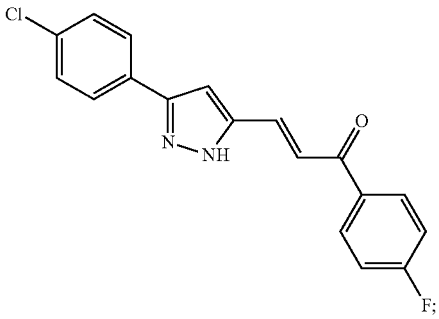

-continued
14k
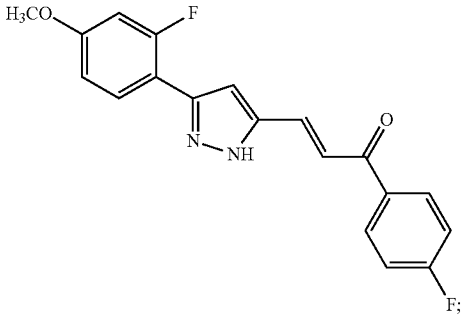
14l
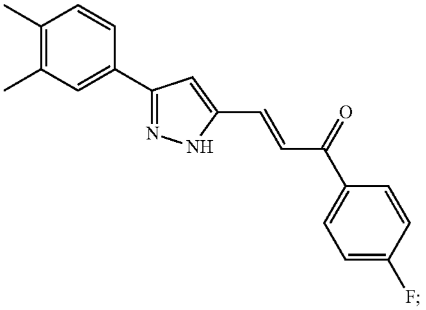
15a
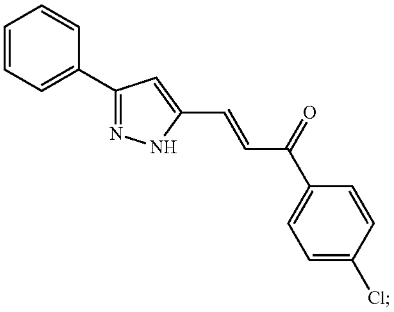
15b
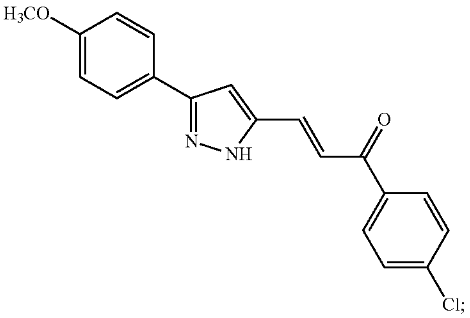
15c
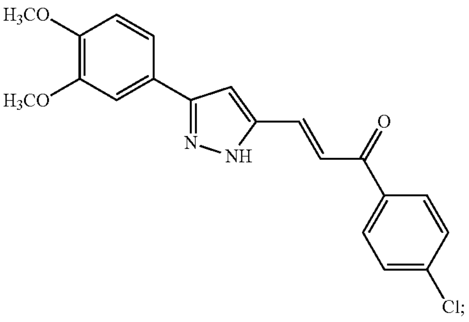
-continued
15d
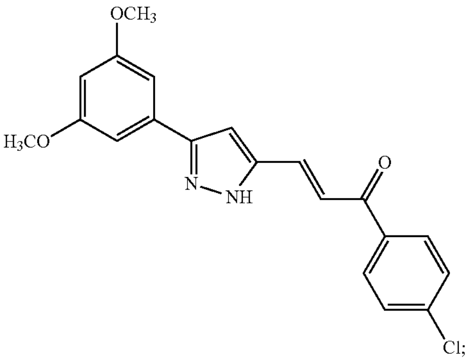
15e
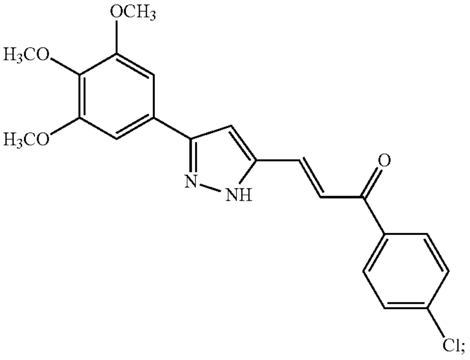
15f
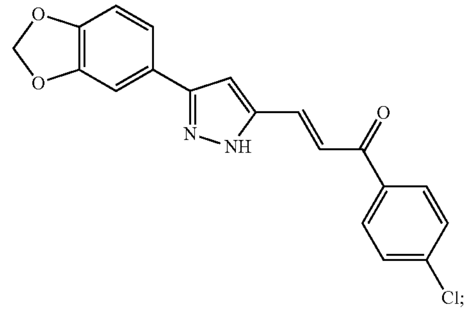
15g
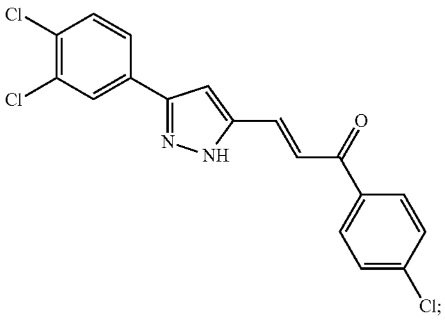

-continued
15h
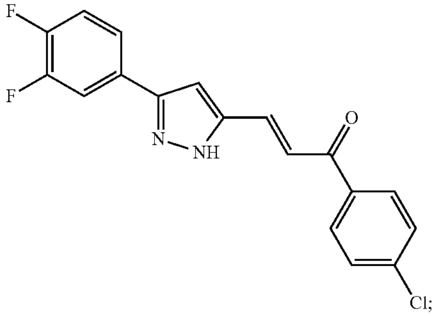
15i
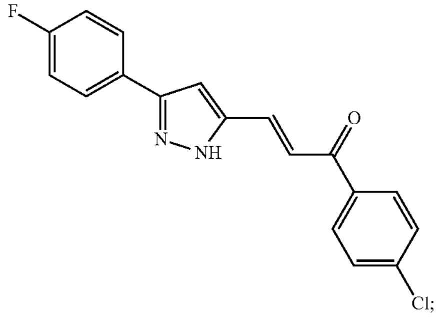
15j
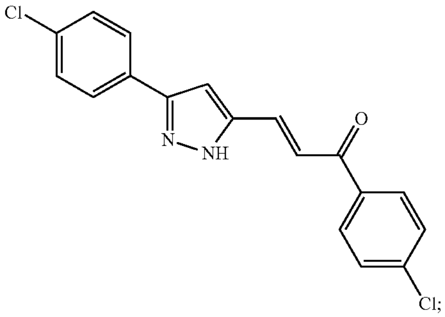
15k
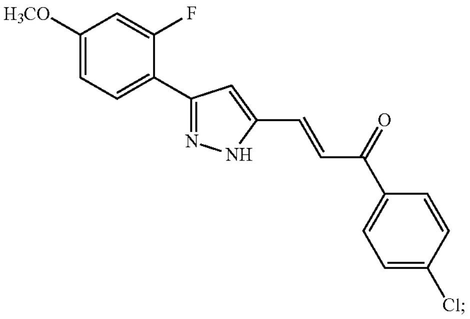
15l
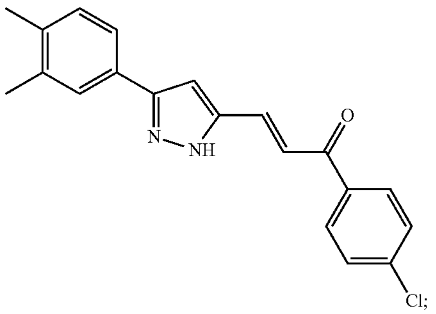
-continued
19a
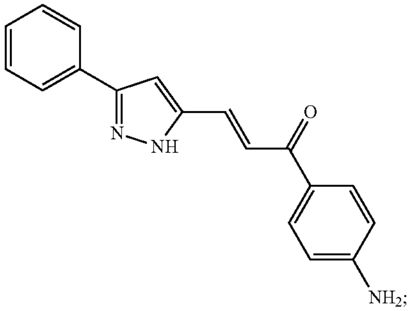
19b
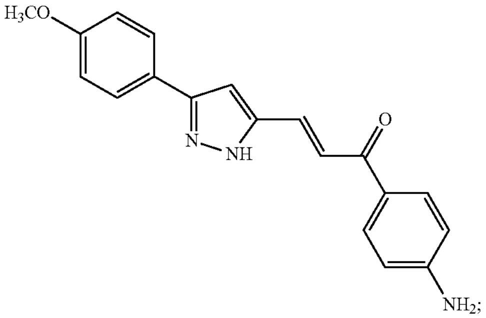
19c
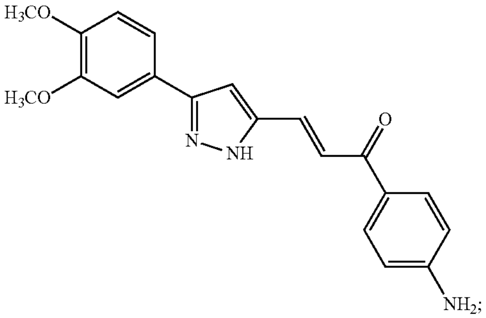
19d
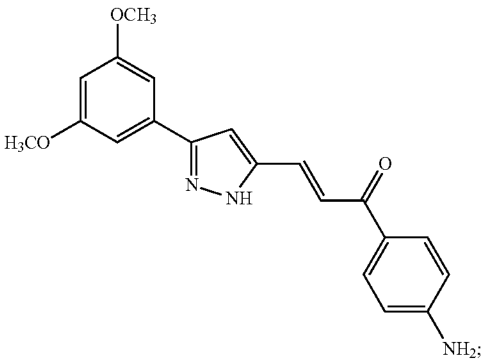

-continued
19e
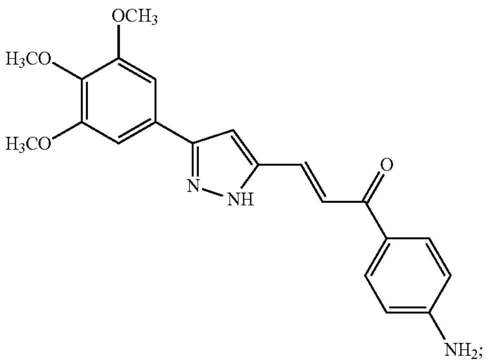
19f
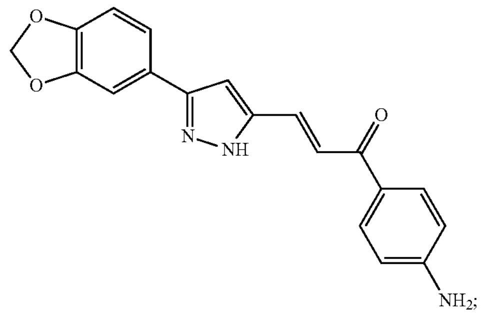
19g
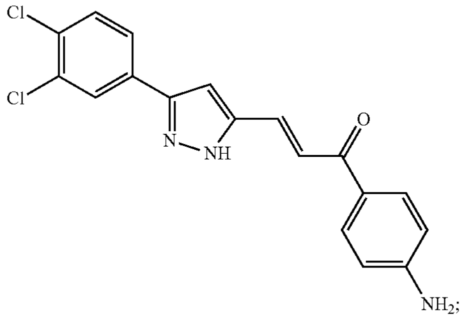
19h
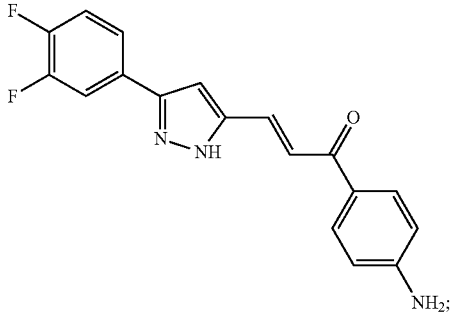
-continued
19i
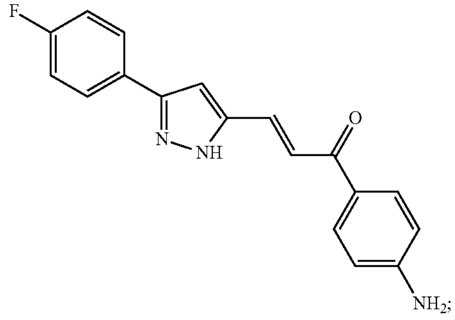
19j
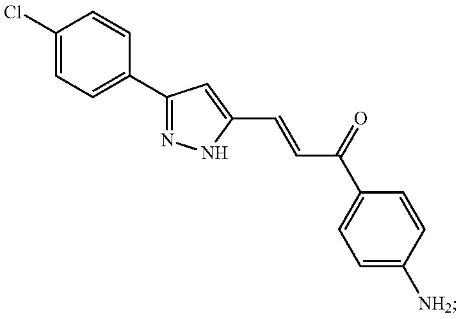
19k
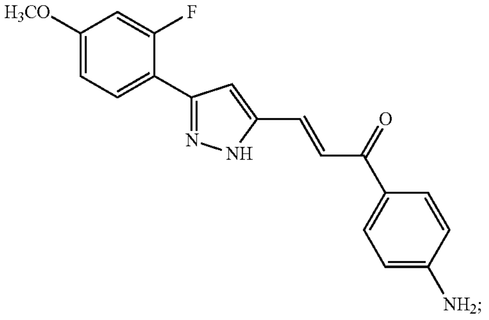
19l
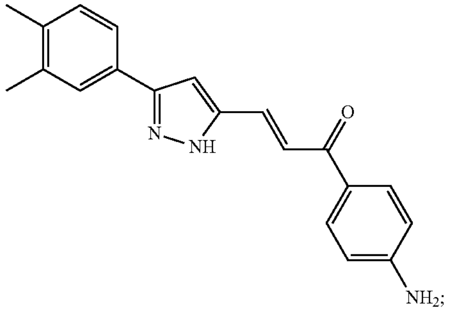
20a
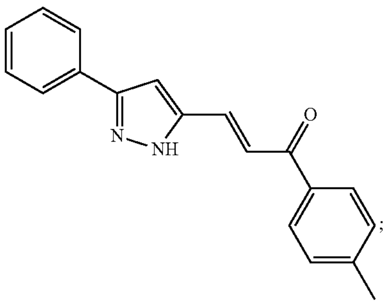

-continued
20b
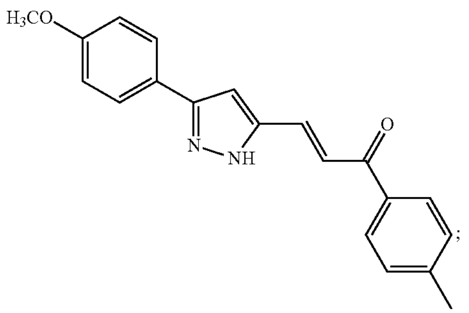
20c
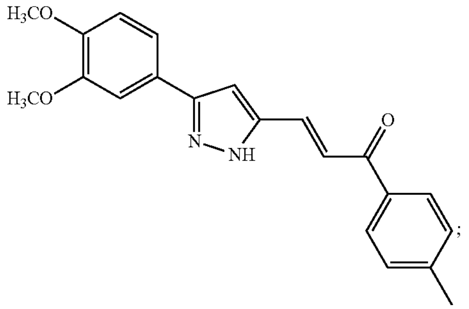
20d
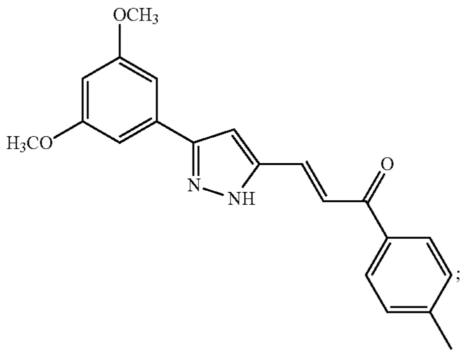
20e
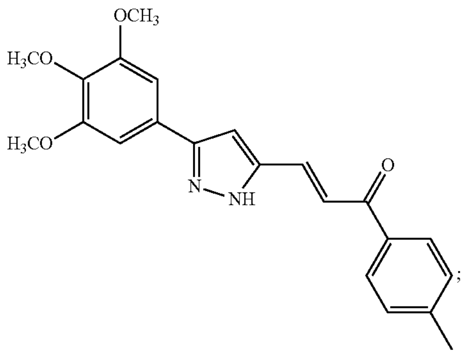
-continued
20f
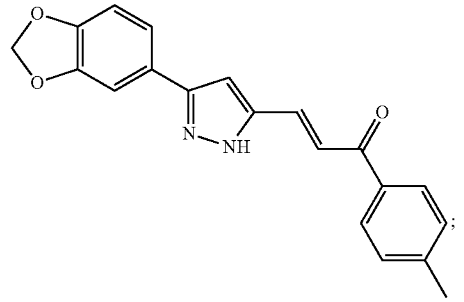
20g
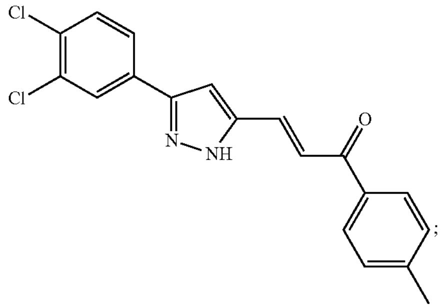
20h
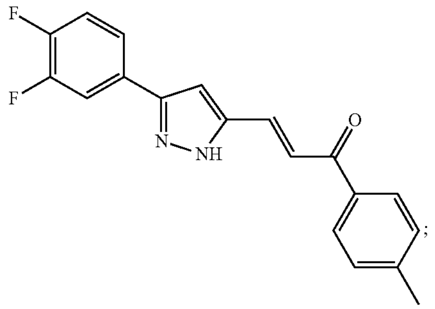
20i
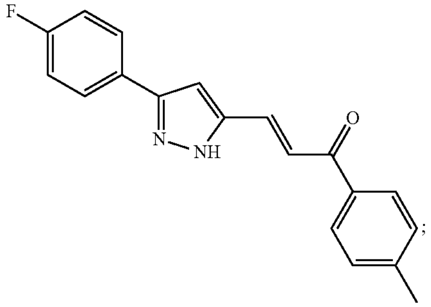
20j
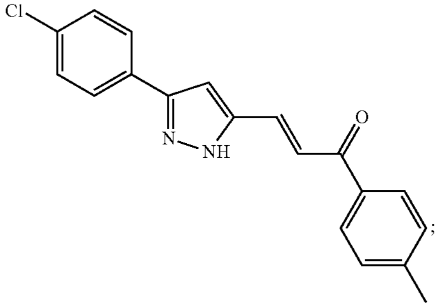

-continued
20k
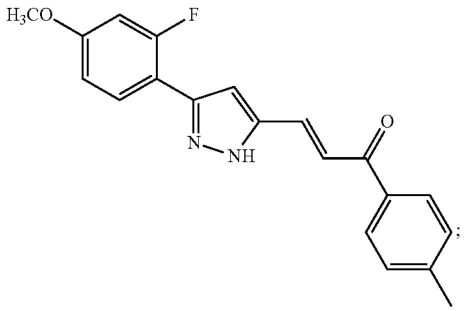
20l
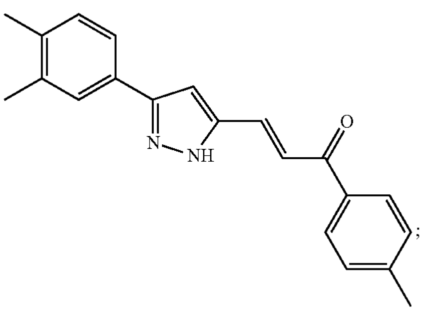
22a
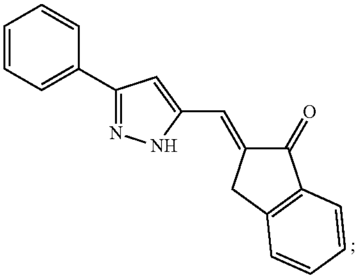
22b
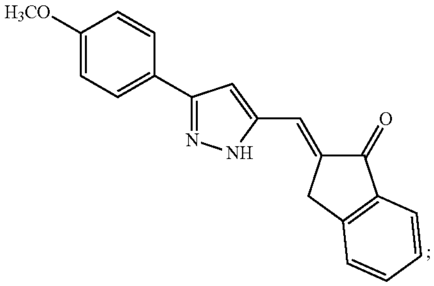
22c
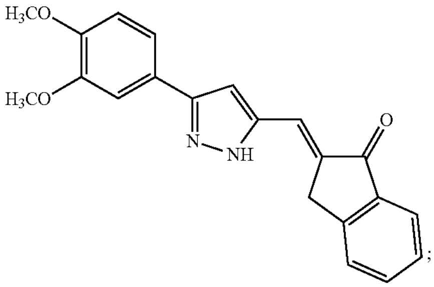
-continued
22d
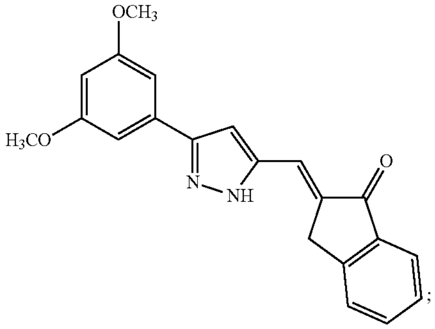
22e
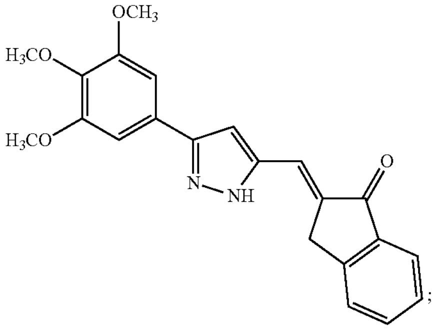
22f
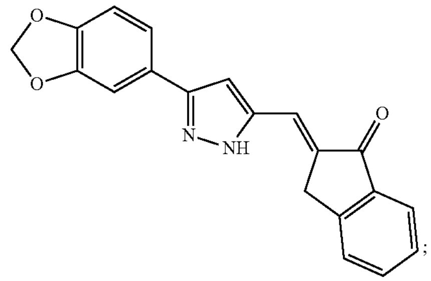
22g
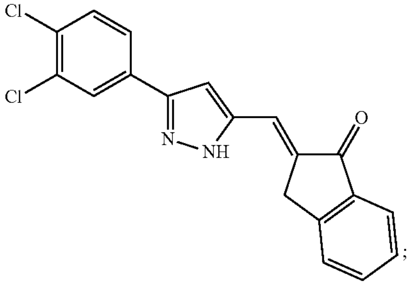
22h
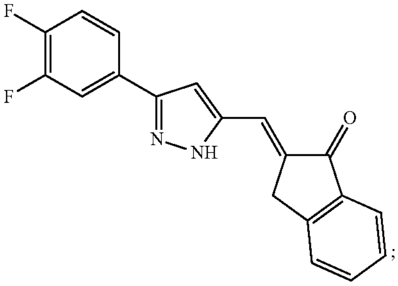

-continued
22i
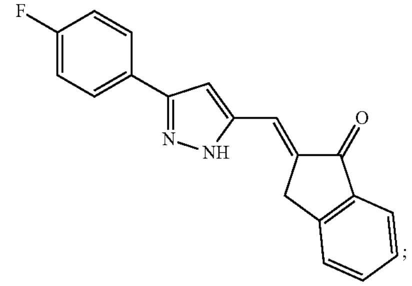
22j
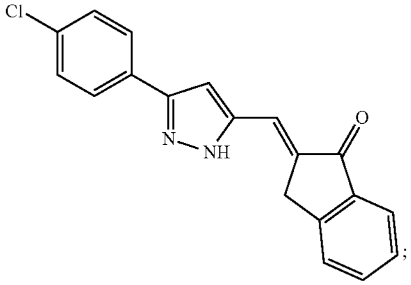
22k
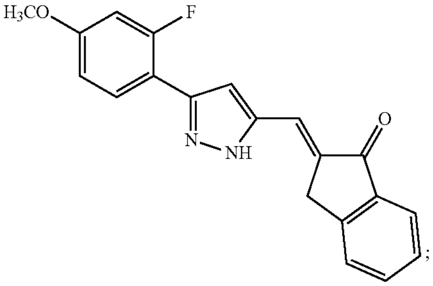
22l
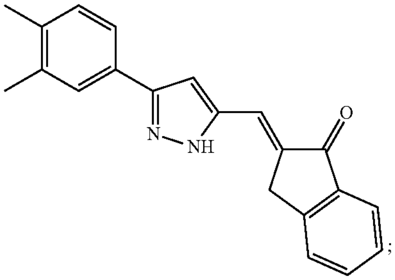
23a
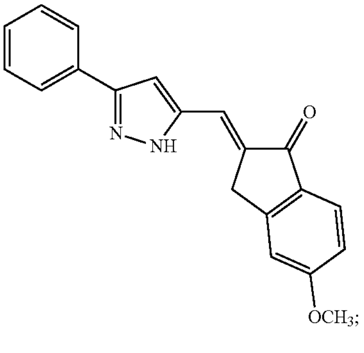
-continued
23b
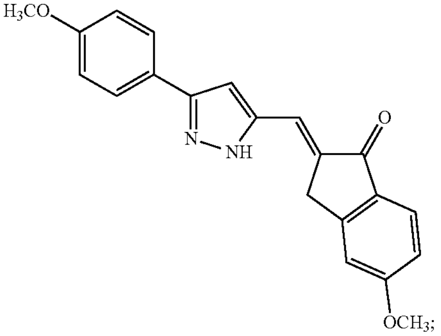
23c
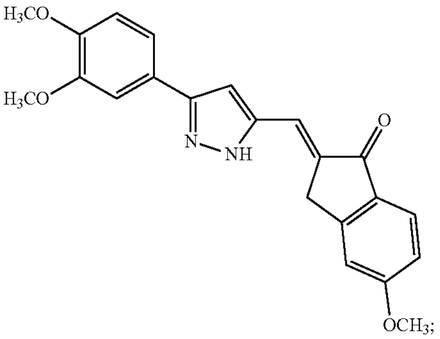
23d
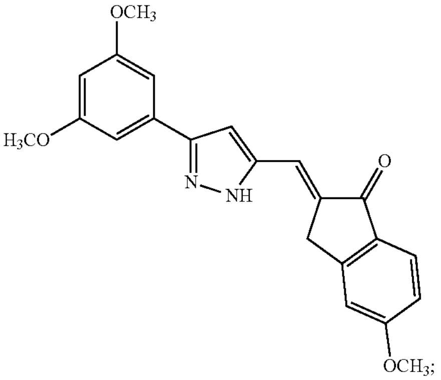
23e
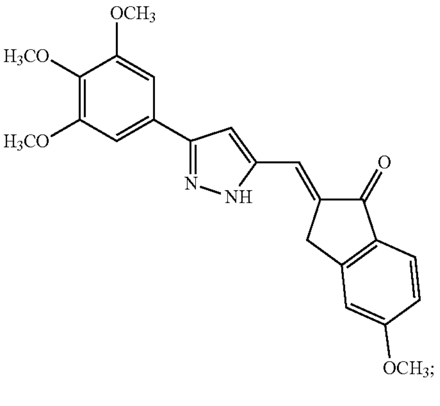

-continued
23f
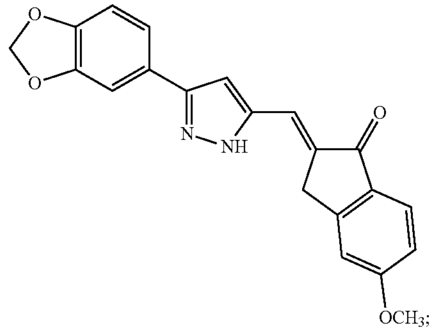
23g
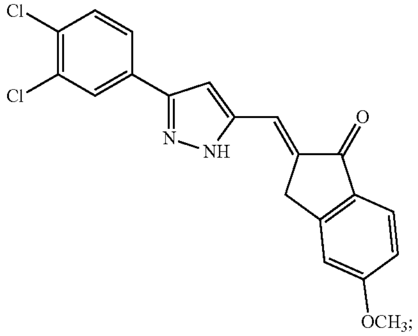
23h
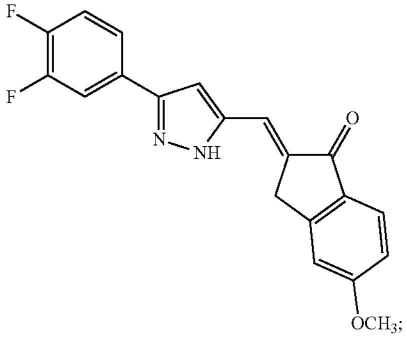
23i
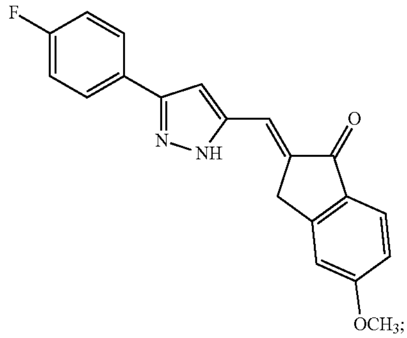
-continued
23j
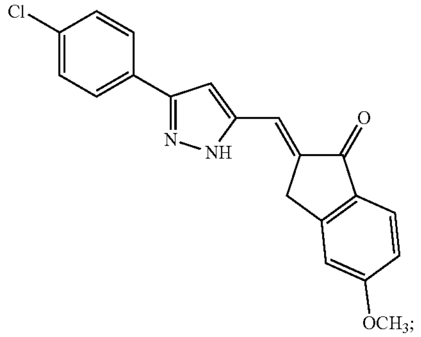
23k
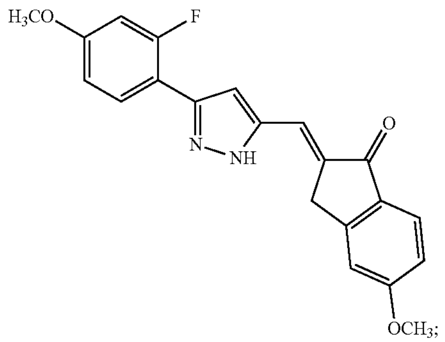
and
23l
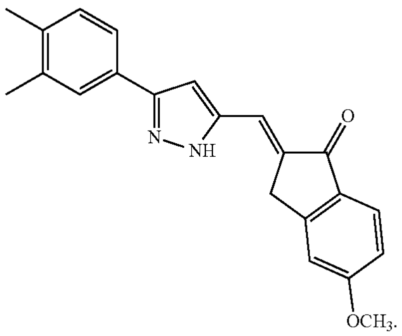
2. A pyrazolochalcone selected from the group consisting of:
8a
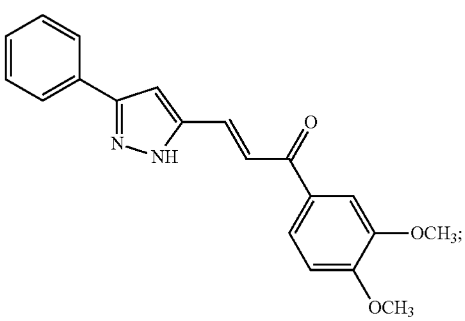

-continued
8b
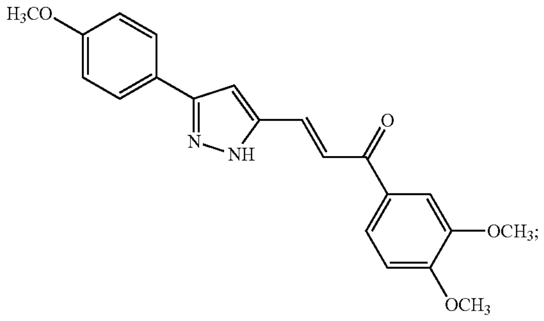
8c
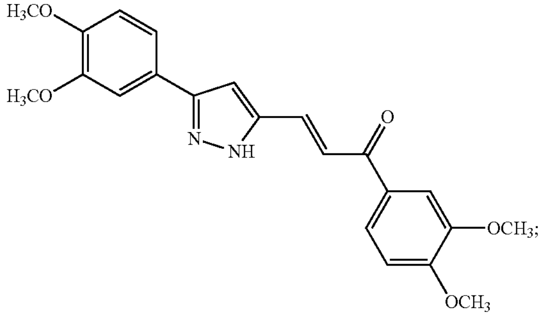
8d
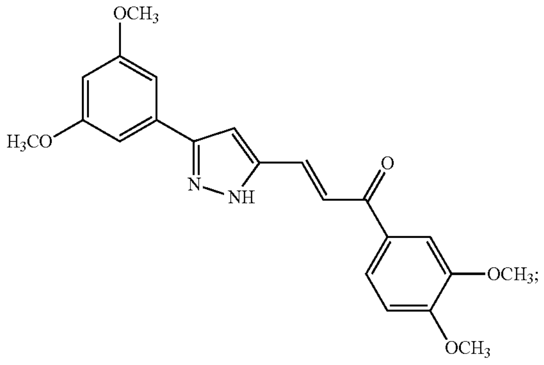
8e
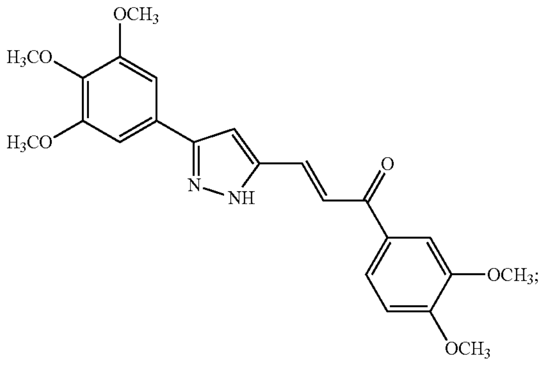
-continued
8f
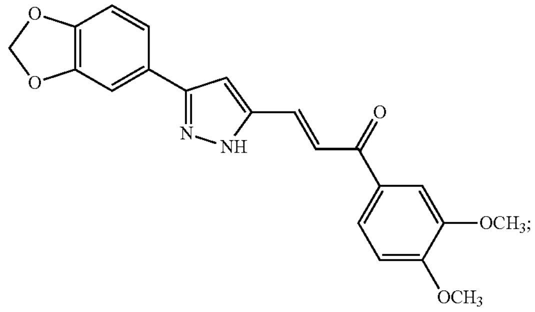
8g
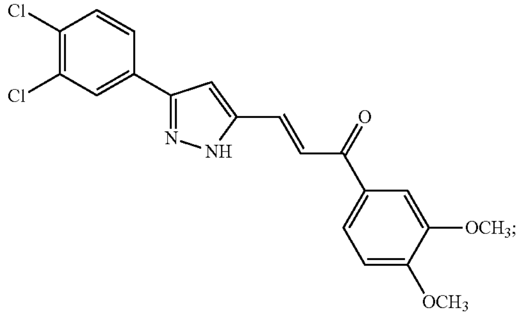
8h
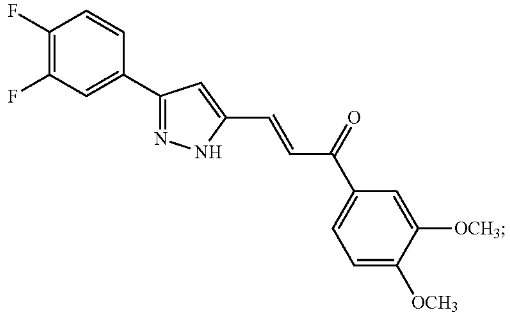
8i
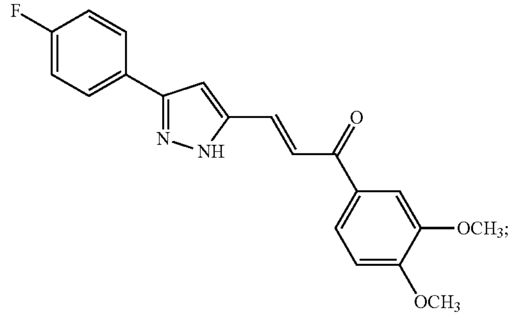
8j
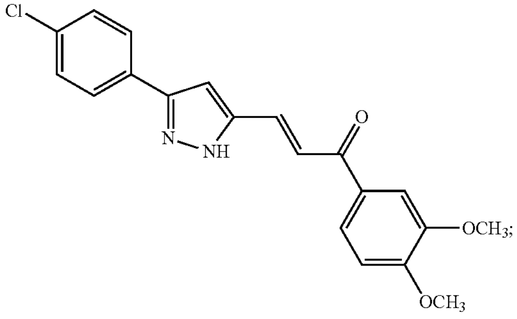

-continued
8k
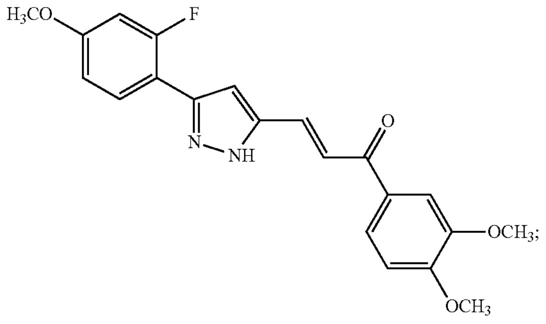
8l
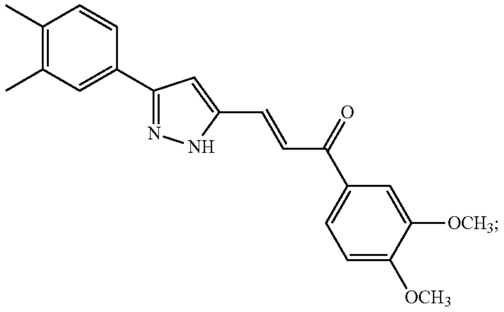
9a
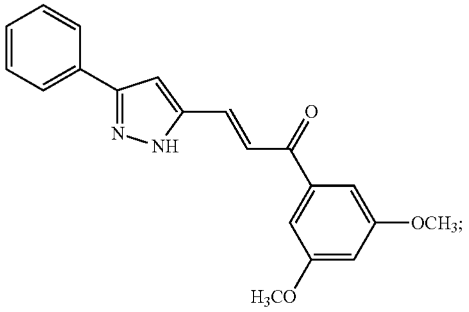
9b
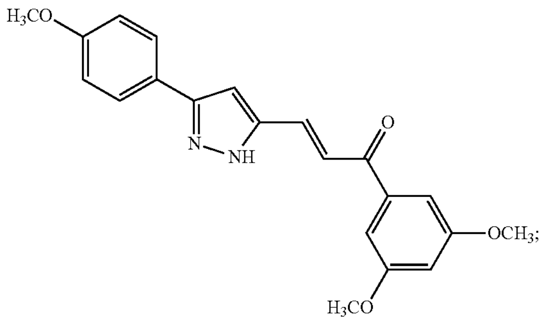
-continued
9c
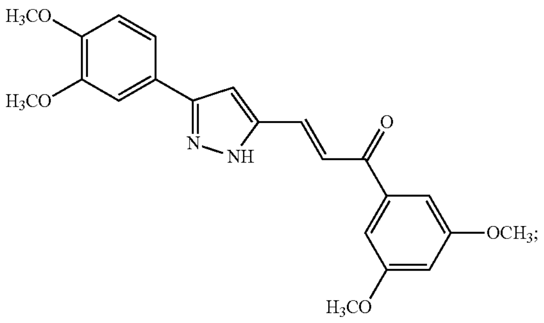
9d
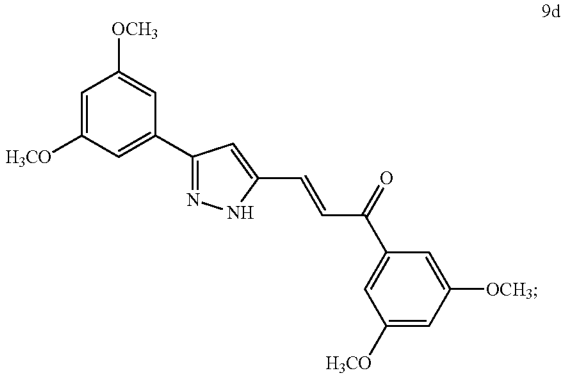
9e
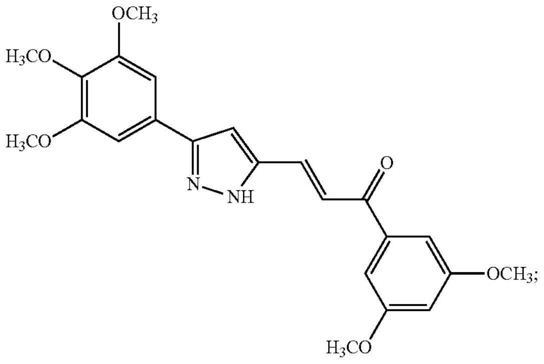
9f
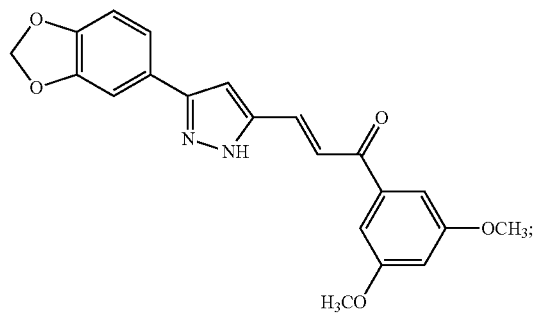

-continued
9g
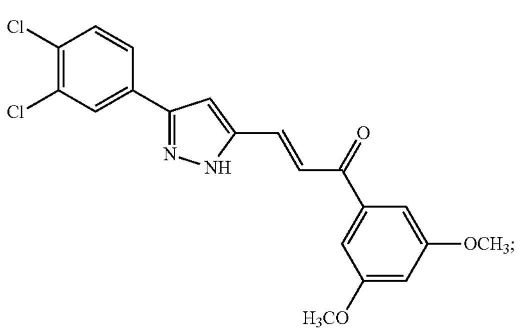
9h
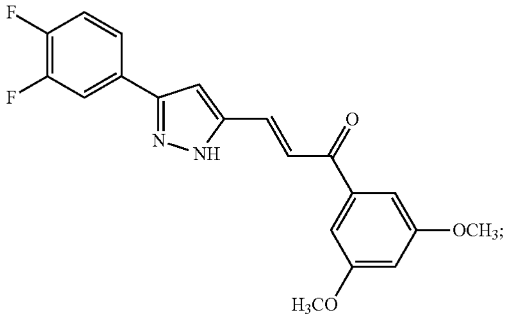
9i
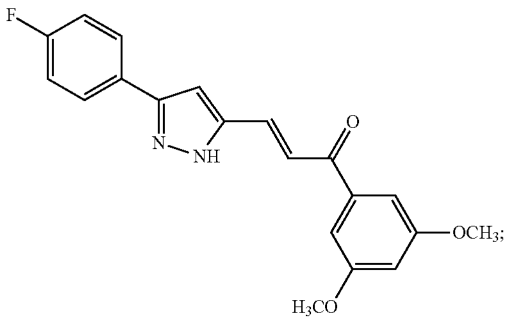
9j
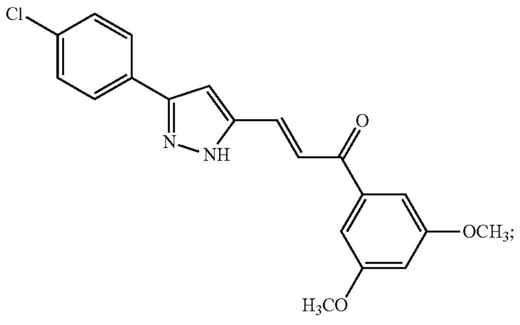
-continued
9k
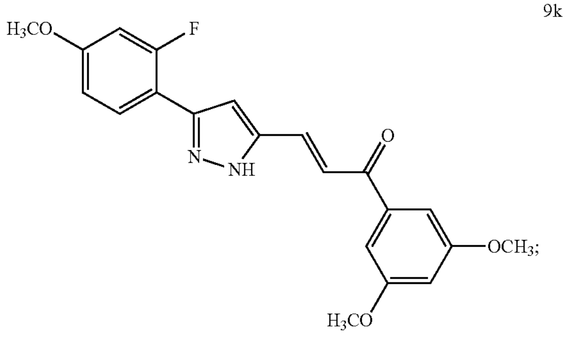
9l
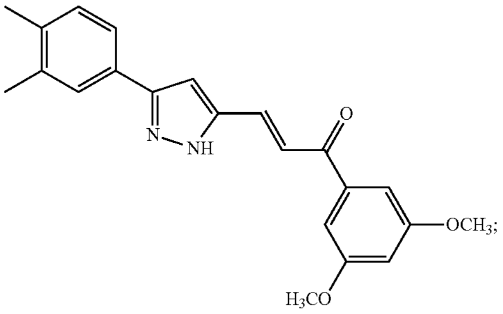
10a
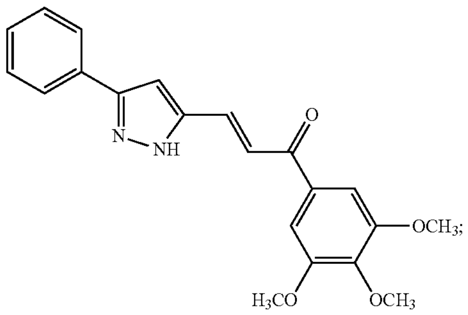
10b
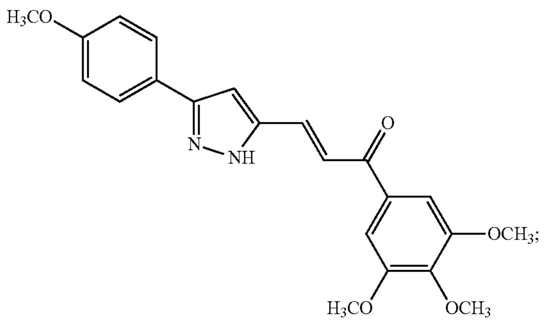

-continued
10c
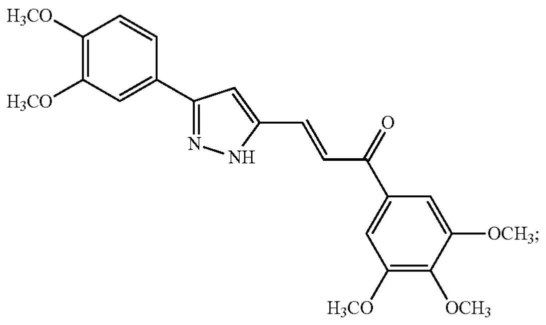
10d
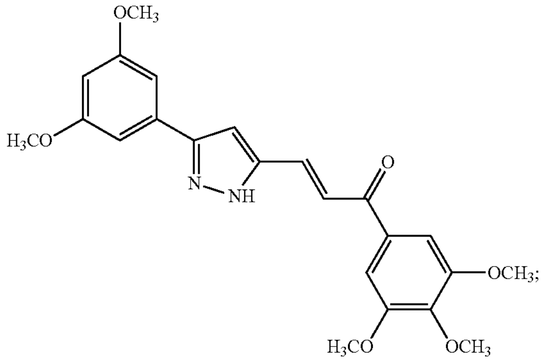
10e
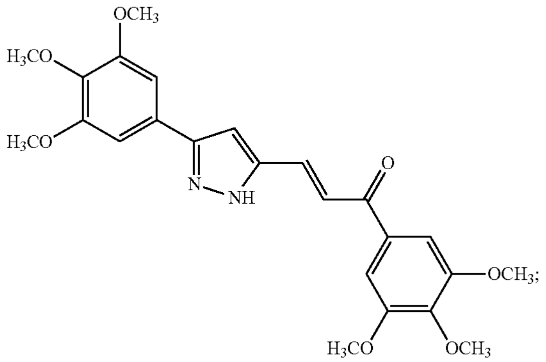
10f
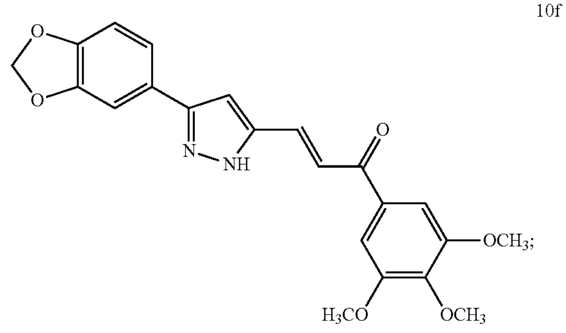
-continued
10g
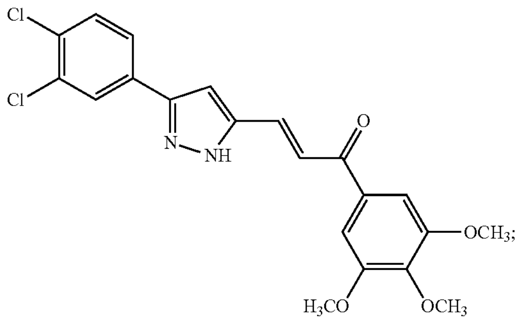
10h
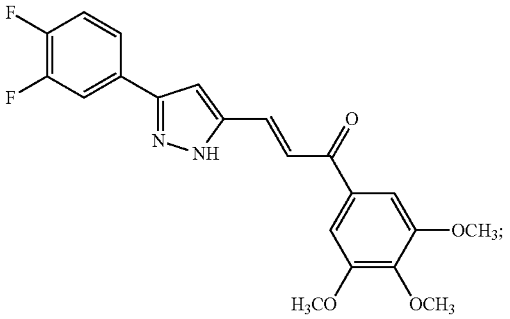
10i
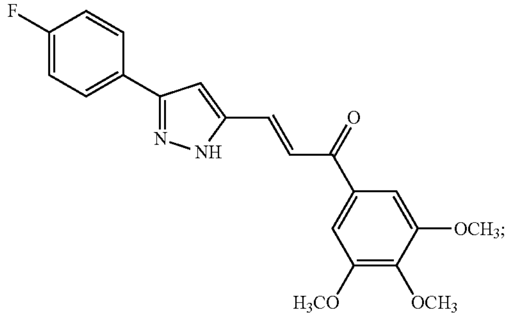
10j
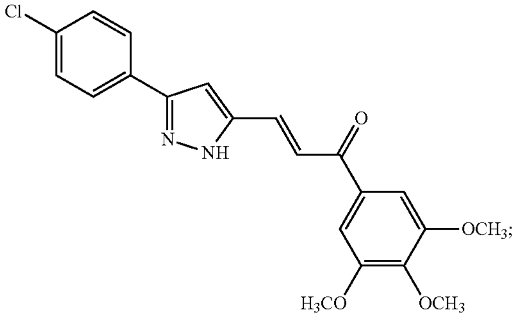

-continued
10k
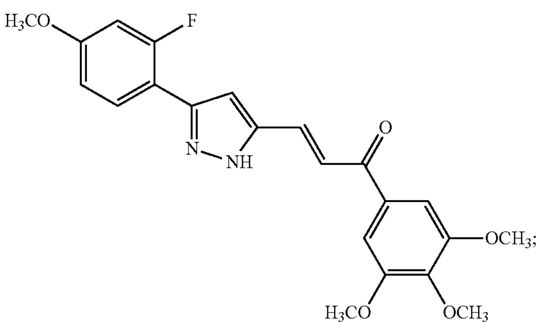
10l
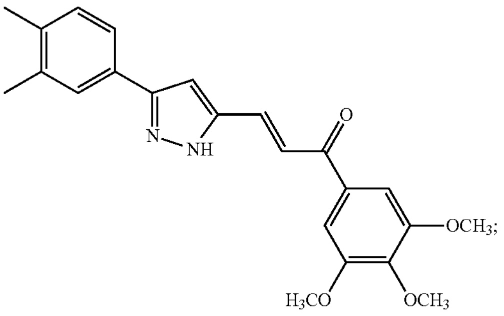
11a
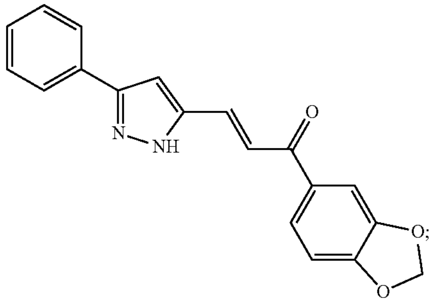
11b
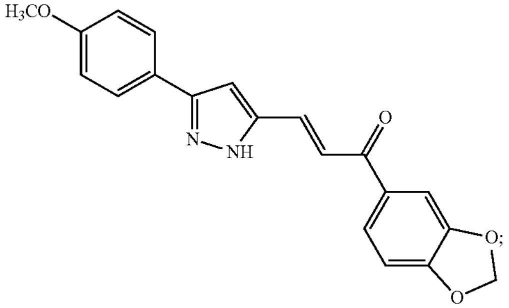
11c
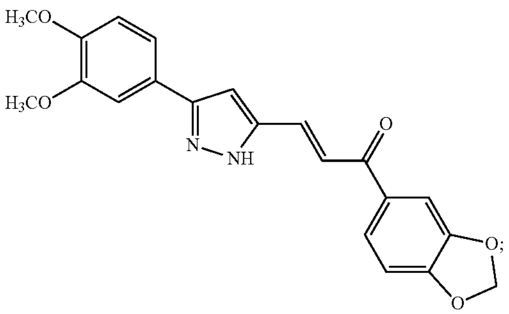
-continued
11d
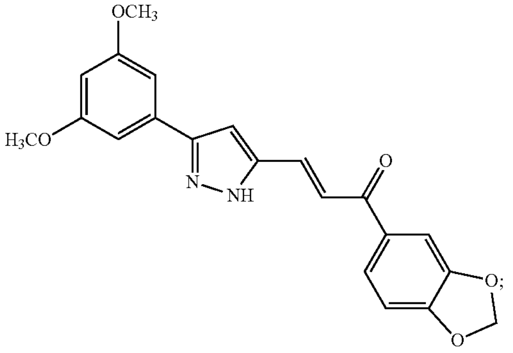
11e
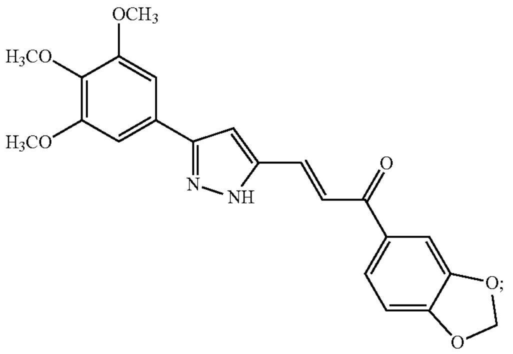
11f
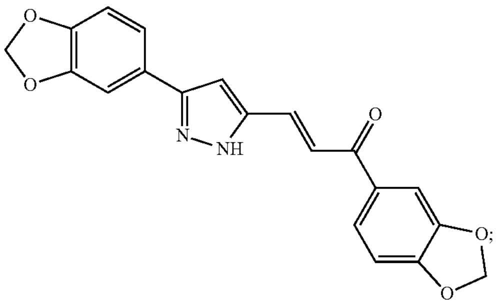
11g
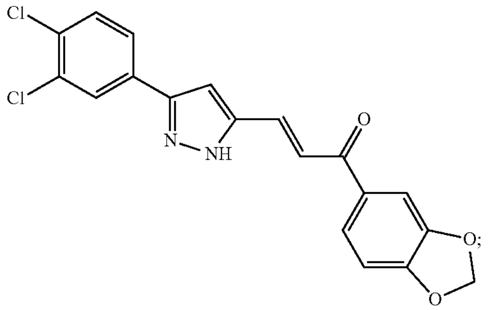

-continued
11h
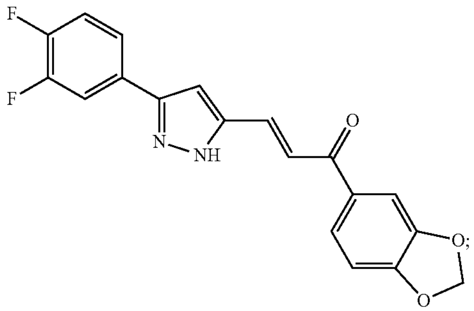
11i
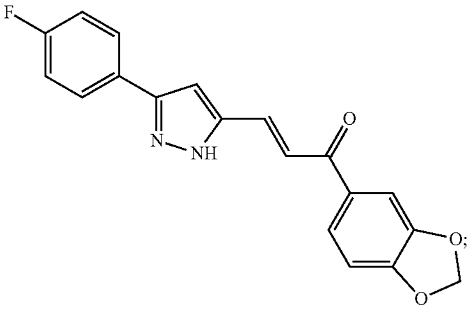
11j
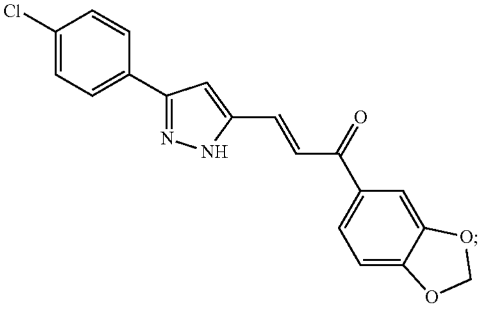
11k
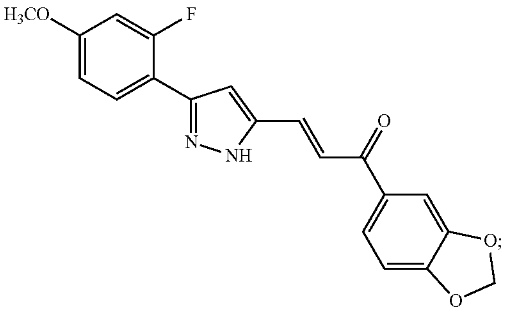
11l
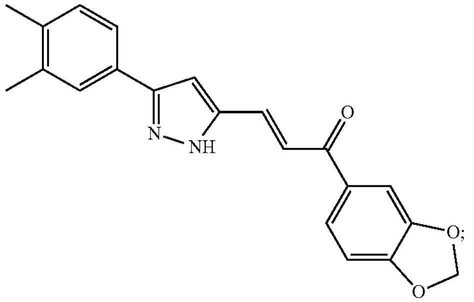
-continued
12a
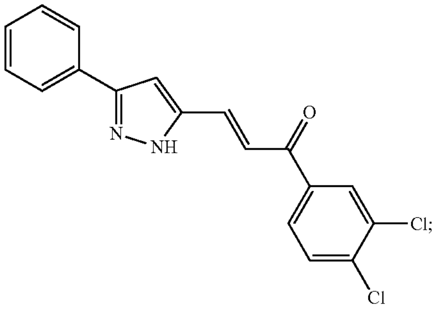
12b
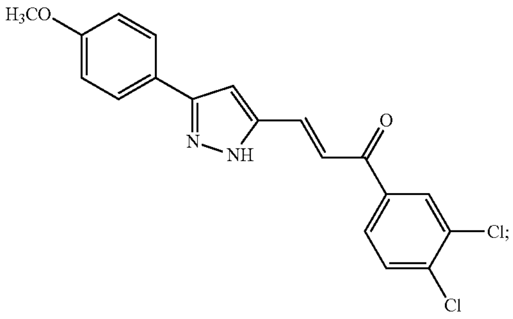
12c
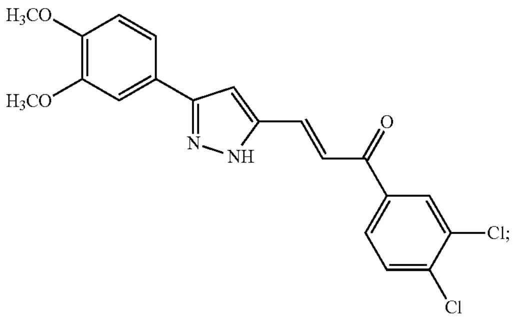
12d
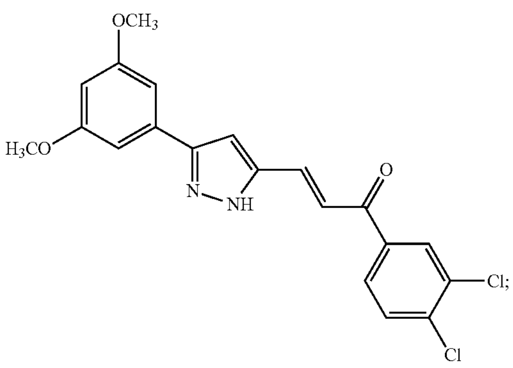

-continued
12e
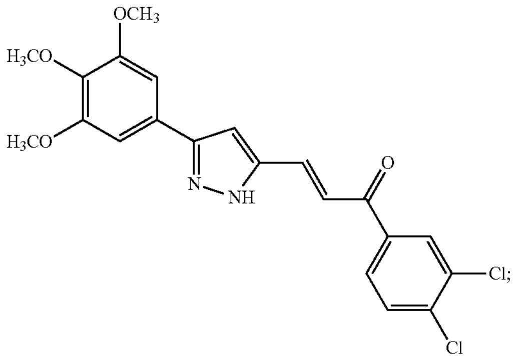
12f
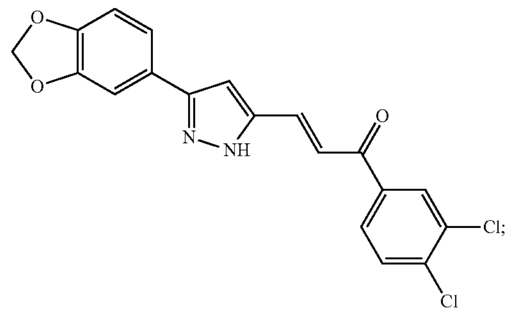
12g
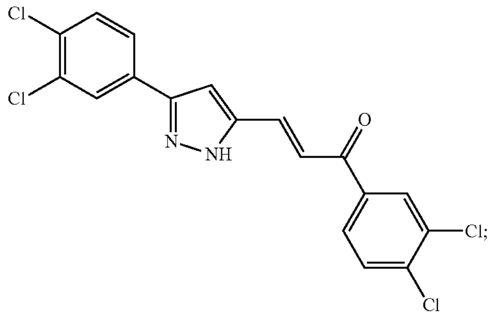
12h
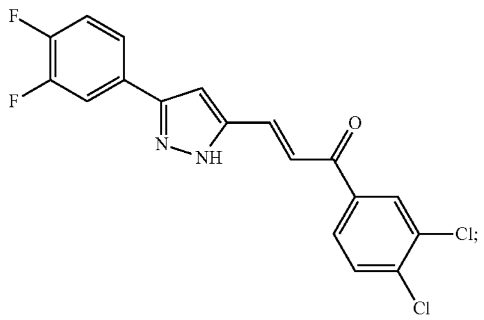
-continued
12i
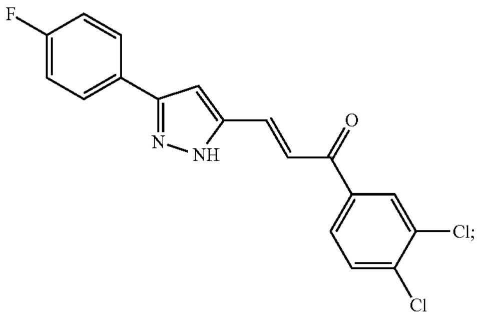
12j
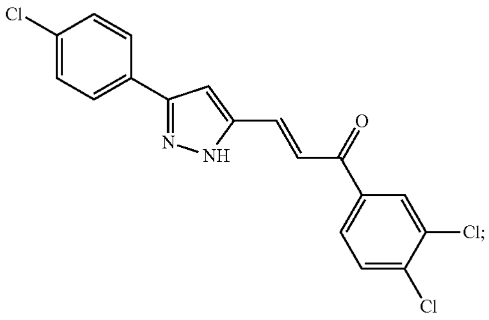
12k
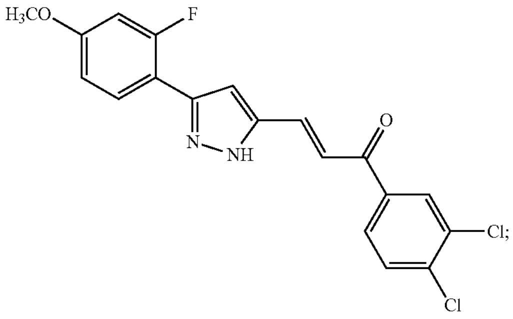
12l
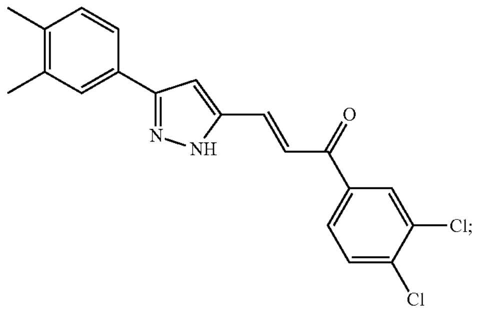
13a
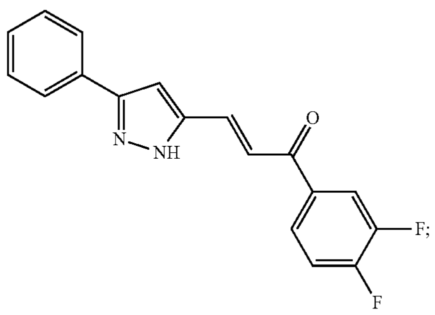

-continued
13b
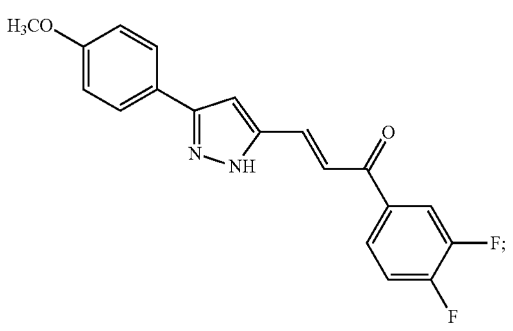
13c
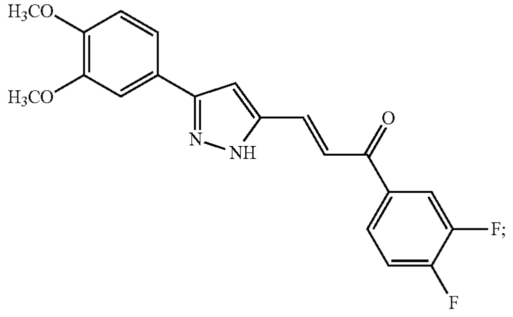
13d
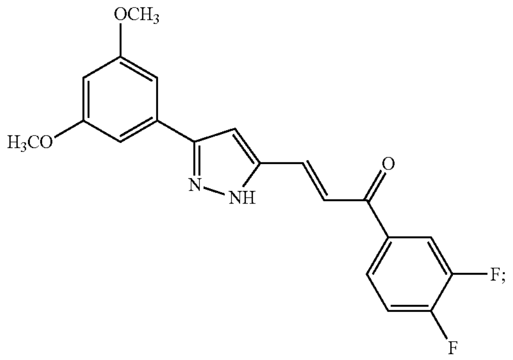
13e
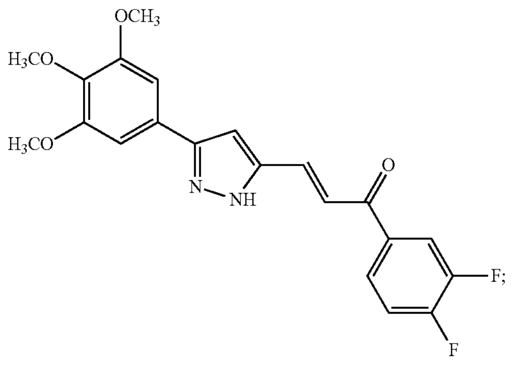
-continued
13f
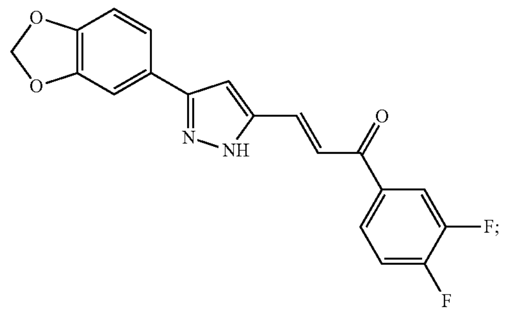
13g
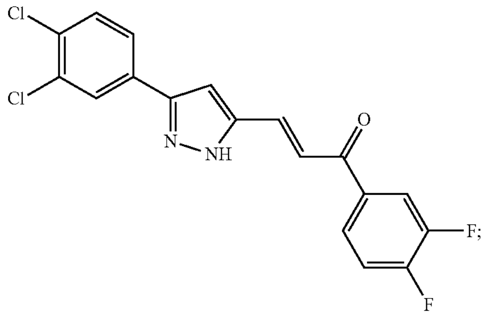
13h
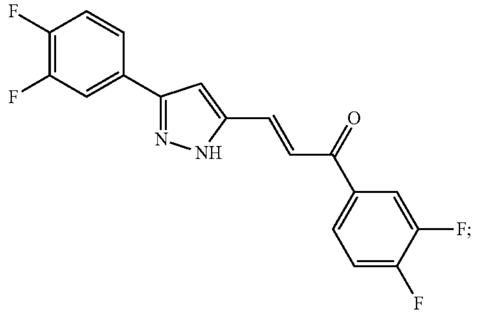
13i
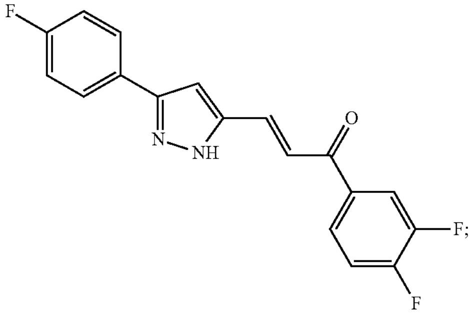
13j
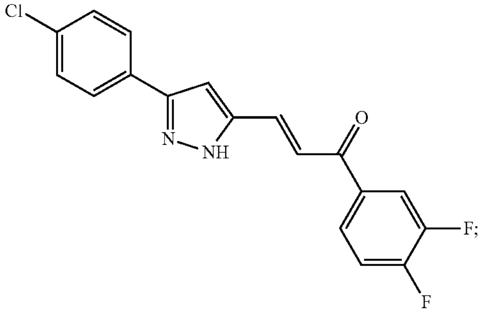

-continued
13k
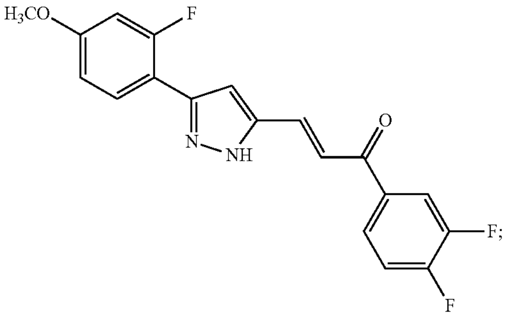
13l
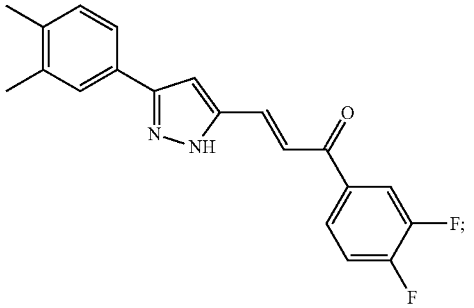
16a
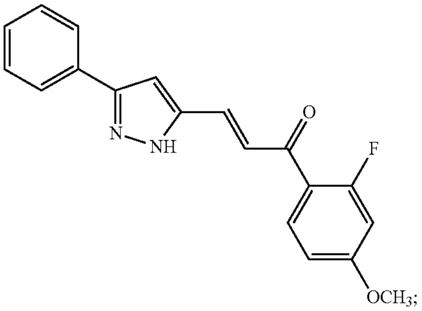
16b
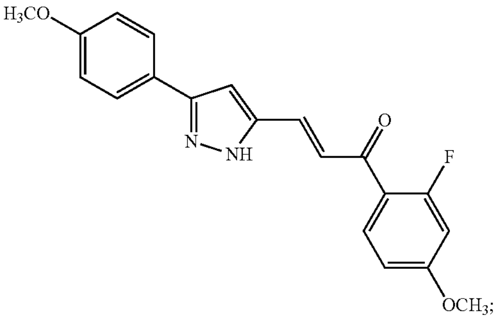
16c
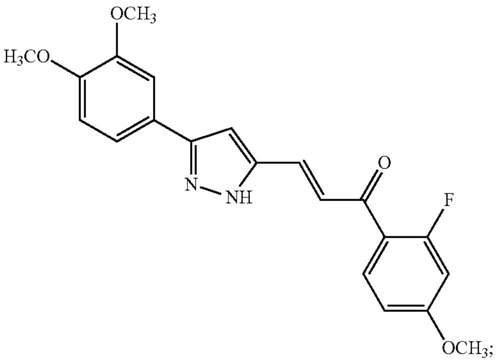
-continued
16d
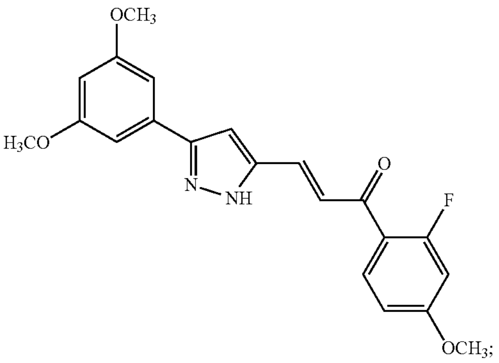
16e
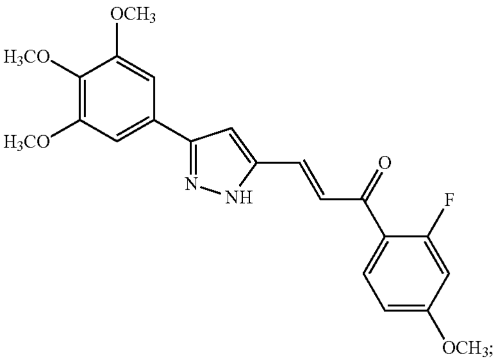
16f
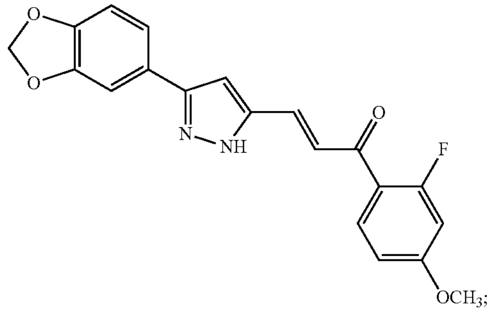
16g
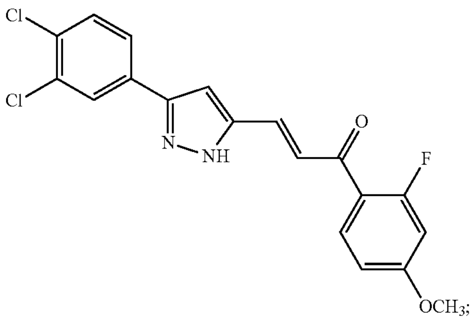

-continued
16h
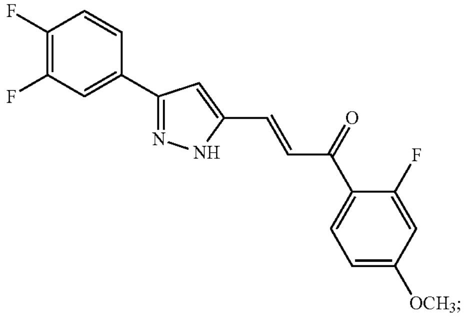
16i
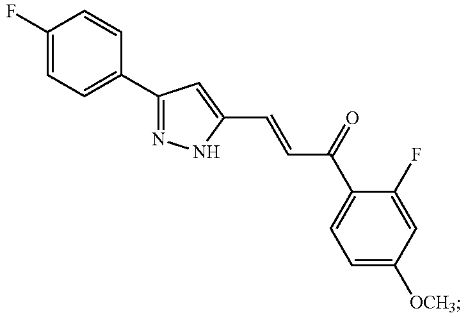
16j
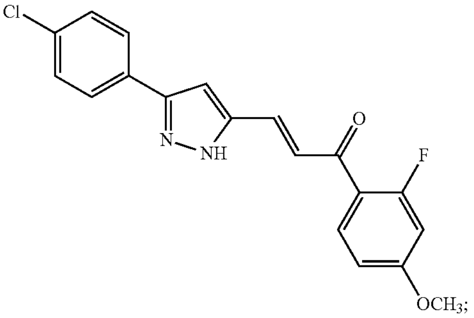
16k
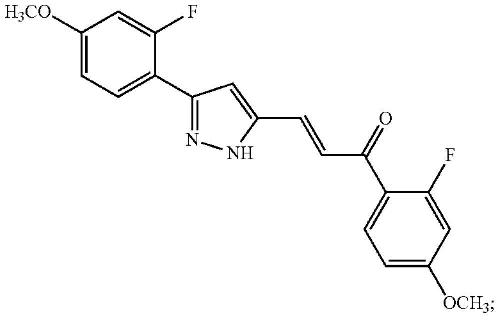
16l
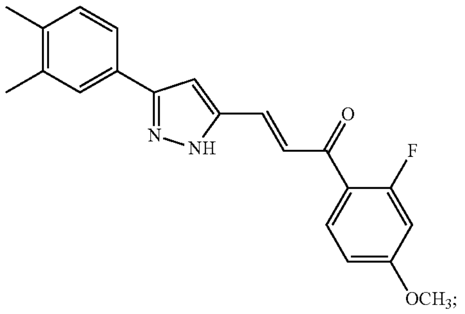
-continued
17a
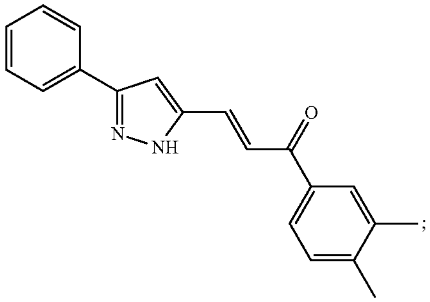
17b
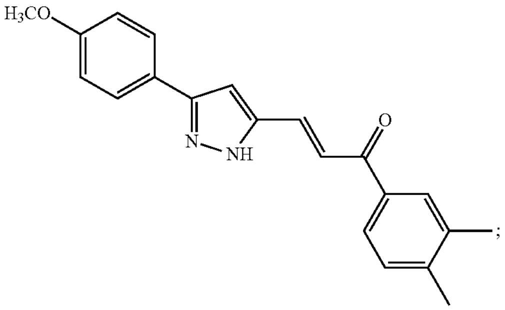
17c
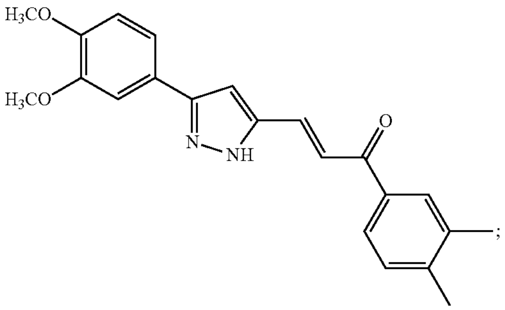
17d
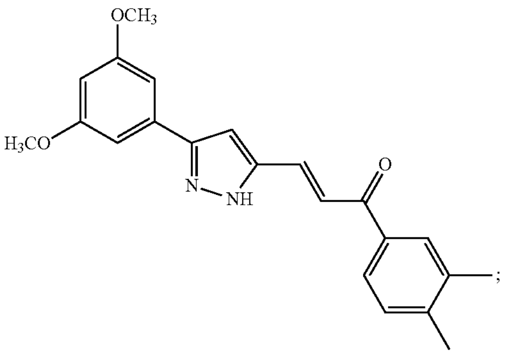

-continued
17e
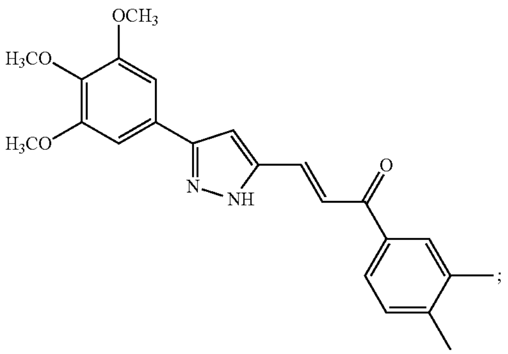
17f
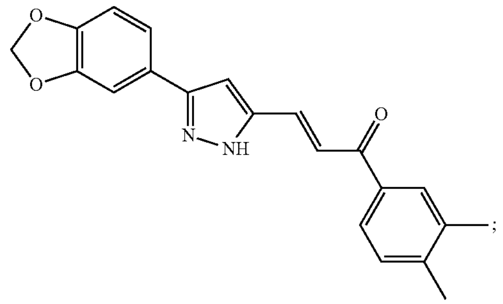
17g
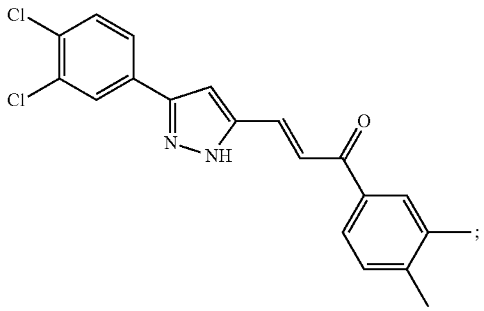
17h
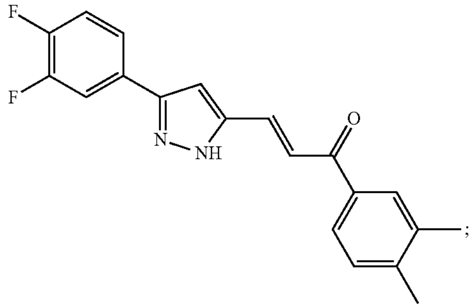
-continued
17i
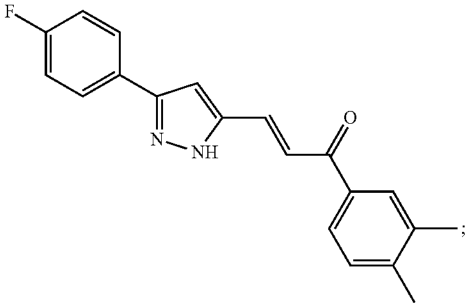
17j
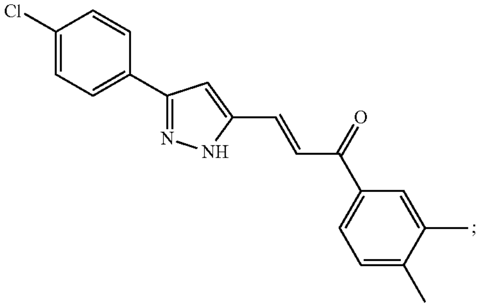
17k
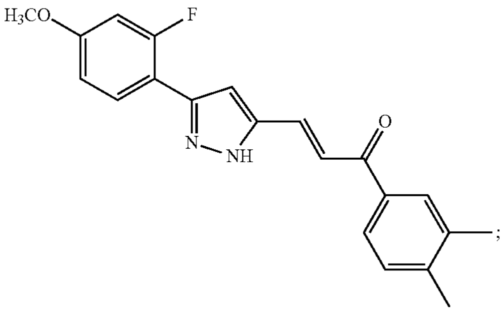
17l
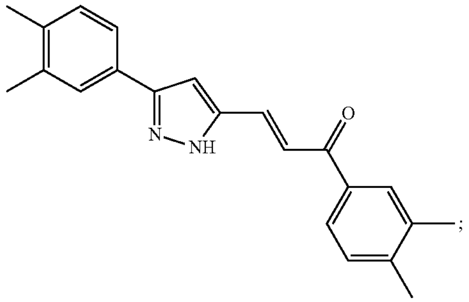
18a
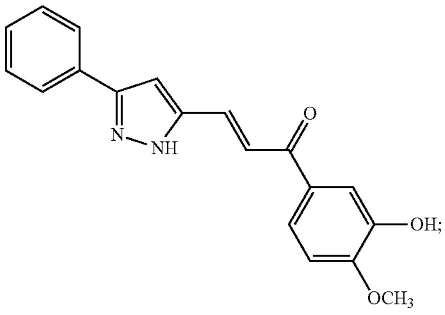

-continued
18b
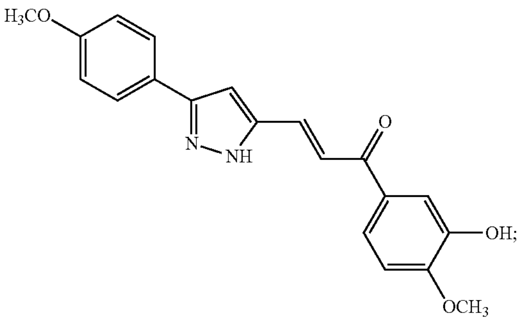
18c
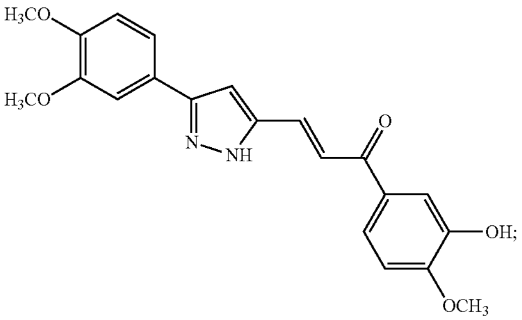
18d
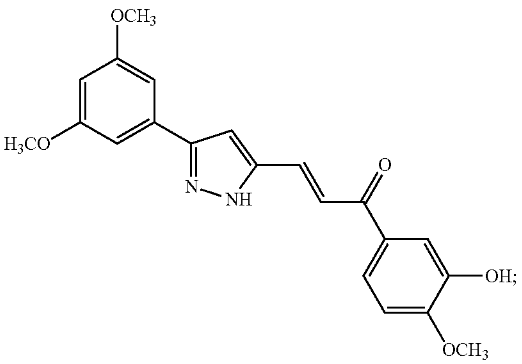
18e
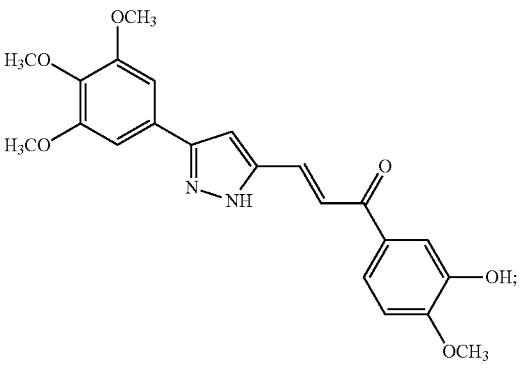
-continued
18f
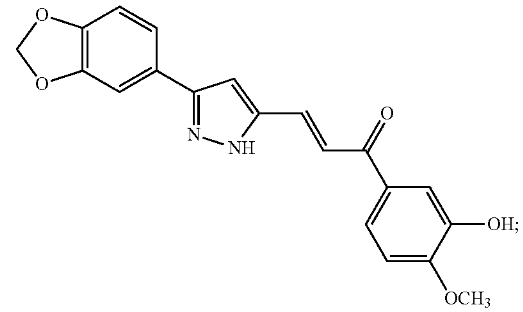
18g
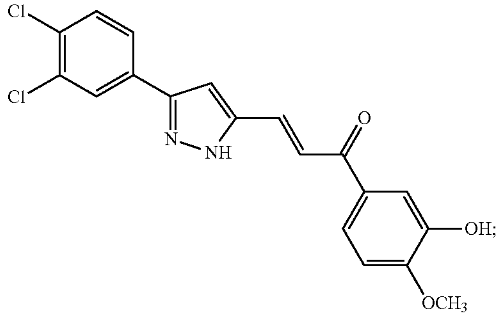
18h
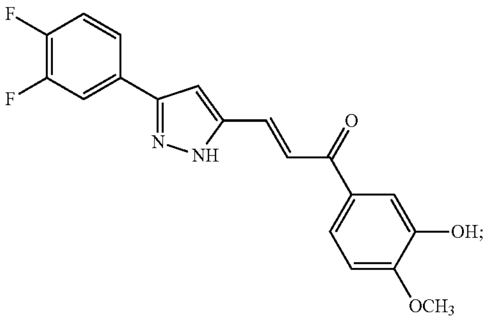
18i
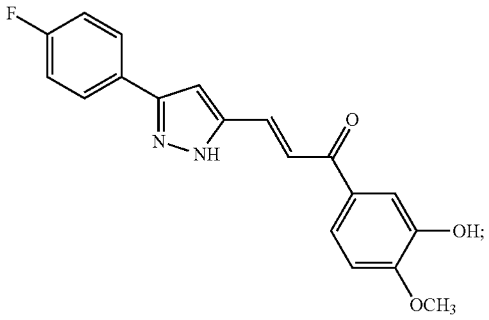

-continued
18j
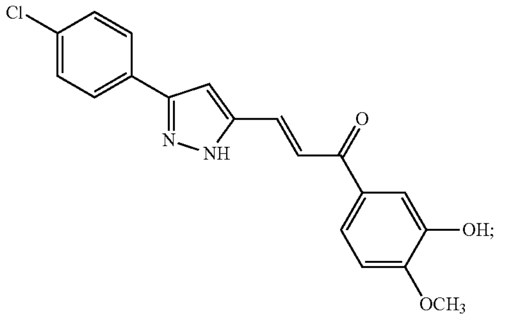
18k
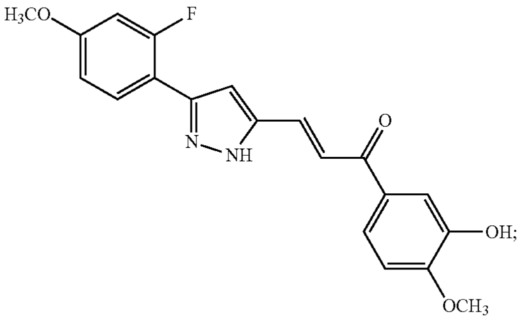
18l
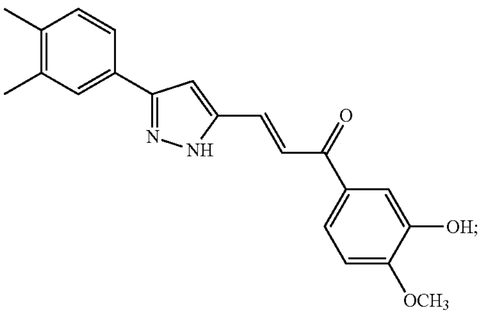
21a
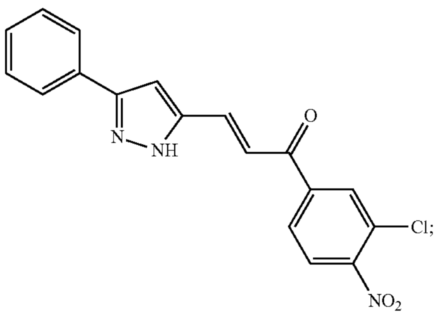
-continued
21b
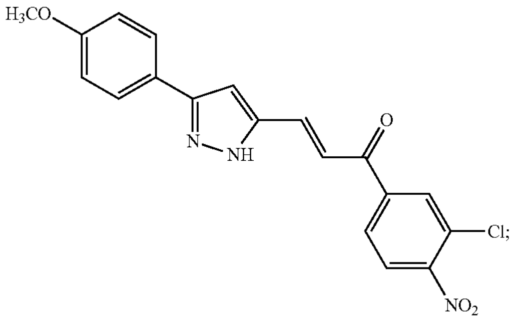
21c
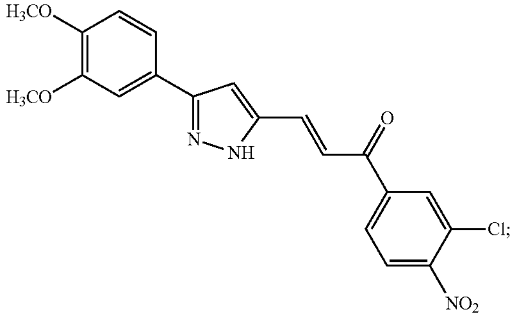
21d
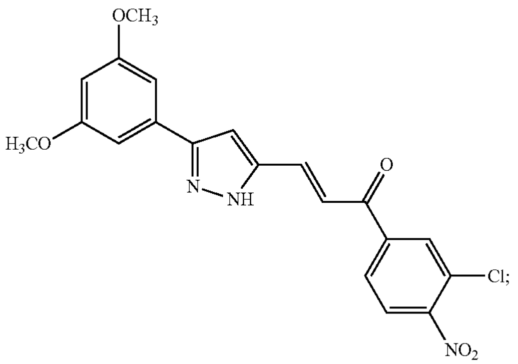
21e
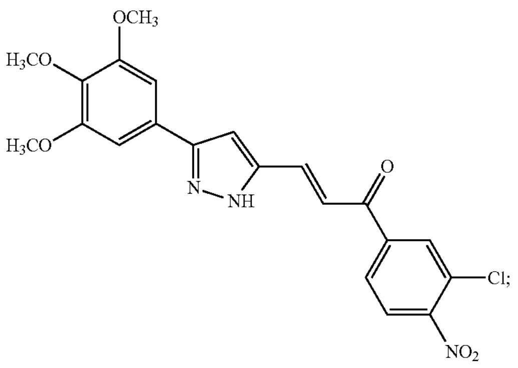

-continued
21f
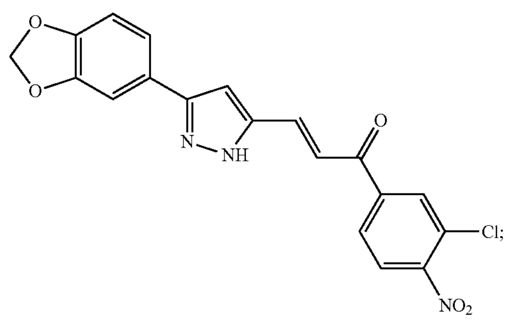
21g
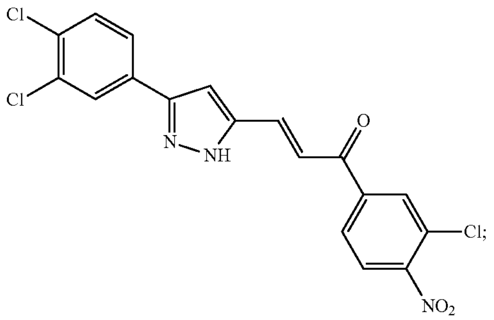
21h
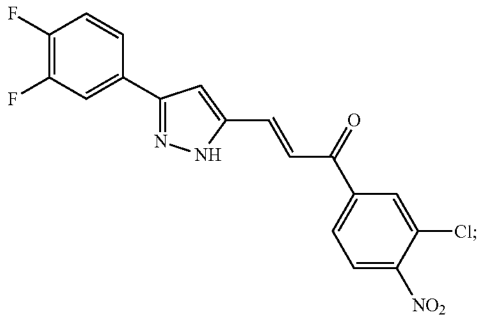
21i
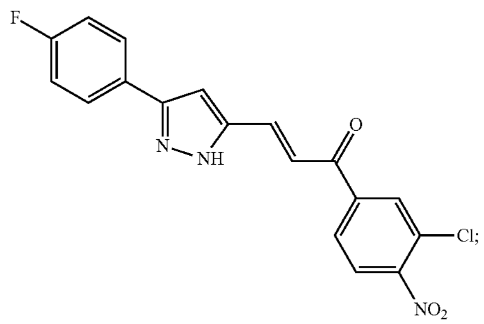
-continued
21j
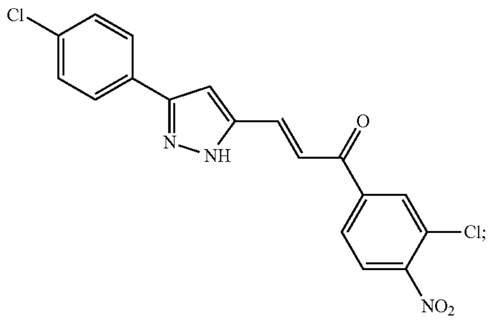
21k
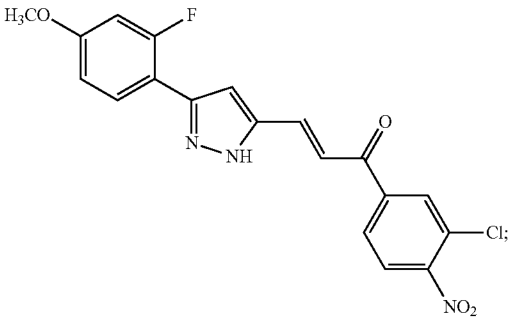
21l
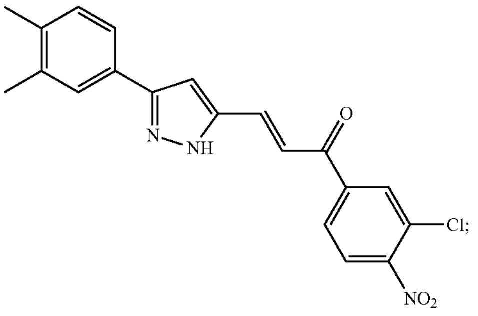
24a
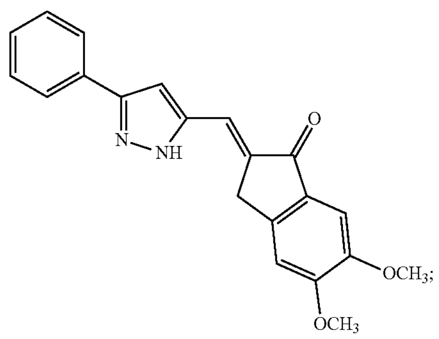

-continued
24b
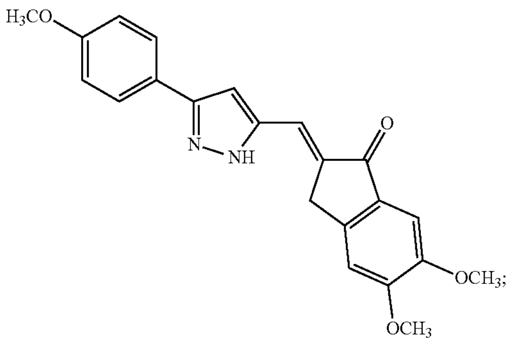
24c
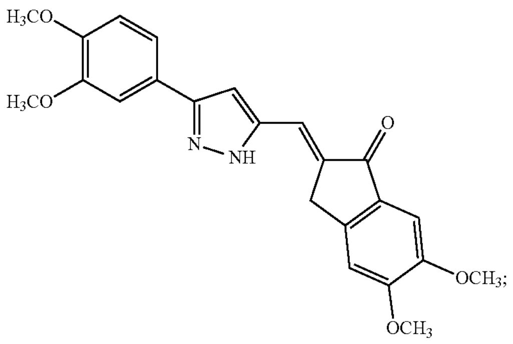
24d
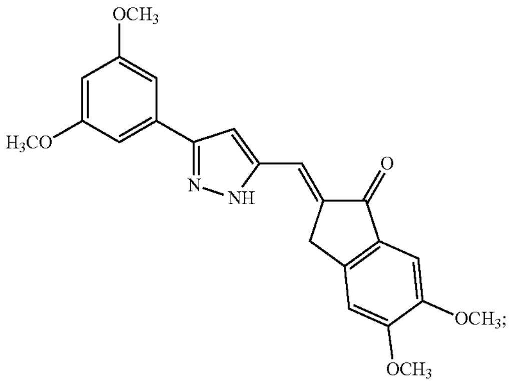
24e
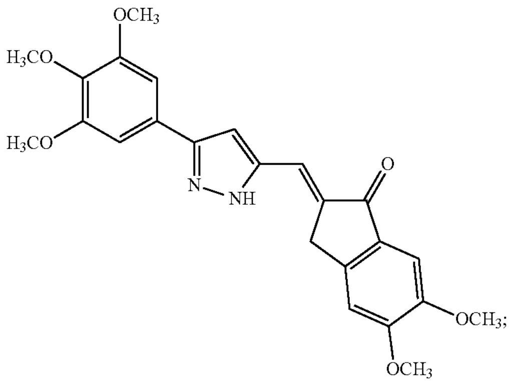
-continued
24f
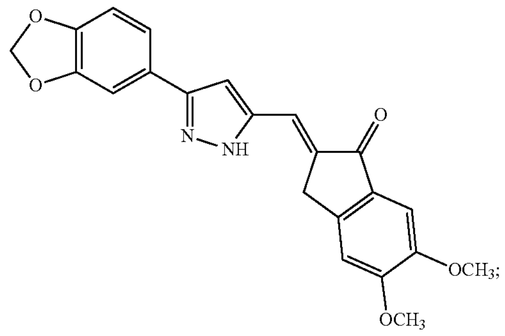
24g
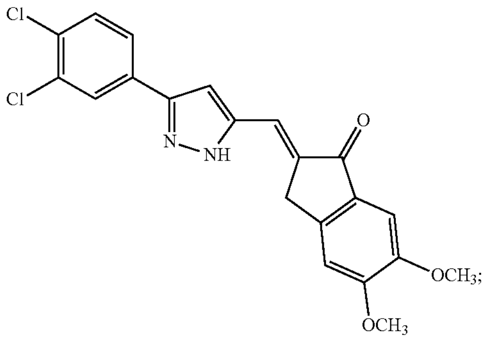
24h
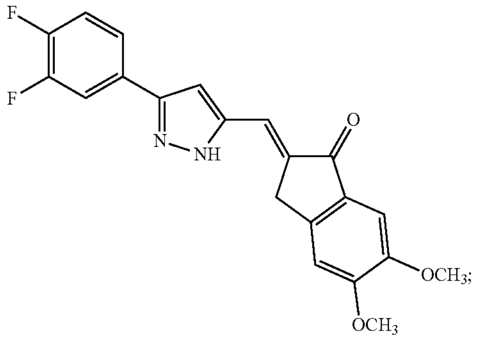
24i
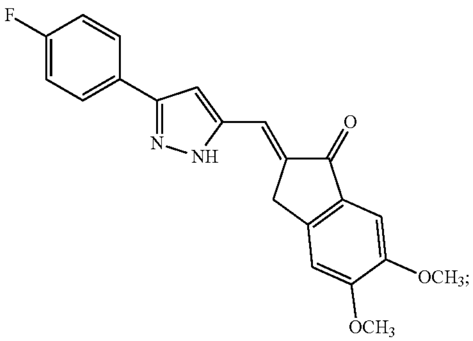

-continued

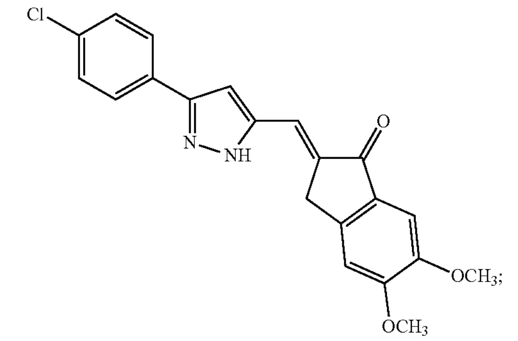

24j

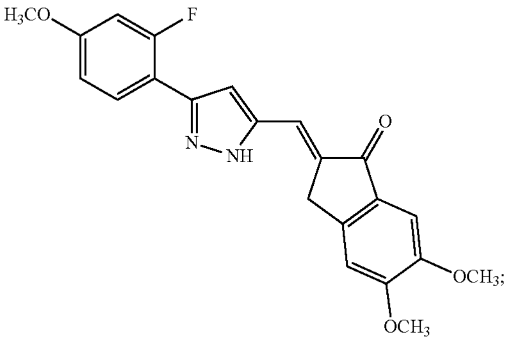

24k and

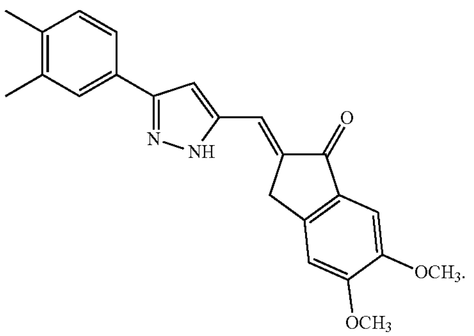

24l

3. A process for the preparation of a pyrazolochalcone compound as claimed in claim 1 or 2, wherein the process comprises reacting 3-aryl-1H-pyrazole-5-carbaldehyde of formula (5a-l)

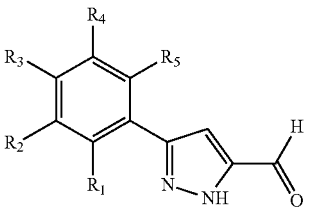

5(a-l)

wherein R, $R_2$, $R_3$, $R_4$, $R_5$ are H, Cl, F, $CH_3$, $OCH_3$ or $R_3$ and $R_4$ are joined by —$OCH_2O$— to form a cyclic structure; with a compound selected from the group consisting of formula a, b, c, d, e, f, g, h, i, j, k, l, m, n, o, p, q, r, and s:

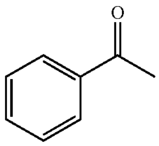

a

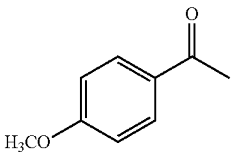

b

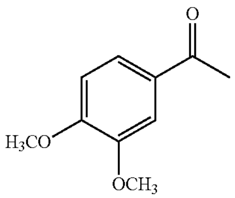

c

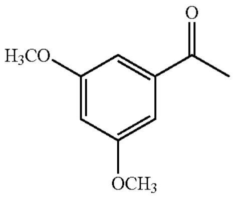

d

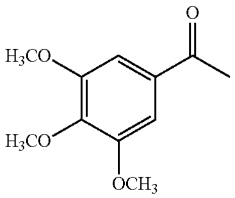

e

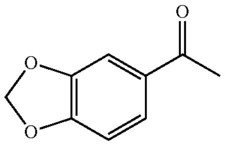

f

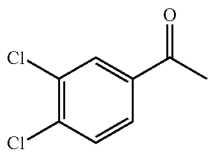

g

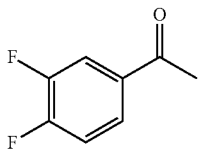

h

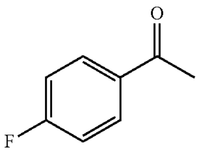

i

-continued j

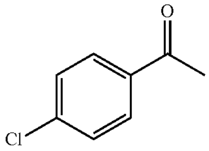

k

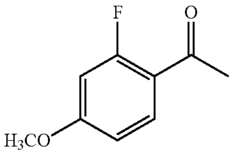

l

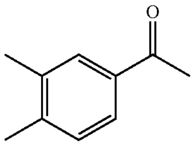

m

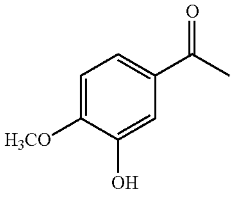

n

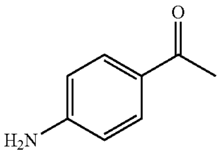

o

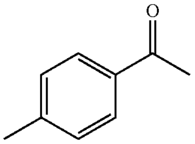

p

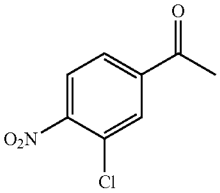

-continued q

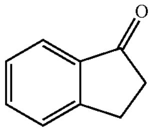

r

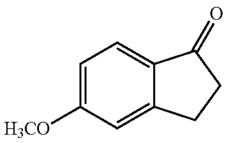

s

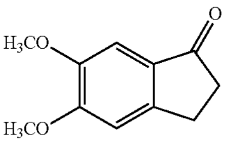

in an alcohol in the presence of a base, at a temperature ranging between 28° C. to 35° C. for a period ranging between 2 to 4 h, to obtain a reaction mixture; evaporating the reaction mixture by vacuum distillation and neutralizing the residue with dilute HCl followed by extraction with a water immiscible solvent;

drying over anhydrous $Na_2SO_4$ and evaporating the solvent to provide a crude product and purifying the product chromatographically using ethyl acetate/hexane as eluent to obtain said pyrazolochalcone.

4. The process as claimed in claim 3, wherein the alcohol is selected from the group consisting of ethanol and methanol.

5. The process as claimed in claim 3, wherein said base is selected from the group consisting of NaOH and KOH.

6. The process as claimed in claim 3, wherein said water immiscible solvent is selected from the group consisting of ethyl acetate, chloroform, and dichloromethane.

7. A method for treating a cancer comprising administering an amount of the compound of claim 1 to a subject sufficient to reduce cell growth of said cancer in said subject.

8. A method for treating a cancer comprising administering an amount of the compound of claim 2 to a subject sufficient to reduce cell growth of said cancer in said subject.

9. The method of claim 7, wherein said cancer is leukemia, non-small lung cancer, colon cancer, central nervous system cancer, melanoma, ovarian cancer, renal cancer, prostate cancer or breast cancer.

10. The method of claim 8, wherein said cancer is leukemia, non-small lung cancer, colon cancer, central nervous system cancer, melanoma, ovarian cancer, renal cancer, prostate cancer or breast cancer.

* * * * *